(12) United States Patent
Nitta

(10) Patent No.: US 9,459,213 B2
(45) Date of Patent: Oct. 4, 2016

(54) METHOD OF DETECTING NUCLEIC ACIDS, METHOD OF OPTICALLY OBSERVING SAMPLE AND FLUORESCENT SUBSTANCE

(75) Inventor: Nao Nitta, Tokyo (JP)

(73) Assignee: Sony Corporation, Tokyo (JP)

( * ) Notice: Subject to any disclaimer, the term of this patent is extended or adjusted under 35 U.S.C. 154(b) by 307 days.

(21) Appl. No.: 13/882,909

(22) PCT Filed: Nov. 4, 2011

(86) PCT No.: PCT/JP2011/006163
§ 371 (c)(1),
(2), (4) Date: May 1, 2013

(87) PCT Pub. No.: WO2012/063441
PCT Pub. Date: May 18, 2012

(65) Prior Publication Data
US 2014/0038176 A1 Feb. 6, 2014

(30) Foreign Application Priority Data

Nov. 11, 2010 (JP) ................................. 2010-252517
Sep. 15, 2011 (JP) ................................. 2011-201542

(51) Int. Cl.
*C12Q 1/68* (2006.01)
*G01N 33/00* (2006.01)
*G01N 21/64* (2006.01)

(52) U.S. Cl.
CPC ......... *G01N 21/6486* (2013.01); *C12Q 1/6816* (2013.01); *C12Q 1/6827* (2013.01); *Y10T 436/143333* (2015.01)

(58) Field of Classification Search
None
See application file for complete search history.

(56) References Cited

U.S. PATENT DOCUMENTS

| | | | | |
|---|---|---|---|---|
| 2001/0006786 A1* | 7/2001 | Sato | ................ | B01J 19/0046 435/6.11 |
| 2002/0160400 A1* | 10/2002 | Lakowicz | .................... | 435/6 |
| 2003/0215842 A1* | 11/2003 | Sledziewski et al. | .......... | 435/6 |
| 2004/0014060 A1 | 1/2004 | Hoheisel et al. | | |
| 2004/0086917 A1* | 5/2004 | Heller | ................ | B01J 19/0046 435/6.18 |
| 2007/0026393 A1 | 2/2007 | Berlin et al. | | |
| 2007/0238117 A1* | 10/2007 | Rajeevan | ............ | C12Q 1/686 435/6.12 |

FOREIGN PATENT DOCUMENTS

DE 10314579 10/2005

OTHER PUBLICATIONS

Supporting Information for Rotaru et al. Angew. Chem. Int. Ed. (2010) 49: 5665-5667.*
Xing et al. Cancer Research (2003) 63: 2316-2321.*
Marsh. Pyrosequencing Protocols (2007) Human Press Inc.*
Park et al. Pancreas (2008) 36(4): e32-e39.*
Fraga et al. BioTechniques (2002) 33: 632-649.*
Sung et al. Carcinogenesis (2005) 26(2): 487-494.*
Goodman et al. Oncogene (2003) 22: 2504-2514.*
Machine translation for DE10314579 A1 obtained on Apr. 13, 2015 from the internet: http://google.com/patents/DE10314579A1?cl=de.*
"Composite". Merriam-Webster. Retrieved on Nov. 4, 2015 from the internet: http://www.merriam-webster.com/dictionary/composite.*
"Composite". The Free Dictionary. Retrieved on Nov. 4, 2015 from the internet: http://www.thefreedictionary.com/composite.*
"Composite". Retrieved on Nov. 4, 2015 from the internet: http://dictionary.reference.com/browse/composite.*
Chan et al. Nucleic Acids Research. 2006. 34(17):e113.*
Chinese Office Action issued Dec. 3, 2013 for corresponding Chinese Appln. No. 201180053204.6.
Rucker et al., "Sequence Specific Fluorescence Detection of Double Strand", J. Am. Chem. Soc., 2003, pp. 1195-1202. vol. 125.
European Search Report issued Feb. 26, 2014 for European Appln. No. 11839814.8.
Bienz et al.. "Two different thresholds of wingless signalling with distinct developmental consequences in the Drosophila midgut," The EMBO Journal, vol. 14, No. 20, pp. 5016-5026, 1995. (11 pages).
Bienz et al., "Specification of a Single Cell Type by a Drosophila Homeotic Gene," Cell, vol. 76, pp. 689-702, Feb. 25, 1994. (14 pages).
Poulson, D.F., "Abstracts of Papers Presented at the 1950 Meetings of the Genetics Society of America," Columbus, Ohio, Sep. 11-14, 1950. (3 pages).
McNulty et al., "Evidence that a copper-metallothionein complex is responsible for fluorescence in acid-secreting cells of the Drosophila stomach," Cell Tissue Res (2001) 304:383-389. (7 pages).
B. K. Filshie et al., "Ultrastructure of the Copper-Accumulating Region of the Drosophila Larval Midgut," Tissue & Cell 1971 3 (1) pp. 77-102. (26 pages).
Jan A. Veenstra, "Peptidergic paracrine and endocrine cells in the midgut of the fruit fly maggot," Cell Tissue Res (2009) 336:309-323. (15 pages).
Stillman, et al., "A luminescence probe for metallothionein in liver tissue: emission intensity measured directly from copper metallothionein induced in rat liver," Nov. 1989, vol. 257, No. 2, pp. 283-286. (4 pages).
Atkinson et al., "Calcium-Activated Potassium Channel Gene Expression in the Midgut of Drosophila," Comp. Biochem. Physiol. vol. 118B, No. 2, pp. 411-420, 1997. (10 pages).

(Continued)

*Primary Examiner* — Robert T Crow
*Assistant Examiner* — Joseph G Dauner
(74) *Attorney, Agent, or Firm* — Chip Law Group

(57) ABSTRACT

[Object] A method of detecting nucleic acids easily without requiring complicated operations such as mixing of liquids and cleaning within micro-scale flow channels.
[Solving Means] A method of detecting nucleic acids including the steps of bringing a sample containing the nucleic acids into contact with copper, and detecting fluorescence emitted from the sample is provided. According to the method of detecting nucleic acids, only by bringing the sample containing nucleic acids into contact with copper, the fluorescence derived from the composite of the nucleic acids and copper can be easily detected.

12 Claims, 40 Drawing Sheets

(56) References Cited

OTHER PUBLICATIONS

Okabe et al., "Direct Visualization of Copper-Metallothionein in LEC Rat Kidneys: Application of Autofluorescence Signal of Copper-Thiolate Cluster," The Journal of Histochemistry and Cytochemistry, vol. 44, No. 8, pp. 865-873, 1996. (9 pages).

Quaglia et al., "Copper-Metallothionein Autofluorescence," Image of the Month, Hepatology, vol. 50, No. 4, 2009, pp. 1312-1313. (2 pages).

M. Beltramini et al., "Metal Substitution of Neurospora Copper Metallothionein," Biochemistry 1984, vol. 23, pp. 3422-3427. (6 pages).

K. Munger et al., "(Cu,Zn)-Metallothioneins from Fetal Bovine Liver," The Journal of Biological Chemistry, vol. 260. No. 18, Issue of Aug. 25, 1985, pp. 10032-10038. (7 pages).

M. Beltramini et al., "Primary Structure and Spectroscopic Studies of Neurospora Copper Metallothionein," Environmental Health Perspectives, vol. 65, pp. 21-27, 1986, pp. 21-27. (7 pages).

J. Byrd et al., "Characterization of the Copper-Thiolate Cluster in Yeast Metallothionein and Two Truncated Mutants*," The Journal of Biological Chemistry, vol. 263, No. 14, Issue of May 15, 1988, pp. 6688-6694. (7 pages).

M. Beltramini et al., "Luminescence emission from Neurospora copper metallothionein," Biochem. J. (1989) 260, pp. 189-193. (5 pages).

S. Narula et al., "Establishment of the Metal-to-Cysteine Connectivities in Silver-Substituted Yeast Metallothionein," J. Am. Chem. Soc. 1991, vol. 113, pp. 9354-9358. (5 pages).

S. Narula et al., Copper- and Silver-Substituted Yeast Metallothioneins: Sequential H NMR Assignments Reflecting Conformational Heterogeneity at the C Terminus, Biochemistry 1993, vol. 32, pp. 6773-6787. (15 pages).

Z. Gasyna et al., "Luminescence Decay from Copper(I) Complexes of Metallothionein," Inorganica Chimica Acta, vol. 153 (1988), pp. 115-118. (4 pages).

Fred E. Lytle, "Solution Luminescence of Metal Complexes," Applied Spectroscopy, Review Papers, vol. 24, No. 3, 1970, pp. 319-326. (8 pages).

J. H. Anglin, Jr., et al., "Fluorescence of Cu, Au and Ag Mercaptides," Photochemistry and Photobiology, 1971, vol. 13., pp. 279-281. (3 pages).

H. Kuiper et al., "Luminescence of carbon monoxide hemocyanins," Proc. Natl. Acad. Sci. USA, Biochemistry, vol. 77, No. 5, May 1980, pp. 2387-2389. (3 pages).

F. Sabin et al., "Photophysical Properties of Hexanuclear Copper(I) and Silver(1) Clusters," Inorg. Chem., vol. 31, 1992, pp. 1941-1945. (5 pages).

P. Ford et al., "Photochemical and Photophysical Properties of Tetranuclear and Hexanuclear Clusters of Metals with d10 and s2 Electronic Configurations," Acc. Chem. Res., vol. 26, 1993, pp. 220-226. (7 pages).

Prutz et al., "Interaction of copper(I) with nucleic acids," International Journal of Radiation Biology, Vol. 58, No. 2, 1990, pp. 215-234. (11 pages).

V. Rostovtsev et al., A Stepwise Huisgen Cycloaddition Process: Copper(I)-Catalyzed Regioselective "Ligation" of Azides and Terminal Alkynes, Angew. Chem. Int. Ed. 2002, vol. 41, No. 14, pp. 2596-2599. (4 pages).

V. T. Bowen et al., "The Chemistry and Physiology of the Nucleus," Proceedings of the Symposium held Aug. 1951 by the Biology Department, Brookhaven National Laboratory. (11 pages).

A. Rotaru et al., "Selective dsDNA-Templated Formation of Copper Nanoparticles in Solution," Angew. Chem. Int. Ed. 2010, vol. 49, pp. 5665-5667. (3 pages).

Lonza Walkersville, Inc., DAPI Nucleic Acid Stain Instruction and Information Guidelines. 2008. (3 pages).

Lonza Walkersville, Inc., Hoechst 33342, trichloride, trihydrate Instruction and Information Guidelines. 2008. (1 page).

Beltramini et al., "Luminescence Properties of Neurospora Copper Metallothionein", FEBS Letters, May 1981, vol. 127, No. 2, pp. 201-203.

Kuiper et al., "Luminescence of the Copper—Carbon Monoxide Complex of Neurospora Tyrosinase", FEBS Letters, Feb. 1980, vol. 111, No. 1, pp. 232-234.

Presta et al., "Incorporation of Copper into the Yeast *Saccharomyces cerevisiae*. Identificatino of Cu(I)-Metallothionein In Intact Yeast Cells", Journal of Inorganic Biochemistry, 1997, vol. 66, Department of Chemistry, University of Western Ontario, London, Ontario, Canada, pp. 231-240.

M. Beltramini et al., Copper Transfer Between Neurospora Copper Metallothionein and Type 3 Copper Apoproteins, FEBS Letters, vol. 142, No. 2, Jun. 1982, pp. 219-222.

* cited by examiner

SEQUENCE LISTING

```
<160> NUMBER OF SEQ ID NOS: 33

<210> SEQ ID NO 1
<211> LENGTH: 20
<212> TYPE: DNA
<213> ORGANISM: Artificial Sequence
<220> FEATURE:
<223> OTHER INFORMATION: Synthesized: Oligo-DNA 1

<400> SEQUENCE: 1
aaaaaaaaaa aaaaaaaaaa                                              20

<210> SEQ ID NO 2
<211> LENGTH: 20
<212> TYPE: DNA
<213> ORGANISM: Artificial Sequence
<220> FEATURE:
<223> OTHER INFORMATION: Synthesized: Oligo-DNA 2

<400> SEQUENCE: 2
tttttttttt tttttttttt                                              20

<210> SEQ ID NO 3
<211> LENGTH: 20
<212> TYPE: DNA
<213> ORGANISM: Artificial Sequence
<220> FEATURE:
<223> OTHER INFORMATION: Synthesized: Oligo-DNA 3

<400> SEQUENCE: 3
gggggggggg gggggggggg                                              20

<210> SEQ ID NO 4
<211> LENGTH: 20
<212> TYPE: DNA
<213> ORGANISM: Artificial Sequence
```

```
<220> FEATURE:
<223> OTHER INFORMATION: Synthesized: Oligo-DNA 4

<400> SEQUENCE: 4
cccccccccc cccccccccc                                               20

<210> SEQ ID NO 5
<211> LENGTH: 20
<212> TYPE: DNA
<213> ORGANISM: Artificial Sequence
<220> FEATURE:
<223> OTHER INFORMATION: Synthesized: Oligo-DNA 5

<400> SEQUENCE: 5
aaaaaataaa taataaaaaa                                               20

<210> SEQ ID NO 6
<211> LENGTH: 20
<212> TYPE: DNA
<213> ORGANISM: Artificial Sequence
<220> FEATURE:
<223> OTHER INFORMATION: Synthesized: Oligo-DNA 6

<400> SEQUENCE: 6 tttttttatta tttatttttt                                              20

<210> SEQ ID NO 7
<211> LENGTH: 20
<212> TYPE: DNA
<213> ORGANISM: Artificial Sequence
<220> FEATURE:
<223> OTHER INFORMATION: Synthesized: Oligo-DNA 7

<400> SEQUENCE: 7
ggggggcggg cggcgggggg                                               20

<210> SEQ ID NO 8
<211> LENGTH: 20
<212> TYPE: DNA
<213> ORGANISM: Artificial Sequence
<220> FEATURE:
<223> OTHER INFORMATION: Synthesized: Oligo-DNA 8

<400> SEQUENCE: 8
ccccccgccg cccgcccccc                                               20

<210> SEQ ID NO 9
<211> LENGTH: 20
<212> TYPE: DNA
<213> ORGANISM: Artificial Sequence
<220> FEATURE:
<223> OTHER INFORMATION: Synthesized: Oligo-DNA 9

<400> SEQUENCE: 9
aaaatttttt ttttttaaaa                                               20

<210> SEQ ID NO 10
<211> LENGTH: 6
<212> TYPE: DNA
<213> ORGANISM: Artificial Sequence
<220> FEATURE:
<223> OTHER INFORMATION: Synthesized: Oligo-DNA 10

<400> SEQUENCE: 10 tttttt                                                               6
```

```
<210> SEQ ID NO 11
<211> LENGTH: 3
<212> TYPE: DNA
<213> ORGANISM: Artificial Sequence
<220> FEATURE:
<223> OTHER INFORMATION: Synthesized: Oligo-DNA 11

<400> SEQUENCE: 11 aaa                                                                        3

<210> SEQ ID NO 12
<211> LENGTH: 3
<212> TYPE: DNA
<213> ORGANISM: Artificial Sequence
<220> FEATURE:
<223> OTHER INFORMATION: Synthesized: Oligo-DNA 12

<400> SEQUENCE: 12 ttt                                                                        3

<210> SEQ ID NO 13
<211> LENGTH: 3
<212> TYPE: DNA
<213> ORGANISM: Artificial Sequence
<220> FEATURE:
<223> OTHER INFORMATION: Synthesized: Oligo-DNA 13

<400> SEQUENCE: 13 tta                                                                        3

<210> SEQ ID NO 14
<211> LENGTH: 3
<212> TYPE: DNA
<213> ORGANISM: Artificial Sequence
<220> FEATURE:
<223> OTHER INFORMATION: Synthesized: Oligo-DNA 14

<400> SEQUENCE: 14 tat                                                                        3

<210> SEQ ID NO 15
<211> LENGTH: 3
<212> TYPE: DNA
<213> ORGANISM: Artificial Sequence
<220> FEATURE:
<223> OTHER INFORMATION: Synthesized: Oligo-DNA 15

<400> SEQUENCE: 15 att                                                                        3

<210> SEQ ID NO 16
<211> LENGTH: 3
<212> TYPE: DNA
<213> ORGANISM: Artificial Sequence
<220> FEATURE:
<223> OTHER INFORMATION: Synthesized: Oligo-DNA 16

<400> SEQUENCE: 16 taa                                                                        3

<210> SEQ ID NO 17
<211> LENGTH: 3
<212> TYPE: DNA
<213> ORGANISM: Artificial Sequence
<220> FEATURE:
<223> OTHER INFORMATION: Synthesized: Oligo-DNA 17
```

```
<400> SEQUENCE: 17 ata                                                                  3

<210> SEQ ID NO 18
<211> LENGTH: 3
<212> TYPE: DNA
<213> ORGANISM: Artificial Sequence
<220> FEATURE:
<223> OTHER INFORMATION: Synthesized: Oligo-DNA 18

<400> SEQUENCE: 18 aat                                                                  3

<210> SEQ ID NO 19
<211> LENGTH: 10
<212> TYPE: DNA
<213> ORGANISM: Artificial Sequence
<220> FEATURE:
<223> OTHER INFORMATION: Synthesized: Oligo-DNA 19

<400> SEQUENCE: 19
tttttttttt                                                          10

<210> SEQ ID NO 20
<211> LENGTH: 10
<212> TYPE: DNA
<213> ORGANISM: Artificial Sequence
<220> FEATURE:
<223> OTHER INFORMATION: Synthesized: Oligo-DNA 20

<400> SEQUENCE: 20
uuuuuuuuug                                                          10

<210> SEQ ID NO 21
<211> LENGTH: 20
<212> TYPE: DNA
<213> ORGANISM: Artificial Sequence
<220> FEATURE:
<223> OTHER INFORMATION: Synthesized: Oligo-DNA 21

<400> SEQUENCE: 21
cccctttttt tttttccccc                                               20

<210> SEQ ID NO 22
<211> LENGTH: 20
<212> TYPE: DNA
<213> ORGANISM: Artificial Sequence
<220> FEATURE:
<223> OTHER INFORMATION: Synthesized: Oligo-DNA 22

<400> SEQUENCE: 22
ccccccccTt tttttttttt                                               20

<210> SEQ ID NO 23
<211> LENGTH: 20
<212> TYPE: DNA
<213> ORGANISM: Artificial Sequence
<220> FEATURE:
<223> OTHER INFORMATION: Synthesized: Oligo-DNA 23

<400> SEQUENCE: 23
tttttttttt ttcccccccc                                               20

<210> SEQ ID NO 24
```

```
<211> LENGTH: 20
<212> TYPE: DNA
<213> ORGANISM: Artificial Sequence
<220> FEATURE:
<223> OTHER INFORMATION: Synthesized: Oligo-DNA 24

<400> SEQUENCE: 24
ccttttttcc ccttttttcc                                                  20

<210> SEQ ID NO 25
<211> LENGTH: 20
<212> TYPE: DNA
<213> ORGANISM: Artificial Sequence
<220> FEATURE:
<223> OTHER INFORMATION: Synthesized: Oligo-DNA 25

<400> SEQUENCE: 25
ctttcctttc ctttcctttc                                                  20

<210> SEQ ID NO 26
<211> LENGTH: 20
<212> TYPE: DNA
<213> ORGANISM: Artificial Sequence
<220> FEATURE:
<223> OTHER INFORMATION: Synthesized: Oligo-DNA 26

<400> SEQUENCE: 26
ccttcttctt cttcttcttc                                                  20

<210> SEQ ID NO 27
<211> LENGTH: 6
<212> TYPE: DNA
<213> ORGANISM: Artificial Sequence
<220> FEATURE:
<223> OTHER INFORMATION: Synthesized: Oligo-DNA 27

<400> SEQUENCE: 27 tttttt                                                                  6

<210> SEQ ID NO 28
<211> LENGTH: 5
<212> TYPE: DNA
<213> ORGANISM: Artificial Sequence
<220> FEATURE:
<223> OTHER INFORMATION: Synthesized: Oligo-DNA 28

<400> SEQUENCE: 28 ttttt                                                                   5

<210> SEQ ID NO 29
<211> LENGTH: 2
<212> TYPE: DNA
<213> ORGANISM: Artificial Sequence
<220> FEATURE:
<223> OTHER INFORMATION: Synthesized: Oligo-DNA 29

<400> SEQUENCE: 29 tt                                                                      2

<210> SEQ ID NO 30
<211> LENGTH: 10
<212> TYPE: DNA
<213> ORGANISM: Artificial Sequence
<220> FEATURE:
<223> OTHER INFORMATION: Synthesized: Oligo-DNA 30

<400> SEQUENCE: 30
```

```
aaaaaaaaaa                                                                    10

<210> SEQ ID NO 31
<211> LENGTH: 10
<212> TYPE: DNA
<213> ORGANISM: Artificial Sequence
<220> FEATURE:
<223> OTHER INFORMATION: Synthesized: Oligo-DNA 31
<220> FEATURE:
<221> NAME/KEY: misc_feature
<222> LOCATION: (1)..(9)
<220> FEATURE:
<221> NAME/KEY: misc_feature
<222> LOCATION: (1)..(9)
<223> OTHER INFORMATION: n is a, c, g, or t

<400> SEQUENCE: 31 nnnnnnnnng                                                                    10

<210> SEQ ID NO 32
<211> LENGTH: 10
<212> TYPE: DNA
<213> ORGANISM: Artificial Sequence
<220> FEATURE:
<223> OTHER INFORMATION: Synthesized: Oligo-DNA 32

<400> SEQUENCE: 32
cccccccccc                                                                    10

<210> SEQ ID NO 33
<211> LENGTH: 10
<212> TYPE: DNA
<213> ORGANISM: Artificial Sequence
<220> FEATURE:
<223> OTHER INFORMATION: Synthesized: Oligo-DNA 33
<220> FEATURE:
<221> NAME/KEY: misc_feature
<222> LOCATION: (3)..(8)
<223> OTHER INFORMATION: n is 5-Methyl-2-deoxycytidine.

<400> SEQUENCE: 33 ccnnnnnncc                                                                    10
```

METHOD OF DETECTING NUCLEIC ACIDS, METHOD OF OPTICALLY OBSERVING SAMPLE AND FLUORESCENT SUBSTANCE

CROSS REFERENCES TO RELATED APPLICATIONS

The present application is a national stage of International Application No. PCT/JP2011/006163 filed on Nov. 4, 2011 and claims priority to Japanese Patent Application No. 2010-252517 filed on Nov. 11, 2011, and Japanese Patent Application No. 2011-201542 filed on Sep. 15, 2011, the disclosure of which is incorporated herein by reference.

BACKGROUND

The present technology relates to a method of detecting nucleic acids, a method of optically observing a sample and a fluorescent substance. More particularly, the present technology relates to a method of detecting nucleic acids, a method of optically observing a sample, both method being based on fluorescence emitted from the nucleic acids contacted with copper, and a fluorescent substance including copper and nucleic acids.

In recent years, technical research has been widely taken place by using nucleic acids in a variety of fields including a medical field, a drug discovery field, a clinical examination field, a food field, an agricultural field, an engineering field, a forensic medicine field and a criminal identification field. Recently, a lab-on-chip is technically developed and is practically used to stain, detect, amplify etc. nucleic acids within micro-scale flow channels disposed in a microchip.

As a fundamental technique for detecting nucleic acids, there is a method of using a fluorescent pigment for staining the nucleic acids. Many fluorescent pigments are known such as hoechst33342, DAPI, ethidium bromide, SYBR green and the like. For example, hoechst33342 and DAPI are used for the purpose of staining nucleic acids in cells or tissues in a flow cytometry or a microscope. The ethidium bromide is frequently used to stain nucleic acid molecules in an electrophoresis. The SYBR green and the like are also used for the purpose of detecting in a real time an amplification process of the nucleic acids in a nucleic acid amplification technology such as a polymerase chain reaction.

In relation to the present technology, conventionally known autofluorescence shown by cells upon a fluorescence observation will be described. One of the fluorescence is orange-colored autofluorescence shown by UV-irradiated cells in the presence of copper. For example, it is reported that cells of a particular part of a *drosophila* larvae midgut emits orange-colored fluorescence when copper is added (see Non-Patent Documents 1 to 8). The cells where the orange-colored fluorescence is especially strongly observed in the *drosophila* larvae midgut are called as "copper cells" or the like. It is reported that the fluorescence is observed at cells around the copper cells (Non-Patent Document 4) and an entire body wall of the larvae (Non-Patent Document 2) when the concentration of the copper added is increased.

There is a description that the above-mentioned orange-colored fluorescence is observed at both cytoplasms and cell nuclei in cells, and, in particular, is detected predominantly in grains of the cytoplasms (see Non-Patent Documents 2 to 4 and 7). There is a description that a wavelength range of fluorescence is 590 to 630 nm, a peak wavelength is 610 nm and a maximum excitation wavelength is 340 nm (see Non-Patent Document 3).

Also for organisms other than *drosophila*, autofluorescence having similar properties is observed. For example, there is reported that orange-colored fluorescence (having a peak wavelength of 605 nm) is observed in an individual liver to which copper is added by UV excitation (excitation wavelength of 310 nm) in rat experiments (see Non-Patent Document 9). Furthermore, there is reported that similar fluorescence is observed in a kidney of a model rat having a kidney and a liver where copper is accumulated with aging (see Non-Patent Document 10). Also, the autofluorescence having similar properties is reported in yeast (see Non-Patent Document 11) and human liver tissues of a Wilson's disease patient (see Non-Patent Document 12). The Wilson's disease is a genetic disorder of insufficient excretion of copper and accumulation of copper in liver cells.

As the above-described fluorescent substance emitting orange-colored fluorescence, a composite of copper and metallothionein (MT) (hereinafter abbreviated to as "Cu-MT") is presumed (see Non-Patent Documents 14 to 23). The Cu-MT has wavelength properties such as an excitation wavelength of 305 nm and a fluorescence wavelength of 565 nm in Non-Patent Document 13, and an excitation wavelength of 310 nm and a fluorescence wavelength of 570 nm in Non-Patent Document 17. It is conceivable that the Cu-MT contain monovalent copper ions (Cu(I)) (see Non-Patent Documents 13, 15, 17, 19 and 23).

As the fluorescent substance containing copper, a compound containing pyrimidine or mercaptide that emits fluorescence by interacting pyrimidine or mercaptide with copper is widely known (see Non-Patent Documents 24 to 29).

On the other hand, an interaction of various metal ions with nucleic acids has been traditionally studied. For example, it is known that when monovalent copper ions are interacted with nucleic acids, a minor amount of copper contained in cell nuclei stabilizes a nucleic acid structure, but hurts DNAs under coexistence of hydrogen peroxide (see Non-Patent Document 30). It is also reported that an interaction with copper changes an absorption spectrum of DNAs (see Non-Patent Documents 30 and 31). Further, it is reported that the change in the absorption spectrum depends on base sequences (specifically, a polymer having a G-C pair and a polymer having an A-T pair) of the DNAs (see Non-Patent Document 30).

CITATION LIST

Non-Patent Documents

Non-Patent Document 1: Physiological genetic studies on copper metabolism in the genus *Drosophila*. (1950) Genetics 35, 684-685

Non-Patent Document 2: Organization and function of the inorganic constituents of nuclei. (1952) Exp. Cell Res., Suppl. 2:161-179

Non-Patent Document 3: Ultrastructure of the copper-accumulating region of the *Drosophila* larval midgut. (1971) Tissue Cell. 3, 77-102

Non-Patent Document 4: Specification of a single cell type by a *Drosophila* homeotic gene. (1994) Cell. 76, 689-702

Non-Patent Document 5: Two different thresholds of wingless signalling with distinct developmental consequences in the *Drosophila* midgut. (1995) EMBO J. 14, 5016-5026

Non-Patent Document 6: Calcium-activated potassium channel gene expression in the midgut of *Drosophila*. (1997) Comp. Biochem. Physiol. B Biochem. Mol. Biol. 118, 411-420

Non-Patent Document 7: Evidence that a copper-metallothionein complex is responsible for fluorescence in acid-secreting cells of the *Drosophila* stomach. (2001) Cell Tissue Res. 304, 383-389

Non-Patent Document 8: Peptidergic paracrine and endocrine cells in the midgut of the fruit fly maggot. (2009) Cell Tissue Res. 336, 309-323

Non-Patent Document 9: A luminescence probe for metallothionein in liver tissue: emission intensity measured directly from copper metallothionein induced in rat liver. (1989) FEBS Lett. 257, 283-286

Non-Patent Document 10: Direct visualization of copper-metallothionein in LEC rat kidneys: application of autofluorescence signal of copper-thiolate cluster. (1996) J. Histochem. Cytochem. 44, 865-873

Non-Patent Document 11: Incorporation of copper into the yeast Saccharomyces cerevisiae. Identification of Cu(I)-metallothionein in intact yeast cells. (1997) J. Inorg. Biochem. 66, 231-240

Non-Patent Document 12: Portmann B. Image of the month. Copper-metallothionein autofluorescence. (2009) Hepatology. 50, 1312-1313

Non-Patent Document 13: Luminescence properties of *Neurospora* copper metallothionein. (1981) FEBS Lett. 127, 201-203

Non-Patent Document 14: Copper transfer between *Neurospora* copper metallothionein and type 3 copper apoproteins. (1982) FEBS Lett. 142, 219-222

Non-Patent Document 15: Spectroscopic studies on *Neurospora* copper metallothionein. (1983) Biochemistry. 22, 2043-2048

Non-Patent Document 16: Metal substitution of *Neurospora* copper metallothionein. (1984) Biochemistry. 23, 3422-3427

Non-Patent Document 17: (Cu,Zn)-metallothioneins from fetal bovine liver. Chemical and spectroscopic properties. (1985) J. Biol. Chem. 260, 10032-10038

Non-Patent Document 18: Primary structure and spectroscopic studies of *Neurospora* copper metallothionein. (1986) Environ. Health Perspect. 65, 21-27

Non-Patent Document 19: Characterization of the copper-thiolate cluster in yeast metallothionein and two truncated mutants. (1988) J. Biol. Chem. 263, 6688-6694

Non-Patent Document 20: Luminescence emission from *Neurospora* copper metallothionein. Time-resolved studies. (1989) Biochem J. 260, 189-193

Non-Patent Document 21: Establishment of the metal-to-cysteine connectivities in silver-substituted yeast metallothionein (1991) J. Am. Chem. Soc. 113, 9354-9358

Non-Patent Document 22: Copper- and silver-substituted yeast metallothioneins: Sequential proton NMR assignments reflecting conformational heterogeneity at the C terminus. (1993) Biochemistry. 32, 6773-6787

Non-Patent Document 23: Luminescence decay from copper (I) complexes of metallothionein. (1998) Inorg. Chim. Acta. 153, 115-118

Non-Patent Document 24: Solution Luminescence of Metal Complexes. (1970) Appl. Spectrosc. 24, 319-326

Non-Patent Document 25: Fluorescence of Cu, Au and Ag mercaptides. (1971) Photochem. Photobiol. 13, 279-281

Non-Patent Document 26: Luminescence of the copper-carbon monoxide complex of *Neurospora* tyrosinase. (1980) FEBS Lett. 111, 232-234

Non-Patent Document 27: Luminescence of carbon monoxide hemocyanins. (1980) Proc. Natl. Acad. Sci. U.S.A. 77, 2387-2389

Non-Patent Document 28: Photophysical properties of hexanuclear copper(I) and silver(I) clusters. (1992) Inorg. Chem., 31, 1941-1945

Non-Patent Document 29: Photochemical and photophysical properties of tetranuclear and hexanuclear clusters of metals with d10 and s2 electronic configurations. (1993) Acc. Chem. Res. 26, 220-226

Non-Patent Document 30: Interaction of copper(I) with nucleic acids. (1990) Int. J. Radiat. Biol. 58, 215-234

Non-Patent Document 31: Copper(I)-Catalyzed Regioselective "Ligation" of Azides and Terminal Alkynes. (2002) Ang. Chem. Int. Ed. 41, 2596-2599

SUMMARY

Problem to be Solved by the Invention

When nucleic acids are stained with the above-described existing fluorescent reagents, it is required to mix a liquid reagent with a sample and an operation becomes undesirably complicated. In particular, in the lab-on-chip for staining and detecting nucleic acids within micro-scale flow channels, a production, storage and a use of chips become very complicated.

A main object of the present technology is to provide a method of detecting nucleic acids easily without requiring complicated operations such as mixing of liquids and cleaning within micro-scale flow channels.

Means for Solving the Problem

In order to solve the above-described problems, the present technology provides a method of detecting nucleic acids including the steps of: bringing a sample containing the nucleic acids into contact with copper, and detecting fluorescence emitted from the sample. According to the method of detecting nucleic acids, only by bringing the sample containing nucleic acids into contact with copper, the fluorescence derived from the composite of the nucleic acids and copper can be easily detected. In addition, based on the intensity and/or the spectrum of the fluorescence detected, information about the concentration, the distribution or the shape of the nucleic acids contained in the sample can be provided.

In particular, the intensity and the spectrum of the fluorescence derived from the composite of the nucleic acids and copper change depending on base sequences and a length of the nucleic acids as well as presence or absence of a mismatch in double-stranded nucleic acids. Accordingly, the method of detecting nucleic acids can analyze the base sequences of the nucleic acids and the mismatch in a double strand by the nucleic acids based on the intensity and/or the spectrum of the fluorescence detected in the detection step.

Also, the fluorescence derived from the composite of the nucleic acids and copper is higher in uracil than that in cytosine. Therefore, by the method of detecting nucleic acids, non-methylated cytosine contained in the sample is selectively converted into uracil by a bisulfate treatment, and the intensity and/or the spectrum change amount of the fluorescence detected in the detection step are determined, thereby analyzing presence or absence of the methylation or demethylation and its amount of cytosine in the nucleic acids, the position of methylated cytosine or demethylated cytosine etc. in the base sequences.

In the method of detecting nucleic acids, the copper can be solid.

In the method of detecting nucleic acids, the contact step is preferably conducted by bringing the sample containing the nucleic acids into contact with the copper under coexistence of a salt. Also, the contact step is preferably conducted by irradiating the sample with a light having a wavelength of 300 to 420 μm to detect the fluorescence emitted from the sample.

The present technology provides a method of optically observing a sample including the steps of: bringing the sample containing nucleic acids into contact with copper, and detecting the fluorescence emitted from the sample.

In the optical observation method, the sample may be cells. In this case, information about a distribution, a position, a number, a size, a shape or the like of cell nuclei in the cells can be provided.

In addition, the present technology provides a fluorescent substance including a compound containing copper and nucleic acids. By changing base sequences and a length of nucleic acids in the compound as appropriate, various fluorescent substances having different spectra or intensities can be provided.

According to the present technology, the "nucleic acids" include natural nucleic acids (DNAs and RNAs). The "nucleic acids" widely involve artificial nucleic acids provided by artificially changing a chemical structure of ribose of the natural nucleic acids or a chemical structure of a phosphodiester linkage. Non-limiting examples of the artificial nucleic acids include peptide nucleic acids (RNAs), phosphorothioate type oligonucleotides (S-oligos), bridged nucleic acids (BNAs), locked nucleic acids (LNAs) and the like.

Effect of the Invention

The present technology provides a method of detecting nucleic acids easily without requiring complicated operations such as mixing of liquids and cleaning within microscale flow channels.

Additional features and advantages are described herein, and will be apparent from the following Detailed Description and the figures.

DETAILED DESCRIPTION

Figure 1:
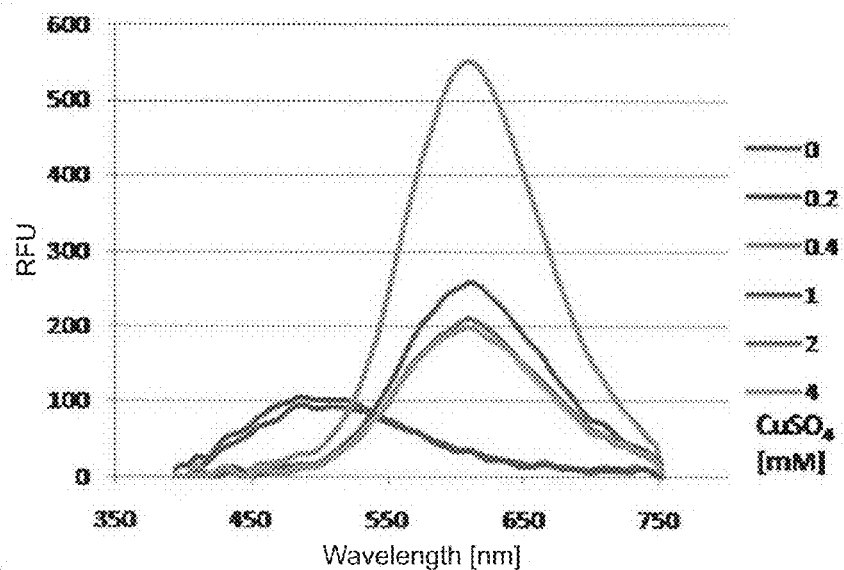
FIG. 1 Graphs each substituting a drawing and showing a fluorescent spectrum and an RFU value obtained by bringing ssDNAs into contact with $CuSO_4$ having a varied concentration under the condition of an S.A. concentration of 50 mM; (A) shows the fluorescent spectrum and (B) shows a peak RFU value (Example 1).
Figure 1:
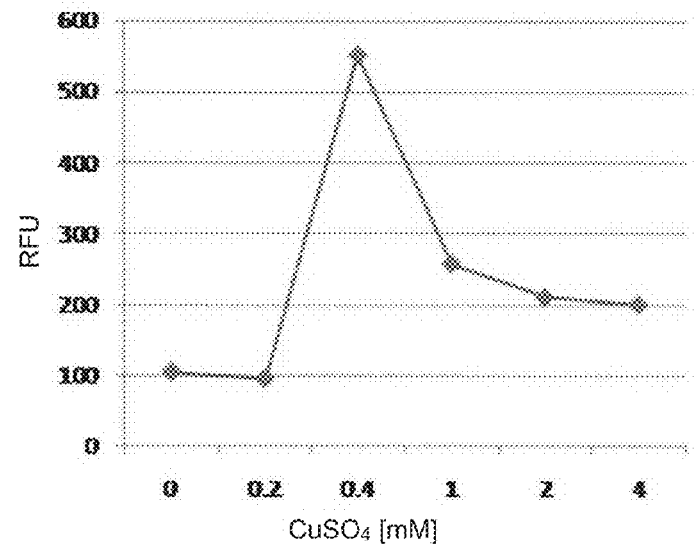

Hereinafter, embodiments according to the present technology will be described with reference to the drawings. The embodiments described below are provided for purposes of illustration only, and merely depict typical embodiments of the present technology, and the scope of the present technology should not be construed narrower. The embodiments will be described in the following order.

<A> Method of Detecting Nucleic Acids
1. Contact Step
(1) Copper (Cu)
(2) Sample
(3) Reaction Solution
(4) Contact Conditions
2. Detection Step
(1) Light Irradiation
(2) Fluorescence Detection
(3) Detection of Fluorescent Spectrum
(4) Detection of Fluorescence Space Distribution
3. Base Sequence Analysis
4. Applications
(1) Detection of Difference in Fine Gene Sequences
(2) Analysis of Methylation of DNA Molecules
(3) Observation and Measurement of Cell Nuclei
(4) Analysis of Fine Particles
(5) Application to Lab-On-Chip
<B> Fluorescent Pigment
<A> Method of Detecting Nucleic Acids The present inventor has newly discovered that a composite of nucleic acids (DNAs or RNAs) and copper emits fluorescence, as described in Examples below in detail. It has been also discovered that a fluorescent spectrum and a fluorescence intensity are changed depending on base sequences and a length of the nucleic acids, and that a fluorescent spectrum and a fluorescence intensity are changed depending on presence or absence of a mismatch in double-stranded nucleic acids. The present technology is achieved by the novel discoveries. As described above, it is conventionally known that an absorption spectrum of DNAs is changed by an interaction with copper and that the change in the absorption spectrum depends on base sequences of the DNAs. However, it is not known in the past that the composite of the nucleic acids and copper emits fluorescence. The fluorescence emitted by the composite has similar wavelength properties as those of the fluorescence emitted by the Cu-MT as described above, but is observed in a reaction system containing no metallothionein using a purified synthetic oligonucleotide, which is totally different from the fluorescence emitted by the Cu-MT. Hereinafter, a method of detecting nucleic acids according to the present technology, applications therefor and a fluorescent substance according to the present technology will be specifically described.

A method of detecting nucleic acids according to the present technology includes the steps of: bringing a sample containing the nucleic acids into contact with copper, and detecting the fluorescence emitted from the sample. In the method of detecting nucleic acids according to the present technology, the base sequences of the nucleic acids can be analyzed and a mismatch in a double strand formed by the nucleic acids can be analyzed based on the intensity and/or the spectrum of the fluorescence detected in the detection step in accordance with the purposes.

1. Contact Step

In the contact step, a sample containing nucleic acids is contacted with copper.

(1) Copper (Cu)

A configuration of copper used in the step is preferably a solution containing copper or a solid matter containing copper. In a case that an easy operation is required, the solid matter is preferably used. In a case that nucleic acids are detected within micro-scale flow channels disposed in a microchip, the use of the solid matter allows the copper to be incorporated into the microchip, which preferably results in a simplified chip structure. Also, the solid matter has a shape or properties stable to vibration, impact, heat, light, time and the like as compared with the solution. On the other hand, the solution may be preferable when the reaction time should be shortened. The configuration of copper can be selected as appropriated depending on the purposes.

When a copper solution is used, the solution preferably contains a sufficient amount of copper (I) ions. In general, divalent copper cations are stable, and monovalent copper cations are less stable than the divalent copper cations. For this reason, it is preferable that a reducing agent that reduces copper (II) ions to copper (I) ions be mixed with the solution containing divalent copper cations such as a $CuSO_4$ solution. As the reducing agent, sodium ascorbate can be used.

Another method to provide a sufficient amount of copper (I) ions to the solution is to irradiate the solution containing copper (II) ions with radiation to generate copper (I) ions (see Non-Patent Document 30). Alternatively, a salt such as CuI, $CuOTf.C_6H_6$ and $[Cu(NCCH_3)_4][PF_6]$ may be dissolved into a solution containing acetonitrile and an equivalent of a nitrogen base (2,6-lutidine, triethylamine, diisopropylethylamine, pyridine etc.) to provide a copper (I) ion solution desirably under oxygen-free conditions (see Non-Patent Document 31).

When copper in a solid state (solid copper) is used, an alloy containing copper can be used as well as pure copper. Non-limiting examples of the shape of copper include powder, fine particles, rod, wire, plate and foil. It is also possible that a thin film containing copper be formed on a surface (inner surface) of a substrate or a container of a microchip into which a sample is introduced.

It is preferable that the solid copper have a shape and be disposed such that light detected in a detection step as described later is not blocked, not reflected etc. For example, the solid copper may be disposed inside of the substrate or the container, or at a specific area. The solid copper may be thin enough to transmit a sufficient amount of light for detection. It may be configured that a place where the solid copper is contacted with the sample and a place where the fluorescence emitted from the sample is measured are separated, and it also provides a sample transport means capable of transporting the sample between the two places. Herein, the place where the fluorescence emitted from the sample is measured refers to a place where the fluorescence emitted from the sample is measured by irradiating the sample with light.

An amount of the copper contacted with the sample is not especially limited as long as the fluorescence is detected from the sample in the detection step. When the solid copper is used, an amount of the solid matter containing copper is set as appropriate depending on an area where the sample is contacted with the solid matter, a proportion of the area to a volume of the sample, a shape of the container holding the sample, the concentration of copper contained in the solid matter, types or amounts of contaminants other than copper and the like. For example, when copper powder used in Examples is used, the amount of the copper powder is preferably 37.5 mg or more per ml of the sample. Also, for example, when a thin film of the solid copper is formed on a surface (inner surface) of the substrate or the container and the sample is held in a space having a depth of about 20 micrometers sandwiched between two glass plates (see Examples), copper is sputtered on at least a surface of the space to a thickness of 20 nanometers or more.

(2) Sample

As the sample containing nucleic acids, any samples capable of containing the nucleic acids such as DNAs and RNAs may be used. For example, a nucleic acid extraction solution, a solution containing a nucleic acid compound, a reaction product of a nucleic acid amplification such as PCR, an electrophoresis sample and the like may be possible. Alternatively, as the sample, not only the nucleic acid solution sample, but cells themselves, tissue slices including cells, etc. can be used.

(3) Reaction Solution

The sample is preferably contacted with copper in a reaction solution containing a salt. The types of the salt is not especially limited as long as the advantages of the present technology cannot be lost, and known salts can be freely selected and used. For example, one or more of sodium chloride (NaCl), potassium chloride (KCl), magnesium chloride ($MgCl_2$) etc. can be freely selected and used (see Examples).

The concentration of the salt is not especially limited and can be freely set as long as the advantages of the present technology are not lost. Preferably, the concentration of the salt is set to 0.025 M or more (see Examples).

Preferably, the reaction solution contains no component such as a chelating agent (for example, EDTA, Tris etc.) for stabilizing copper (II) ions.

(4) Contact Conditions

A contact time of the sample with copper is not especially limited, and can be freely set depending on the sample used or the configuration of copper. For example, when a liquid sample and copper powder are used, they are fully agitated, thereby decreasing the contact time. When the substrate or the container having the thin film of the solid matter containing copper is used, the contact time can be decreased by changing the structure of the substrate or the container to increase a contact area of the sample with copper. In addition, when the sample is contacted with copper, the contact area and the contact time of a reaction solution and air containing oxygen are desirably limited as small or short as possible.

2. Detection Step

In the detection step, the fluorescence emitted from the sample after the contact step is detected.

(1) Light Irradiation

Light (excitation light) irradiating to the sample in order to detect fluorescence from the sample is not especially limited as long as the fluorescence emitted from the sample can be detected after the sample containing the nucleic acids is contacted with copper.

As a light source of the excitation light, a mercury lamp, a halogen lamp, a xenon lamp, a laser, an LED, sunlight and the like can be used, for example. It is also possible that a wavelength selecting means for selecting a desirable wavelength is disposed between the light source and the sample. In this case, the wavelength selecting means includes an optical filter, a prism, a grating mirror and the like. Alternatively, an energy transfer such as FRET and BRET from adjacent molecules may be substituted with light irradiation as long as the fluorescence emitted from the sample can be detected.

The excitation light includes light preferably having a wavelength of about 300 to 420 μm, more preferably having a wavelength of about 330 to 380 μm in order to generate efficiently fluorescence from the sample. In addition, in the excitation light, an intensity of light having a wavelength of about 420 μm is preferably sufficiently low, and an intensity of light having a wavelength of about 500 nm or more is more preferably sufficiently low so as not to inhibit the detection of fluorescence.

Preferably, the intensity of the excitation light is high enough to detect the fluorescence emitted from the sample. It is preferable that the intensity of the light for detection be set depending on the wavelength range of the irradiation light; a size, base sequences, a higher order structure, an amount and a concentration of the nucleic acids to be detected; a signal amount to be acquired; the wavelength range of the light to be detected; a sensitivity, a type and a configuration of a detector; and the like, as appropriate. In order to adjust the intensity of the excitation light, a type of the light source, an intensity of the light emitted from the light source, a configuration of a light collecting means such as a lens, a type and a configuration of the wavelength selecting means, a configuration of an optical system for irradiating light including a light intensity adjusting means such as an ND filter and a diaphragm, a density, an irradiation range and an irradiation time of the light for irradiation may be adjusted appropriately, for example.

A light travel means such as an optical fiber and a mirror may be disposed between the light source of the excitation light and the sample. The container holding the sample used in the light irradiation is not especially limited, but preferably has a material and a structure that transmit a sufficient amount of light irradiated and fluorescence to be detected.

(2) Detection of Fluorescence

The fluorescence emitted from the sample can be detected by any non-limiting means such as a conventionally known means. As the detection means, an element for converting a light signal into an electric signal such as a photo detector, a photo diode, a photomultiplier, a CCD camera, and a CMOS camera is used. Alternatively, as the detecting means, capturing as a film, or an observation with bare eyes may be utilized. The fluorescence emitted from the sample can be indirectly detected by inducing the energy transfer such as FRET to fluorescent molecules adjacent to the sample, and receiving the fluorescence emitted from the fluorescent molecules.

In order to detect the fluorescence emitted from the sample efficiently, the light collecting means such as the lens is preferably disposed between the sample and the detection means. The light travel means such as the optical fiber and the mirror may be disposed between the sample and the detection means.

The fluorescence may be detected on the sample at a same side or at a different side of the light irradiation. In particular, when the fluorescence is detected at the same side of the light irradiation, a light reflection means such as a mirror surface is disposed in a different direction, thereby improving collection efficiencies of the fluorescence emitted from the sample. Even when the fluorescence is detected at the different side of the light irradiation, the light reflection means may be disposed and have a configuration so as not to inhibit the light detection, or the light reflection means such as a dichroic mirror having a wavelength selectivity that transmits the light having the irradiation wavelength and reflects the light to be detected may be disposed.

When the fluorescence emitted from the sample is detected, there may be light other than the light to be detected including scattered light of the light irradiated to the sample, the autofluorescence from the sample or the container holding the sample, and leaked light from outside. In this case, the light selecting means is preferably disposed between the sample and the light detection means so as not to arrive at the light other than the light to be detected at the detection means.

Examples of the light selecting means include the optical filter, the prism, the grating mirror and the like. Also, an area, where the light is transmitted upon the fluorescence detection, of an outer or inner surface of the substrate and the container into which the sample is introduced may be treated in advance so that only the light having a desirable wavelength is transmitted without any effect upon the light irradiation.

The light selecting means can detect only the fluorescence preferably having a wavelength of about 420 nm or more, more preferably having a wavelength of about 500 nm or more based on the results in Examples as described later. In addition, in order to minimize the effect of the autofluorescence as low as possible, only the wavelength of about 600 nm or more can be detected, as necessary. In the method of detecting nucleic acids according to the present technology, there is provided the fluorescence having a relatively long wavelength such as a center wavelength of about 600 nm to an ultraviolet ray excitation wavelength of about 360 nm and having a long stroke shift. Accordingly, the method of detecting nucleic acids according to the present technology has an advantage that the autofluorescence emitted from the scattered light or other substances less affects the detection of the intended fluorescence.

As another light selecting means, a time to detect the fluorescence after the light irradiation is set appropriately utilizing the property that fluorescence lives are different with the variety of molecules, the light other than the light to be detected is excluded as much as possible, and the fluorescence needed is detected.

(3) Fluorescent Spectrum Detection

A spectrum (an excitation spectrum or an emission spectrum) of the fluorescence emitted from the sample is measured by a means suitable for the spectrum measurement in the light irradiation and the fluorescence detection.

The excitation spectrum is measured by spatially or temporally changing the wavelength of the light irradiated to the sample to measure a spatial or temporal change of a fluorescence intensity to be detected using the light selecting means such as the optical filter, the prism, the grating mirror and the like. The emission (fluorescent) spectrum is measured by spatially or temporally changing the wavelength of the light irradiated to the sample and by introducing the light into the detection means to measure a spatial or temporal change of a fluorescence intensity to be detected. By combining them, both of the excitation spectrum and the emission spectrum can be measured.

A specific example of the wavelength selecting means for spatially changing the wavelength of the light irradiated to the sample or the fluorescence emitted from the sample is an optical device such as the prism and the grating mirror that changes the direction of the light travel depending on the wavelength.

Specific examples of the wavelength selecting means for temporally changing the wavelength of the light irradiated to the sample or the fluorescence emitted from the sample include replacing the optical filter with a different type of the optical filter, and changing the wavelength of the transmitted light by the optical filter capable of controlling the wavelength of the transmitted light. Alternatively, the optical device such as the prism and the grating mirror that changes the direction of the light travel depending on the wavelength, and a light direction selecting means capable of selecting only the light traveling a specific direction of the light transmitted through the optical device may be disposed. A location or a configuration of the optical device and/or the light direction selecting means may be temporally controlled and changed. These means can be electrically controlled to change by time a wavelength of light automatically selected, for example, using a computer. The light direction selecting means may be configured by combining the optical devices such as a slit, a lens, a mirror and an optical fiber, as appropriate.

The method of detecting the excitation spectrum and/or the emission spectrum by temporally changing the wavelength of the light with the wavelength selecting means preferably includes controlling the wavelength of the light selected by the wavelength selecting means using a computer, reading a measurement result into the computer using a device for converting a light signal into an electrical signal such as a photo detector as the light detection means, and recording the wavelength of the light irradiated and the fluorescence intensity measured by correlating each other.

In the method of detecting the excitation spectrum and/or the emission spectrum by spatially changing the wavelength of the light with the wavelength selecting means, light receiving elements are arrange in an array in one dimension, or light receiving elements such as a CCD and a CMOS are disposed on a plane, as the light detection means.

(4) Detection of Fluorescence Space Distribution

For obtaining information about the spatial distribution and the shape of the nucleic acids contained in the sample, one way to provide the spatial information at a time may be to conduct the light irradiation and the fluorescence detection all at once on the area where the nucleic acids spread to some extent. Alternatively, another way to provide the spatial information may be to change the sites to be detected by time and to sequentially scan the inside of the area where the nucleic acids spread to some extent.

In the former case, a whole area to be detected is preferably irradiated with the light, and the intensity of the light irradiating the whole area is more preferably uniform.

As the light detection means, an observation using a film or bare eyes can be utilized. Also, the light detection means such as the CCD camera and the CMOS camera including the light receiving elements two-dimensionally disposed for converting a light signal into an electrical signal can be used.

One example of the latter case is to use a laser light for irradiation, change the irradiation position of the laser light using a galvanic mirror etc. by time, detect the fluorescence emitted from the irradiation position of the laser, and acquire the spatial distribution of the fluorescence intensity from the data to connect the irradiation position of the laser with the fluorescence intensity detected. In this case, the spatial distribution of the fluorescence intensity is preferably analyzed automatically by controlling the light irradiation position using the galvanic mirror, recording the light irradiation position by a computer, and constructing the data to correlate the fluorescence intensity detected with the light irradiation position at the time within the computer.

Another way to acquire the information about the spatial distribution is to measure a one-dimensional distribution of the fluorescence using a light source for linearly light irradiation and the light detection means including the light receiving elements one-dimensionally disposed such as line sensors, and to sequentially move the position thereof. Alternatively, the spatial distribution of the fluorescence intensity in a wider area can be acquired by using the light receiving elements such as the CCD camera and the CMOS camera that can acquire the spatial distribution of the fluorescence intensity at a time and sequentially moving a spatial area to be observed. In these cases, it is also desirable that the area to be detected is controlled and the result of the fluorescence detection is recorded using a computer as appropriate, and the spatial distribution of the fluorescence intensity is automatically analyzed based on the information.

3. Base Sequence Analysis

Next, a method of analyzing the base sequences of the nucleic acids and the mismatch in the double strand formed by the nucleic acids based on the information about the fluorescence detected in the detection step.

Specific examples of the information about the fluorescence include the fluorescence intensity and/or spectrum (the excitation spectrum or the emission spectrum), a fluorescence life, and the spatial distribution and the time change of the fluorescence. The information can be converted into numerals, recorded on the computer or computed on the computer for analysis.

The fluorescence intensity acquired in the detection means depends on the reaction conditions, the optical system, and the concentration, the type, the size, the higher order structure and the base sequences of the nucleic acids (see Examples). In particular, when the reaction conditions, the whole optical system, and the type, the size, the higher order structure and the base sequences of the nucleic acids are constant, the information about the concentration of the nucleic acids can be provided by the measurement result of the fluorescence intensity. In this case, the method of analyzing includes the steps of providing the information about the relationship between the known concentration of the nucleic acids to be detected and the fluorescence intensity, measuring the fluorescence intensity to desirably two or more of the concentrations of the nucleic acids, creating a calibration curve, applying the fluorescence intensity provided by the detection to the relationship between the concentration and the intensity, and calculating the concentration of the nucleic acids. The method may also be performed automatically by recording the relationship between the concentration of the nucleic acids and the fluorescence intensity in advance, and calculating the concentration of the nucleic acids from the fluorescence intensity on the computer.

In addition, the spectrum and the fluorescence intensity acquired in the detection step depend on the base sequences and the higher order structure of the nucleic acids as long as, in particular, the concentration, the reaction conditions and the higher order structure are constant (see Examples). The "higher order structure" herein refers to a single-stranded structure or a double-stranded structure of nucleic acids, and involves a double strand formation by hybridization or no double strand formation and its site, and a mismatch or no mismatch in the double strand and its site. The properties can be utilized to provide the information about the base sequences and the higher order structure of the nucleic acids from the measurement result of the fluorescent spectrum and the intensity. More specifically, when it is known that the sequence and the higher order structure of the nucleic acids contained in the sample are any one of finite numbers of known candidates, the sequence and the higher order structure of the nucleic acids contained in the sample to be fluorescent detected can be estimated by measuring the fluorescent spectrum and the intensity of each candidate in advance, and comparing with the measurement result. A method of comparing two or more spectra includes calculating feature values, e.g., the maximum excitation wavelength and the fluorescence intensity, a ratio of the fluorescence intensities in two or more wavelength areas, and comparing them. In addition, a difference between the two spectra to be compared can be calculated to quantify the similarity. Alternatively, when the spectra are compared only by focusing on their shapes, the comparison can be made by correcting the maximum intensities of the spectra measured to be a uniform value. Furthermore, the fluorescence intensities are multiplied by a variable and a least square approach is utilized, a variable value where the difference between the two spectra becomes minimum and the magnitude of the difference between the two spectra at that point can be quantified. These operations can be automatically by recording the relationship between the sequence and the higher order structure of the nucleic acids and the spectrum and the fluorescence intensity on the computer in advance, and estimating on the computer the sequence and the higher order structure of the nucleic acids from the information about the spectrum and the fluorescence intensity measured.

When the spatial distribution and the time change of the fluorescence acquired in the detection step are analyzed, the space may be visually inspected, observed for its characteristic, and classified qualitatively. Alternatively, a fluorescent image may be input into the computer, and may be analyzed quantitatively by an image processing. As an example of the image processing, the areas emitting the fluorescence are extracted by, for example, a binary coded process, and numerical values such as an area, an outline length, a circularity degree, a center or gravity center position, a total sum, an average value, a mean value, a median value, dispersion and a standard deviation of the fluorescence intensities in the area can be calculated. Alternatively, a pattern matching, a learning algorithm and the like can be applied to identification of the area having the specific shape or to classify the shape.

4. Applications

The method of detecting the nucleic acids according to the present technology can be utilized in various fields by combining the above-described contact step and the fluorescent step with analysis of the base sequences, as necessary. Hereinafter, applications of the method of detecting the nucleic acids according to the present technology will be described.

(1) Detection of Difference in Fine Gene Sequences

According to the present technology, it is possible to provide the information about the base sequences of the nucleic acids contained in the sample by measuring the fluorescent spectrum and/or the intensity. However, when the sample contains a number of nucleic acids, the fluorescent spectrum and/or the intensity to be detected are averaged and there may be a possibility that the difference between fine gene sequences cannot be identified. It is therefore preferable that methods of limiting the range of the nucleic acids to be detected be combined as described below, as necessary.

Examples of the difference between fine gene sequences include single nucleotide polymorphisms (SNPs). It is known that analysis of the basic sequence of the nucleic acids is very useful for diagnosis of disease. It is a common knowledge that a risk to various diseases including a cardiac disease can be evaluated by analyzing the SNPs.

A first example of a method of limiting the range of the nucleic acids to be detected includes a method of taking out only a part containing the sequences to be analyzed from the nucleic acids contained in the sample. Specifically, the methods include hybridization using probe DNAs immobilized on a substrate or beads, electrophoresis, PCR for amplifying the sequences to be analyzed using a nucleic acid amplification technique, and the like. In addition, a restriction enzyme reaction and a ligation reaction may be combined with these methods.

A second example includes a method of selectively acquiring signals from only the specific bases of the nucleic acids contained in the sample. Specifically, a phenomenon that very strong fluorescence is detected in a thymine (T) sequence having no complementary strand is utilized, which is found in the present technology. In this method, one or more probe nucleic acids that are hybridized with the sequences excluding sites to be detected for mutation in the nucleic acids contained in the sample to form double-stranded nucleic acids are prepared in advance. The probe nucleic acids are hybridized with the nucleic acids to be detected for mutation in the gene sequence to provide a sample. In the probe nucleic acids, when the mutation is produced, e.g., adenine (A) in the sequences to be analyzed is replaced with other base, T will be disposed in the sequences of the probes corresponding to the site. In this way, when the base in the site is replaced with any base other than A, a mismatch of T is produced, whereby strong fluorescence is measured. Alternatively, when the mutation is produced, e.g., T in the sequence to be analyzed is replaced with other base, the base other than A will be disposed in the sequence of the probes corresponding to the site. In this way, when there is no mutation, strong fluorescence is measured from T without forming the double strand.

The probe nucleic acids can be configured by DNAs, RNAs, peptide nucleic acids (PNAs), phosphorothioate type oligonucleotide, BNAs (LNAs) and the like.

A third example includes a method of limiting a physical area to be light irradiated or to be detected for fluorescence in the detection step. For example, near-filed light such as evanescent light is used for irradiating the sample, i.e., light is irradiated to only an especially limited specific area. The method can be combined with a means for holding or moving the nucleic acids at a specific position. By the means for holding or moving the nucleic acids at the specific position, the nucleic acids are immobilized on a solid surface, pass through very fine flow channels such as nanopores, or move in a protein such as an enzyme.

As other method of limiting a physical area to be light irradiated or to be detected for fluorescence, an energy transfer such as FRET and BRET may be utilized. In the light irradiation, molecules for inducing the FRET and BRET are disposed adjacent to the area to be detected, and the energy transfer from the molecules is utilized for local light irradiation. In the fluorescence detection, fluorescent molecules for inducing the FRET by receiving fluorescence energy from the sample are disposed adjacent to the area to be detected, and the fluorescence generated from the fluorescence molecules is detected to be utilized for a local fluorescence detection.

(2) Analysis of Methylation of DNA Molecules

It is known that cytosine (C) in DNA molecules is methylated in genomes within cells. Presence or absence of methylation of cytosine (C) can be found by determining that whether or not cytosine (C) is replaced with uracil (U). In other words, when the nucleic acids are treated with bisulfite under adequate conditions, only cytosine (C) not methylated can be selectively converted into uracil (U). Thus, when uracil (U) is detected, presence of non-methylated cytosine can be detected.

The fluorescence derived from the composite of the nucleic acid and copper is high in uracil and thymine, but is not detected in cytosine and methylated cytosine (see Examples). Therefore, non-methylated cytosine contained in the sample is selectively converted into uracil by the bisulfate treatment, and the fluorescence intensity and/or the spectrum change amount detected in the sample are determined, thereby analyzing presence or absence of the methylation or demethylation and its amount of cytosine in the nucleic acids. By using the method described in the "Detection of Difference in Fine Gene Sequences" as described above in combination, the position of methylated cytosine or demethylated cytosine etc. in the base sequences of the nucleic acids can be analyzed in detail.

The analysis of methylation can be made as follows: Firstly, the sample containing the nucleic acids is treated with bisulfate in accordance with the conventionally known techniques. Next, the intensities and/or spectra of the fluorescence are detected from the sample before the bisulfate treatment and the sample after the bisulfate treatment. Then, the intensities and/or spectra of the fluorescence detected from the samples before and after the bisulfate treatment are compared. The more the amount of cytosine not methylated is, the more the amount of uracil produced by the bisulfate treatment is. By comparing the fluorescence of the samples before and after the bisulfate treatment, information about presence or absence of the methylation or demethylation and its amount of cytosine in the nucleic acids can be provided.

When a large amount of thymine is contained in the base sequences in the nucleic acids contained in the sample, the fluorescence derived from thymine becomes a noise and a signal/noise ratio of fluorescence from uracil may be decreased. In addition, a plurality of non-methylated cytosine that is converted into uracil by the bisulfate treatment may exist in the base sequences of the nucleic acids. In this case, the methylation of the base sequences of the nucleic acids at the specific area is effectively analyzed by the following methods in combination.

Firstly, the nucleic acids contained in the sample after the bisulfate treatment are amplified or concentrated at the area to be analyzed for the methylation. Specifically, the nucleic acid amplification such as PCR and a nucleic acid concentrating method utilizing a nucleic acid hybridization reaction are used.

Secondly, fluorescence generated from other areas than the area to be analyzed for the methylation is inhibited. The fluorescence derived from the composite of the nucleic acids and copper has high intensity in thymine within single-stranded DNAs, and is significantly inhibited in thymine within double-stranded DNAs (see Examples). Therefore, nucleic acid chains for a mask having complementary base sequences to the area outside the analysis are hybridized and the fluorescence from thymine in the area outside the analysis is inhibited, whereby it is possible to effectively detect the fluorescence from the area to be analyzed. Alternatively, a quencher may be used to inhibit the fluorescent generated from the area outside the analysis. The fluorescence derived from the composite of the nucleic acids and copper may be inhibited by disposing the quencher adjacent to the composite (see Examples). Accordingly, by disposing the quencher on the area outside the analysis, it is possible to detect the fluorescence from the area to be analyzed with high efficiency.

Thirdly, only the area to be analyzed for the methylation is selectively excited, or only the fluorescence from the area is selectively detected. Specifically, donor probes that can excite the composite of the nucleic acids and copper to generate the fluorescence is disposed adjacent to the area to be analyzed, and the energy transfer by FRET, BRET or the like is utilized to selectively excite only the area to be analyzed. In this way, only the fluorescence can be detected from the area to be analyzed. Alternatively, acceptor probes that are excited by the energy transfer of the fluorescence from the composite of the nucleic acids and copper and emit fluorescence having a different wavelength may be disposed adjacent to the area to be analyzed, and the fluorescence may be detected from the area to be analyzed by the detection of fluorescence by the acceptor probes. The methods as described above can be used in any combination.

(3) Observation and Measurement of Cell Nuclei

The method of detecting nucleic acids according to the present technology is applied to a sample containing nucleated cells to detect a spatial distribution of the nucleic acids. The distribution and the shape thereof are analyzed to provide information about a distribution, a position, a number, a size, a shape or the like of cell nuclei in the tissue slices or the cells.

From the information, the number of the nucleated cells can be calculated. An internal shape of the container into which the sample is introduced is designed adequately to hold a constant volume of the sample within a constant area, which can be used for measuring the concentration of the nucleated cells contained in the sample. In addition, when the shapes and the numbers of the cell nuclei are measured together, a plurality type of cells including different shapes of cell nuclei can be identified or counted. For example, it is known that leucocyte has different shapes of nuclei depending on granulated leukocyte, monocyte, and lymphocyte. The method of detecting nucleic acids according to the present technology can be utilized to identify or count the types of the leucocyte.

As types of malaria parasite known as a parasite that causes malaria, tropical malaria parasite, vivax malaria parasite, quartan malarial parasite, ovale malaria parasite and the like are known. In addition, as the stage, a ring form, trophozoite, schizont, a gametrocyte and the like are known. It is very important that these types are identified adequately in order to adequately plan the therapeutic strategy of the infectious patient. For identifying the types of the malaria parasites, the shapes of the nuclei are conventionally observed by Giemsa stain in principle, although there is a simple method of detecting a gene or an antigen. However, in this method, there is a problem that may cause a diagnostic error when the stain is insufficient. In contrast, once the method of detecting nucleic acids according to the present technology is applied to identification of the types of the malaria parasites, no conventional dying reagent is required. Accordingly, malaria etc. can be diagnosed by a simpler method with certainty with a simple dyeing and without requiring cleaning.

(4) Analysis of Fine Particles

When nucleic acids contained or immobilized in fine particles such as cells and beads contained in a liquid sample are detected, the particles may be at rest, or may be flowed in micro flow channels. For example, the liquid sample is introduced into a flow cell together with a sheath flow, and is sandwiched by the sheath flows to form a laminar flow. The fluorescence generated by the particles flowing through the flow cell can be detected. The flow cell may have any configuration that is widely studied, developed and used practically as a flow cytometry technique.

(5) Application to Lab-on-Chip

The method of detecting nucleic acids according to the present technology can be incorporated into the lab-on-chip for treating or detecting the sample in the container such as a micro-flow channel chip. In this case, a step of pre-treating the sample is introduced and combined within the container depending on the intended usage for further convenience.

The step of pre-treating the sample for detection and sequence analysis of nucleic acids includes, for example, extracting, separating and amplifying the nucleic acids. More specific examples include a separation by electrophoresis, a gel filtration column or an absorption column; amplification by the PCR reaction; and the like. These means can be incorporated into the microchip by the known technologies.

Alternatively, as the step of pre-treating the sample for observation, detection and analysis of the nuclei contained in the cells, the specific cells can be selected or concentrated. As the step of selecting or concentrating the specific cells can utilize different properties depending on the types of the cells, e.g., a size, a specific gravity, a toughness, a binding force to a specific substance such as antibodies, etc. As an example, the antibodies that specifically bind to the cells to be observed or the cells not to be observed is mobilized to the inner surface of the container or the beads. By utilizing binding or not binding to the antibodies, the cells can be selected or concentrated. Also, fine particles of a magnetic substance to which the antibodies are immobilized are prepared. Using magnetism, it is possible that only the cells to which the magnetic substance is bound, or only the cells to which the magnetic substance is not bound are selected. Furthermore, the sample is exposed to an adequate changing osmotic pressure, acid or alkali, whereby only erythrocyte can be broken and removed to select only leucocyte. As another example, when the malaria parasite is, for example, observed in a human blood, it is conventionally known that a magnetic substance called "haemozoin" is formed in the erythrocyte that the malaria parasite is infected. The erythrocyte can be separated or concentrated by magnetism. By combining the method with the method of detecting the nucleic acids according to the present technology, it is possible to easily observe the malaria parasite with certainty.

<B> Fluorescent Pigment

Next, the fluorescent substance according to the present technology will be specifically described.

Pigments emitting fluorescence having a variety of colors, e.g., fluorescein and phycoerythrin, are utilized in order to observe and analyze a cell, a tissue, a biomolecule for use of a fluorescence microscope, a flow cytometer, a gene amplification reaction, a gene sequencing reaction, quantitative determination of biomolecules including a protein, measurement of binding ability between biomolecules including a protein. These fluorescent pigments are used as a tool for providing information about localization of the biomolecules to which the pigment is bonded, and for providing information about a location and an amount of the molecules of interest that are identified by antibodies or nucleic acid probes, for example, by binding the pigment to the antibodies or the nucleic acid probes. When a number of pigments having different colors is prepared, more molecules of interest can be analyzed.

Using the technology of the method of detecting nucleic acids according to the present technology as described above, fluorescent substances having a variety of spectrum can be formed. In other words, the composite of the nucleic acids and copper emits the fluorescence having a different spectrum or intensity depending on the base sequences and the length of the nucleic acids. By utilizing the properties of the composite of the nucleic acids and copper, the composite can be used as the fluorescent substance emitting a variety of spectra, and can be used as a fluorescent pigment that is labeled to antibodies, for example.

The present technology may have the following configurations.

(1) A method of detecting nucleic acids including the steps of:

bringing a sample containing the nucleic acids into contact with copper, and detecting fluorescence emitted from the sample.

(2) The detection method according to (1) above, in which base sequences of the nucleic acids are analyzed based on an intensity and/or a spectrum of the fluorescence detected in the detection step.

(3) The detection method according to (1) above, in which a mismatch in a double strand formed by the nucleic acids is analyzed based on an intensity and/or a spectrum of the fluorescence detected in the detection step.

(4) The detection method according to (1) above, including steps of:

treating the sample with bisulfate, in which methylation of cytosine in the nucleic acids is analyzed based on a difference between an intensity and/or a spectrum of the fluorescence detected from the sample before the bisulfate treatment and an intensity and/or a spectrum of the fluorescence detected from the sample after the bisulfate treatment in the detection step.

(5) The detection method according to any of (1) to (4) above, in which the copper is solid copper.

(6) The detection method according to any of (1) to (5) above, in which the contact step is a step of bringing the sample with into contact copper under coexistence of a salt.

(7) The detection method according to any of (1) to (6) above, in which the detection step is a step of detecting fluorescence emitted from the sample by irradiating the sample with light having a wavelength of 300 to 420 μm.

Example 1

Example 1 illustrates that orange-colored fluorescence was emitted by ultraviolet irradiation under certain conditions when nucleic acids are mixed with a solution including Cu(I) ions generated by reducing Cu(II) ions with an ascorbic acid.

<Material and Method>

Cu: a $CuSO_4$ solution and (+)-Sodium L-ascorbate (hereinafter referred to as "S.A.") were purchased from Sigma-Aldrich.

Nucleic acid: Sonicated Salmon Sperm DNA (hereinafter referred to as "ssDNA") purchased from BioDynamics laboratory Inc. (Tokyo, Japan) was used. In addition, as oligo-DNAs, Custom Oligo purchased from Invitrogen Corporation was used.

Buffer: HEPPSO purchased from DOJINDO Laboratories (Kumamoto, Japan) was used by adjusting the pH to 8.5 pursuant to the protocols provided by the manufacturer.

Fluorophotometer: NanoDrop 3300 (Thermo Fisher Scientific, Inc., Waltham, Mass., USA) or type F-4500 spectrofluorophotometer (Hitachi High-Technologies Corporation) was used. In the NanoDrop 3300, a UV LED light source was used to provide exciting light. A fluorescent spectrum excited by the exciting light was measured. Using a companion software, Relative Fluorescence Units (RFU) at a wavelength where a spectrum intensity became at maximum was acquired as a peak RFU value. In the type F-4500 spectrofluorophotometer, a quartz capillary and a dedicated adapter cell manufactured by Helix Biomedical Accessories, Inc. were used. Unless otherwise noted below, the NanoDrop 3300 was used.

Spectrophotometer: NanoDrop 1000 Spectrophotometer was used to measure an absorption spectrum.

Sample preparation and fluorescence measurement: 50 mM of a HEPPSO buffer was mixed with sodium chloride (250 mM), $CuSO_4$ (0 to 4 mM), S.A. (4, 50 mM), ssDNAs (1 mg/ml) or oligo-DNAs (50, 250, 500 µM) to provide 20 µl of a sample. It is known that the S.A. has an action to reduce Cu(II) ions generated from $CuSO_4$ in the solution to Cu(I) (see Non-Patent Document 31).

<Results>

Figure 2:
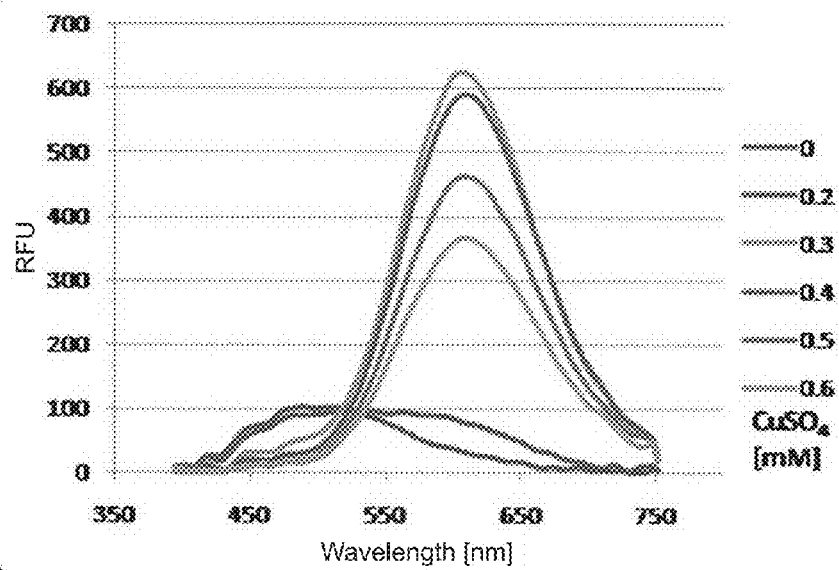
FIG. 2 Graphs each substituting a drawing and showing fluorescent spectra and an RFU value obtained by bringing ssDNAs into contact with $CuSO_4$ having a varied concentration under the condition of an S.A. concentration of 50 mM; (A) shows the fluorescent spectra and (B) shows a peak RFU value (Example 1).
Figure 2:
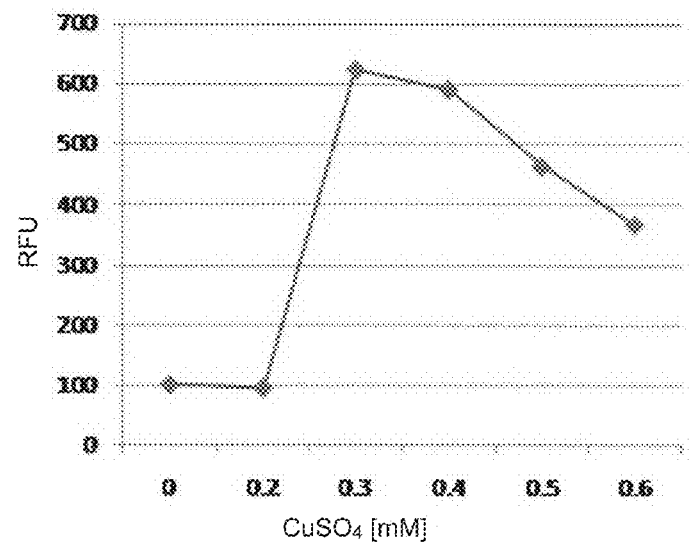

FIGS. 1 and 2 are graphs each showing a fluorescent spectrum and an RFU value obtained by changing a concentration of $CuSO_4$ under the condition of an S.A. concentration of 50 mM; (A) shows the fluorescent spectrum and (B) shows a peak RFU value.

Figure 3:
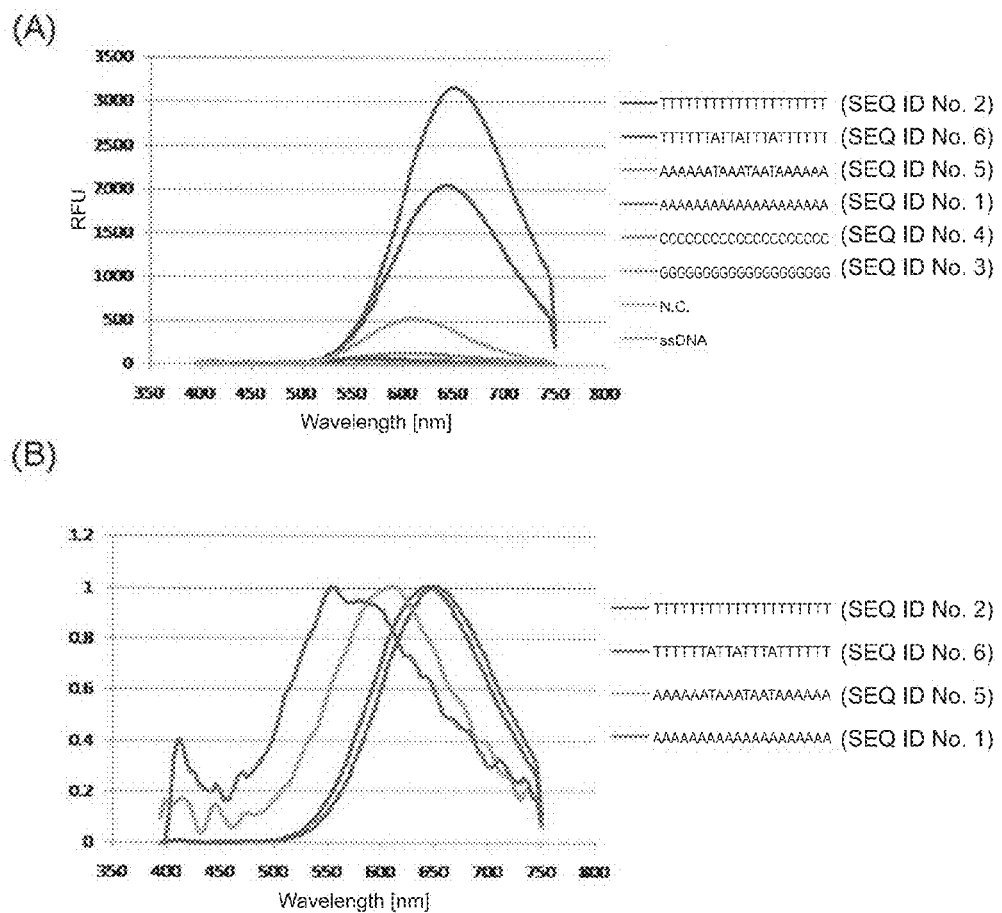
FIG. 3 Graphs each substituting a drawing and showing fluorescent spectra and RFU values obtained by bringing oligo-DNAs into contact with $CuSO_4$ having a concentration of 0.4 mM under the condition of an S.A. concentration of 4 mM (Example 1).
Figure 4:
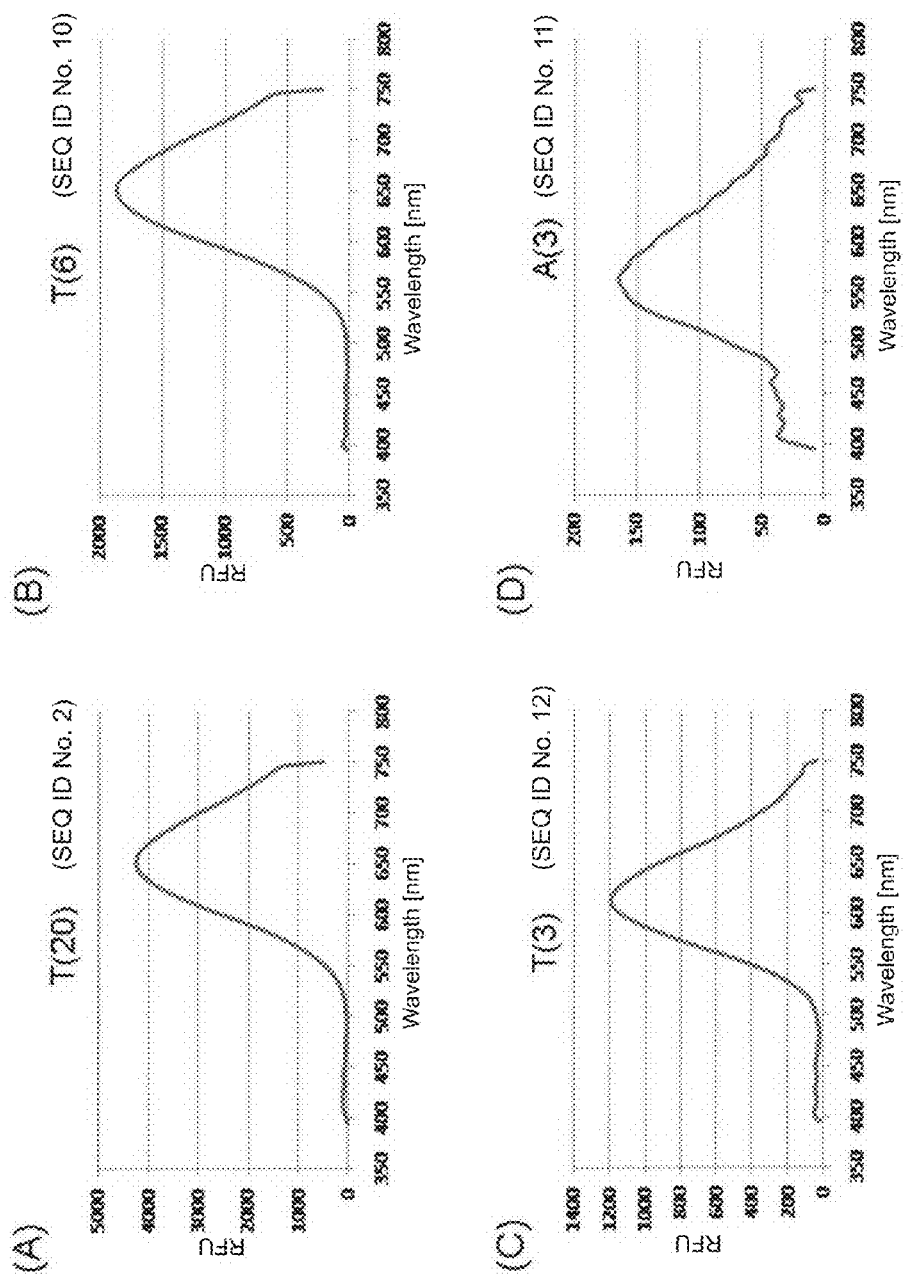
FIG. 4 Graphs each substituting a drawing and showing a fluorescent spectrum and an RFU value obtained by bringing oligo-DNAs into contact with $CuSO_4$ having a concentration of 0.4 mM under the condition of an S.A. concentration of 4 mM (Example 1).

FIGS. 3 and 4 are graphs each showing fluorescent spectra obtained under the conditions of $CuSO_4$ having a concentration of 0.4 mM and an S.A. concentration of 4 mM. The oligo-DNAs having base lengths of 20, 10, 6 and 3 had a concentration of 50, 50, 250, and 500M, respectively. FIG. 3 shows a result of the oligo DNAs having the base sequences described in SEQ ID NOS: 1 to 6. An abscissa axis represents a wavelength, an ordinate axis in (A) represents the RFU value in each wavelength, and an ordinate axis in (B) represents a value provided by dividing the RFU value in each wavelength by a maximum RFU value. FIG. 4 shows a result (A) of the oligo-DNAs having the base sequences described in SEQ ID NO: 2 (hereinafter described as T(20)), a result (B) of the oligo-DNAs having the base sequences described in SEQ ID NO: 10 (hereinafter described as T(6)), a result (C) of the oligo-DNAs having the base sequences described in SEQ ID NO: 12 (hereinafter described as T(3)), and a result (D) of the oligo-DNAs having the base sequences described in SEQ ID NO: 11 (hereinafter described as T(3)). Each abscissa axis represents a wavelength, and each ordinate axis represents an RFU value in each wavelength.

As shown in the Figures, it was confirmed that the patterns of the fluorescent spectra (a peak wavelength and an intensity) were changed depending on the base sequences of the nucleic acids.

Figure 5:
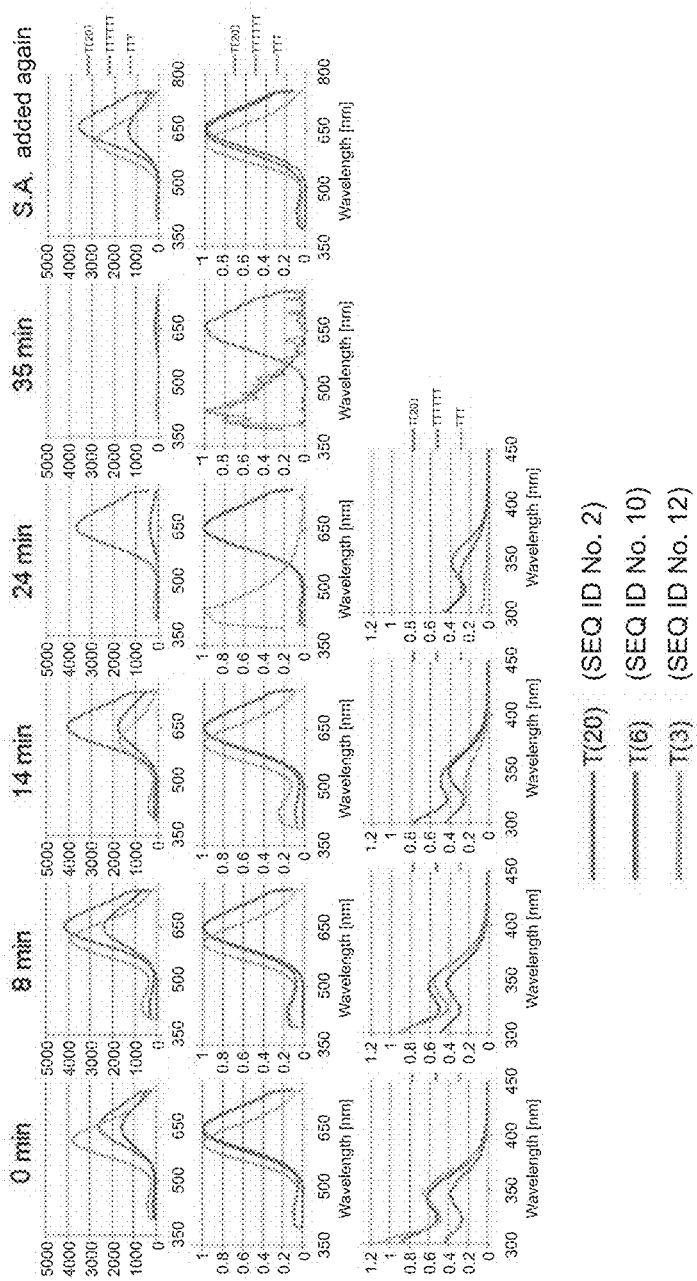
FIG. 5 Graphs each substituting a drawing and showing a change with elapsed time of a fluorescent spectrum and absorption spectra obtained in oligo-DNAs T(20), T(6) and T(3) under the condition of a $CuSO_4$ concentration of 0.4 mM and an S.A. concentration of 4 mM (Example 1); the upper graphs each show the fluorescent spectra with an ordinate axis of an RFU value (absolute value), the middle graphs each show the fluorescent spectra with an ordinate axis of an RFU value (relative value) and the lower graphs each show the absorption spectra.
Figure 6:
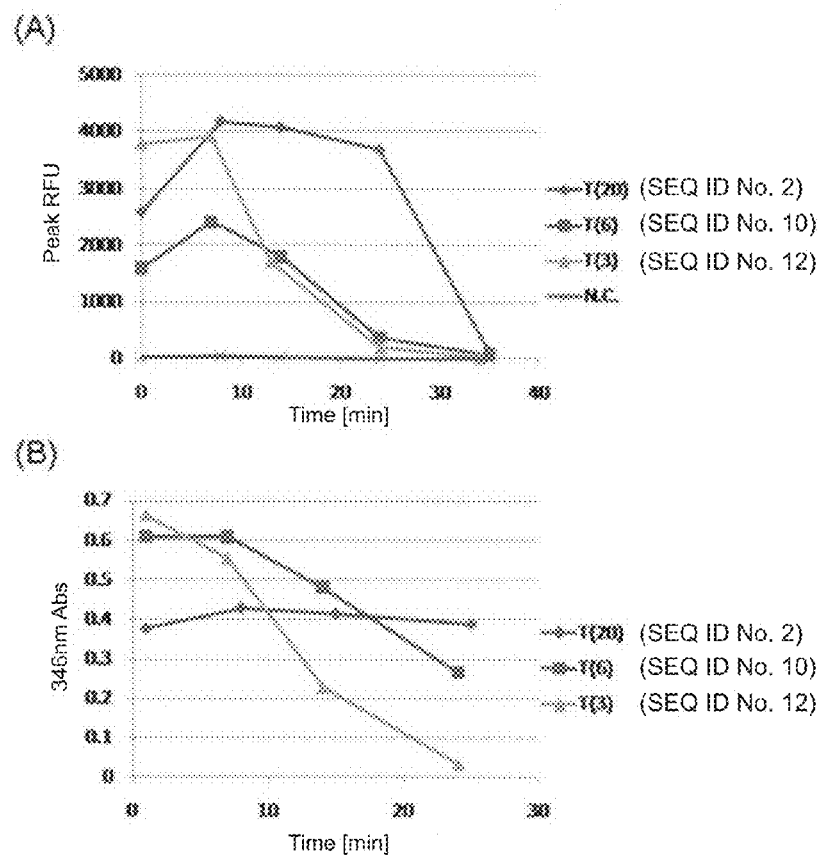
FIG. 6 Graphs each substituting a drawing and showing a change with elapsed time of fluorescent spectra and absorption spectra obtained in oligo-DNAs T(20), T(6) and T(3) under the condition of a $CuSO_4$ concentration of 0.4 mM and an S.A. concentration of 4 mM (Example 1); (A) shows a change with elapsed time of the peak RFU value, and (B) shows a change with elapsed time at a wavelength of 346 nm.

Next, a change with elapsed time of fluorescent spectra and absorption spectra obtained in oligo-DNAs T(20), T(6) and T(3) under the condition of a $CuSO_4$ concentration of 0.4 mM and an S.A. concentration of 4 mM. The S.A. was added directly before the measurements of the fluorescent spectrum and the absorption spectra for the first time. After 8, 14, 24 and 35 minutes, the fluorescent spectra and the absorption spectra were measured. The results are shown in FIGS. 5 and 6. In FIG. 5, the upper graphs each show the fluorescent spectrum with an ordinate axis of an RFU value (absolute value), the middle graphs each show the fluorescent spectrum with an ordinate axis of an RFU value (relative value) and the lower graphs each show the absorption spectrum. FIG. 6 shows a change with elapsed time of the peak RFU value (A), and shows a change with elapsed time at a wavelength of 346 nm (B).

As shown in the Figures, fluorescence is almost disappeared in all oligo-DNAs of (T20), T(6) and (T3) after 30 minutes. In particular, the fluorescence is quickly disappeared in the oligo-DNAs having short base lengths. After 35 minutes, the fluorescent spectra were measured. Immediately thereafter, 1.8 µl of 44 mM S.A. solution was again added to the sample for measurement. The fluorescence could be again detected. From this, the disappearance of the fluorescence could be considered due to oxidation of Cu(I) ions to Cu(II) ions. In each of the fluorescent spectra of the oligo-DNAs T(6) and T(3), as the peak intensity was decreased, a new peak was observed at a short wavelength side.

On the other hand, in each of the absorption spectra of the respective oligo-DNAs, a decrease in the peak intensity was observed with elapsed time. The absorption spectra were more gradually decreased as compared with the fluorescent spectra.

Figure 7:
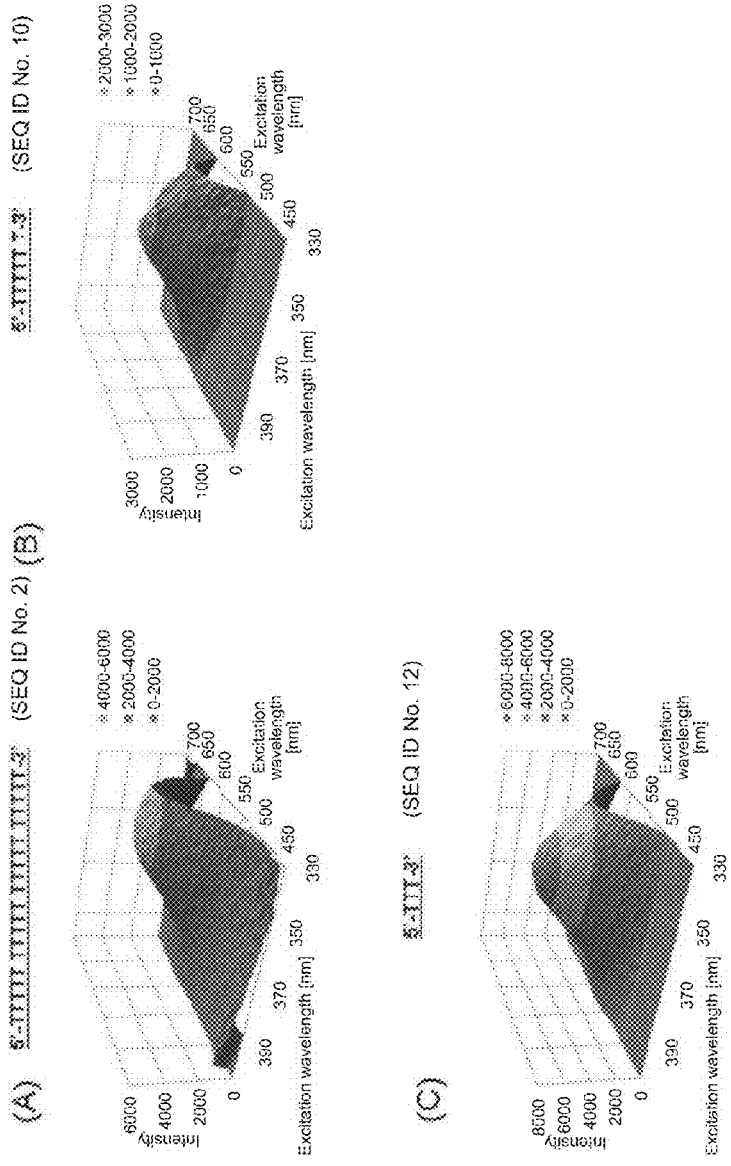
FIG. 7 Graphs each substituting a drawing and showing a two-dimensional fluorescent spectrum acquired in oligo-DNAs T(20), T(6) and T(3).
Figure 8:
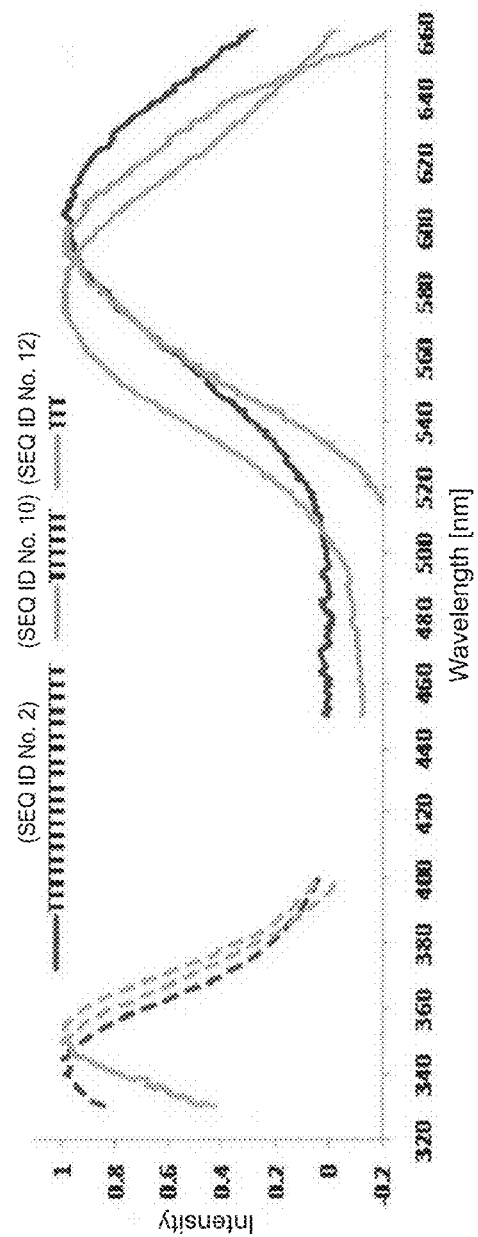
FIG. 8 A graph substituting a drawing and showing excitation spectra (broken lines) and fluorescent spectra (solid lines) obtained in oligo-DNAs T(20), T(6) and T(3) (Example 1).

FIG. 7 (A) to (C) show two-dimensional fluorescent spectra acquired in oligo-DNAs T(20), T(6) and T(3) by the type F-4500 spectrofluorophotometer. FIG. 8 shows excitation spectra (broken lines) and fluorescent spectra (solid lines) obtained in the respective oligo-DNAs. The spectrum was measured at a space of 1 nm for a fluorescent wavelength, and at a space of 2 nm for an excitation wavelength.

As shown in the Figures, it was confirmed that the patterns of the fluorescent spectra were changed depending on the base lengths of the oligo-DNAs. It was also confirmed that the patterns of the excitation spectra were changed depending on the base lengths.

Figure 9:
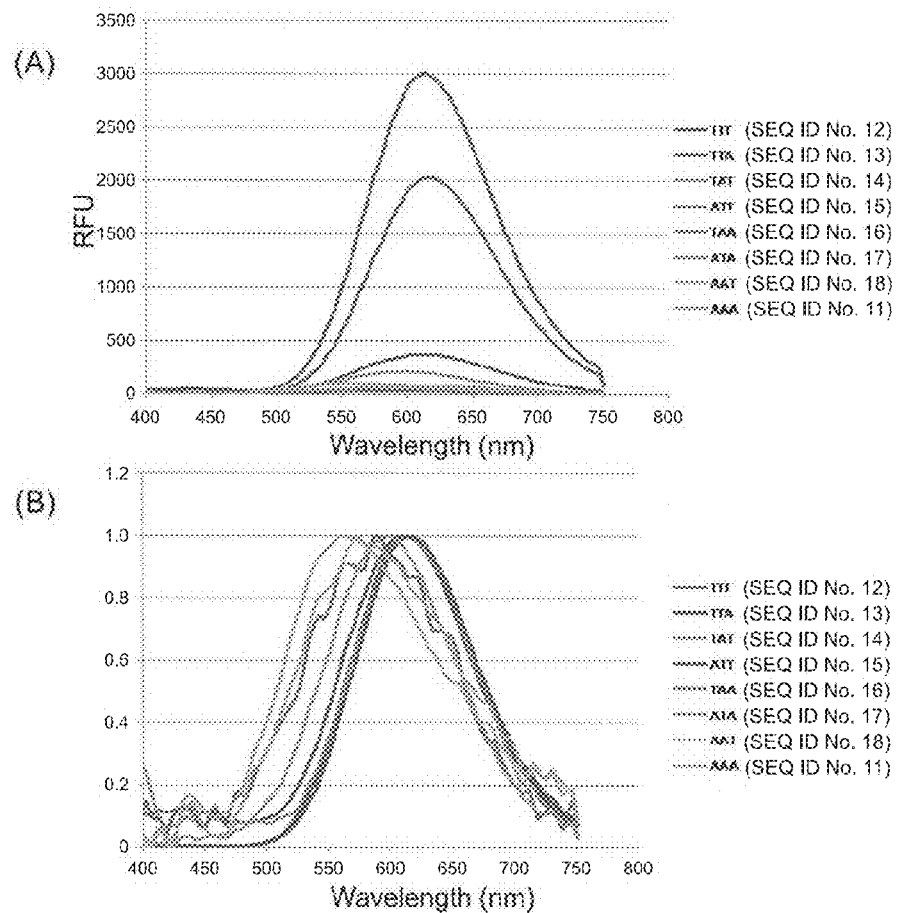
FIG. 9 Graphs each substituting a drawing and showing fluorescent spectra obtained in oligo-DNAs including a three base length sequence by combining adenine and thymine (Example 1).
Figure 10:
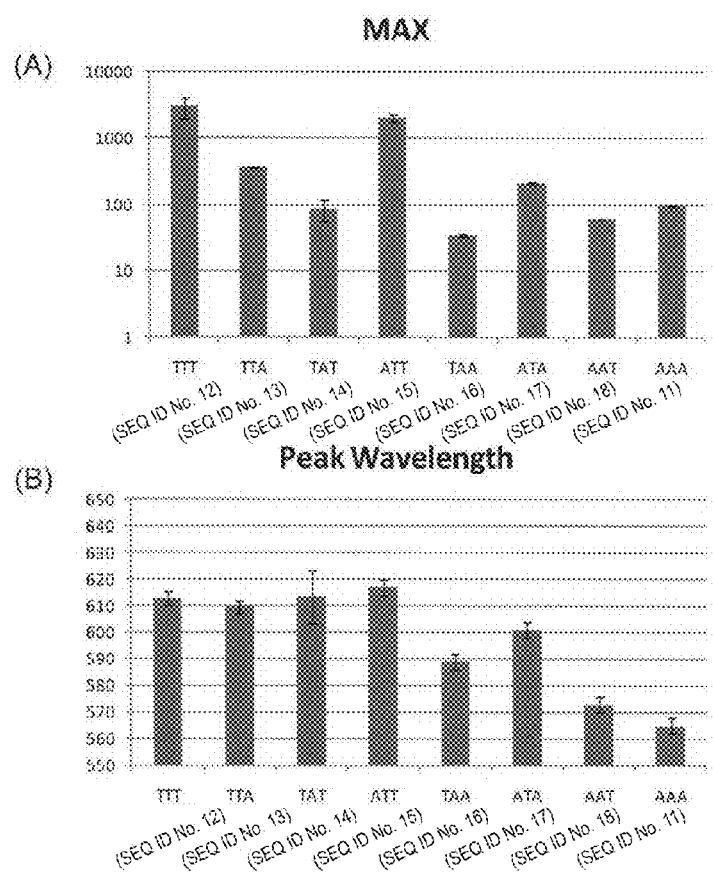
FIG. 10 Graphs each substituting a drawing and showing a maximum RFU value (A) and a peak FRU wavelength (B) of the fluorescent spectra obtained in oligo-DNAs including a three base length sequence by combining adenine and thymine (Example 1).

In order to further examine a relationship between the base sequences and the spectra, the oligo-DNAs each having a three base length sequence by a combination of adenine (A) and thymine (T) described in SEQ ID NOS: 11 and 18 were measured for the fluorescence. The results are shown in FIGS. 9 and 10. In FIG. 9, an ordinate axis (A) represents an RFU value in each wavelength measured by the Nanodrop and an ordinate axis (B) represents a value provided by dividing the RFU value in each wavelength by a maximum RFU value. FIG. 10 shows an average value and a standard error by measuring the maximum value of the RFU and the peak wavelength for three times.

As shown in the Figures, it was confirmed that the fluorescence intensity and the peak wavelength were changed depending on the base sequences of the oligo-DNAs.

Figure 11:
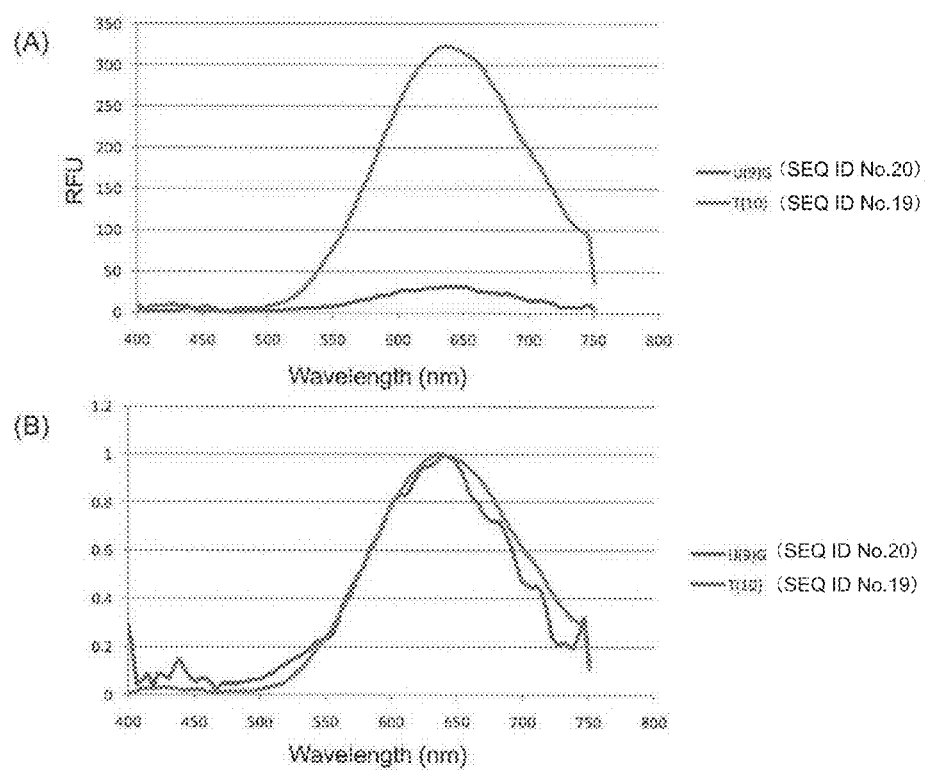
FIG. 11 Graphs each substituting a drawing and showing the fluorescent spectra obtained in oligo-DNAs including sequences of SEQ ID NOS: 19 and 20 (Example 1).

FIG. 11 shows the results of the measurement obtained in the oligo-DNAs including sequence of SEQ ID NOS: 19 and 20. It was confirmed that the oligo-DNAs having the sequence described in SEQ ID NO: 20 containing uracil (U) emitted the fluorescence having the spectrum shape and the peak position similar to that of the oligo-DNAs having the sequence described in SEQ ID NO: 19 containing thymine (T), although the fluorescence intensity in the oligo-DNAs having the sequence described in SEQ ID NO: 20 was faint.

<Discussion>

This Example showed that the orange-colored fluorescence having a wavelength of about 500 nm to 700 nm was observed by ultraviolet irradiation when DNAs were mixed with a HEPPSO buffered solution containing sodium chloride into which $CuSO_4$ and the S.A. were mixed. It was confirmed that the fluorescence intensity depended on the concentration of $CuSO_4$, and the fluorescence intensity and the spectrum were also influenced by the base sequences of the nucleic acids.

The fluorescence was observed in the oligo-DNAs containing at least thymine (T), adenine (A) or uracil (U). In the experiment where the oligo-DNAs each having a three base length containing thymine (T) and adenine (A) were used, the fluorescence was observed in any sequence. In addition, it is shown that the fluorescence intensity and the spectra were influenced not only by the amount of thymine (T) or adenine (A), but also by the position (sequence order) on the oligo-DNAs.

With time elapsed after the addition of the S.A., the fluorescence intensity was decreased with time, but was recovered by re-addition of the S.A. In the meantime, Cu(I) ions are very unstable in the presence of oxygen, and are changed into Cu(II) or solid copper as soon as the reduction effect of the S.A. is lost. From this, it is considered that the fluorescence is derived from the composite of Cu(I) ions and the nucleic acids. In order to detect the fluorescence by the interaction between copper and the nucleic acids, it may be desirable that a contact of the reaction solution with oxygen in the air be minimized.

Example 2

Example 2 illustrates that orange-colored fluorescence similar to that observed in Example 1 was emitted by ultraviolet irradiation under certain conditions when a solution containing nucleic acids was contacted with solid copper.

<Material and Method>

As the copper that was contacted with the nucleic acids, copper powder (Copper, Powder, −75 um, 99.9%/Cat. No. 030-18352/manufactured by Wako Pure Chemical Industries, Ltd., Osaka, Japan) was used.

As the RNAs, Rat Brain Total RNAs (Cat. No. 636622, Takara Bio Inc., Otsu, Japan) were used by dissolving it to DEPC treated water (Cat. No. 312-90201/Wako Pure Chemical Industries, Ltd., Japan.

PIPES, ACES, BES, TAPSO, HEPPSO, EPPS, TAPS, CAPS, TES, Tricine and OPSO were purchased from DOJINDO Laboratories (Kumamoto, Japan). Each of these was used by adjusting the pH pursuant to the protocols provided by the manufacturer. Other reagents were the same as in Example 1.

The nucleic acids were contacted with copper by mixing a variety of nucleic acids, salts and copper powder into a total amount of 40 microliters solution, and agitating it for 15 minutes. The amount of the copper powder added was 375 mg per milliliter of the solution, unless otherwise noted. The amount of the salt, or sodium chloride (NaCl), was 500 mM, unless otherwise noted.

After the sample was centrifuged to settle the copper powder, a supernatant was measured for the spectrum of the fluorescence and the intensity. The measurement of the spectra of the fluorescence and the intensity was performed in the similar steps as in Example 1.

<Results>

Figure 12:
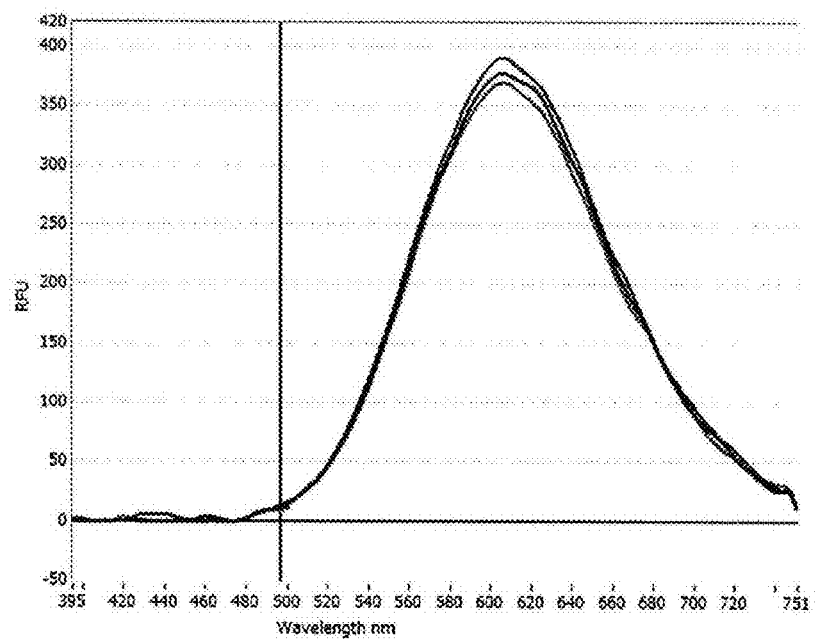
FIG. 12 A graph substituting a drawing and showing fluorescent spectra obtained by bringing a sample containing ssDNAs into contact with solid copper (Example 2).

The reaction solution to which 1.5 mg/ml of ssDNAs were added was measured for the fluorescence three times. The results are shown in FIG. 12 (abscissa axis: wavelength, ordinate axis: RFU). As shown in the Figure, when the sample containing the nucleic acids was contacted with solid copper and then UV-excited, the fluorescence having a peak around 600 nm could be detected.

Figure 13:
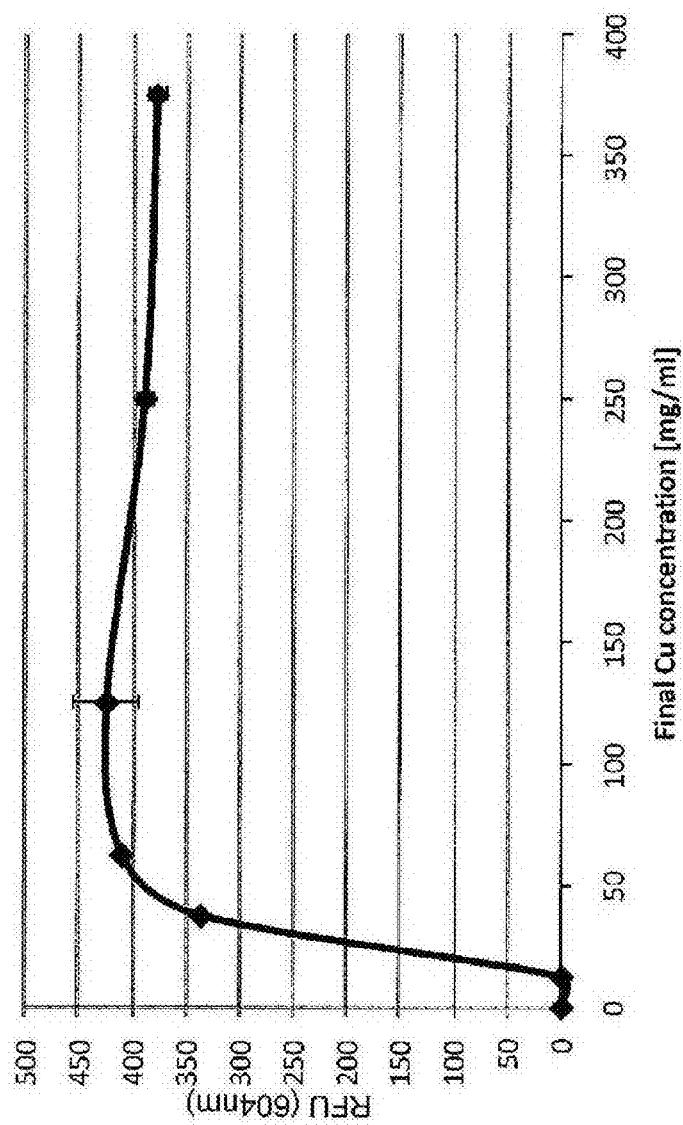
FIG. 13 A graph substituting a drawing and showing a fluorescent spectrum obtained by bringing a sample containing ssDNAs into contact with solid copper having different concentrations (Example 2).

Next, a reaction solution was prepared by adding the copper powder in the amount of 375 mg, 250 mg, 125 mg, 62.5 mg, 37.5 mg, 12.5 mg and 0 mg based on 1 mL of the reaction solution. To the reaction solution, 1.5 mg/ml of ssDNAs were added. The fluorescence was measured for three times. The result was shown in FIG. 13. As shown in the Figure, the fluorescence intensity depended on the amount of the copper powder. In the Cu powder used in this Example, apparent fluorescence was observed when the amount was 37.5 mg/ml or more. On the other hand, no apparent fluorescence was observed when the amount was 12.5 mg/ml or less.

Figure 14:
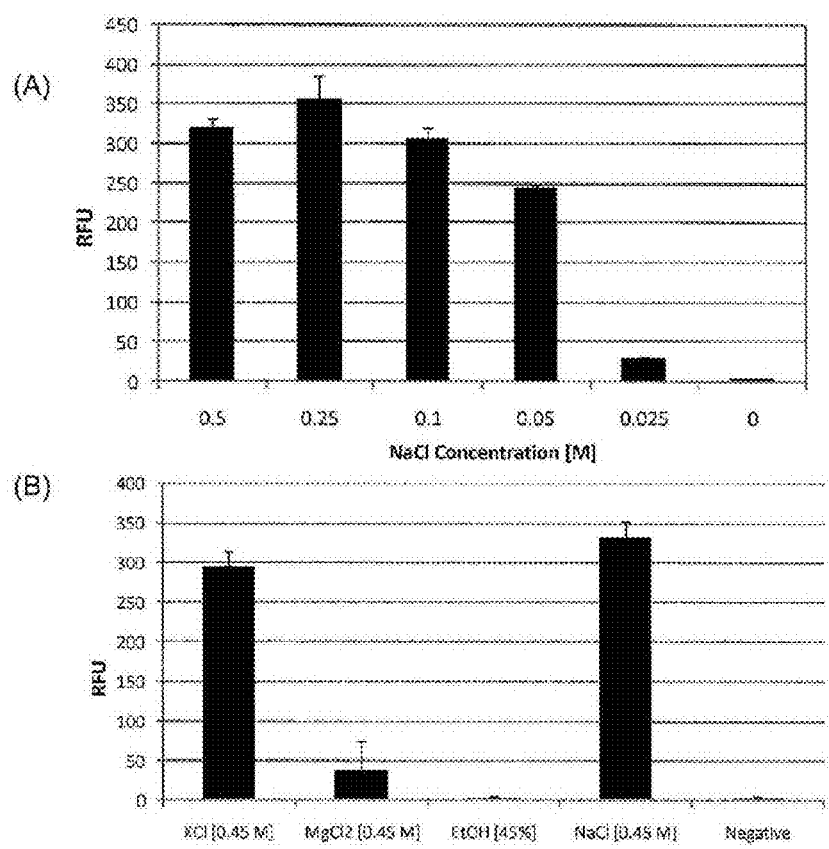
FIG. 14 Graphs each substituting a drawing and showing fluorescent spectra obtained by bringing a sample containing ssDNAs into contact with a reaction solution containing a salt having different types or concentrations (Example 2).

Then, the type and the concentration of the salt in the reaction solution were changed. To the reaction solution, 1.5 mg/ml of ssDNAs were added. The intensities of the fluorescence detected were compared. The results are shown in FIG. 14. (A) shows the fluorescence intensity detected in the reaction solution to which 0.5, 0.25, 0.1, 0.05, 0.025 and 0 M sodium chloride (NaCl) were added. (B) shows the fluorescence intensity detected in the reaction solution to which 0.45 M sodium chloride (NaCl), 0.45 M potassium chloride (KCl), 0.45 M magnesium chloride (MgCl2) and 45% ethanol (EtOH) were added. The fluorescence intensity was represented by the RFU at 604 nm, and measured for three times. The result was shown as the average and the standard error. As shown in the Figure, the fluorescence intensity depended on the amount of sodium chloride. Also, the fluorescence was detected under the coexistence of potassium chloride and magnesium chloride as well as sodium chloride.

Figure 15:
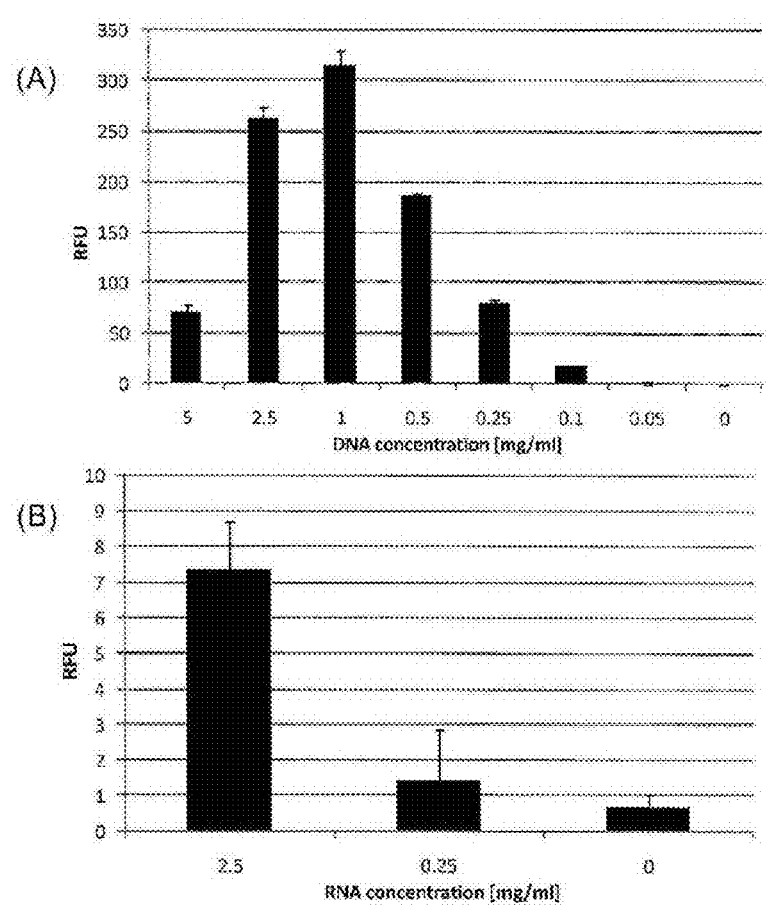
FIG. 15 Graphs each substituting a drawing and showing fluorescent spectra obtained by bringing a sample containing ssDNAs (A) or RNAs (B) having different concentrations with into contact solid copper (Example 2).

FIG. 15 shows comparison results of the fluorescence intensity detected when the concentration of the nucleic acids added to the reaction solution was changed. (A) shows the fluorescence intensity detected in the reaction solution to which 5, 2.5, 1, 0.5, 0.25, 0.1, 0.05, and 0 mg/ml of ssDNAs were added. (B) shows the fluorescence intensity detected in the reaction solution to which 2.5, 0.25, and 0 mg/ml of RNAs were added. The abscissa axis represents the concentration of the nucleic acids, and the ordinate axis represents the RFU at a fluorescent wavelength of 604 nm. The measurement was performed for three times. The concentration of sodium chloride (NaCl) was 0.25M, and the amount of the copper power was 200 mg per 1 ml. The condition was used in the following experiments, unless otherwise noted. As shown in the Figure, the fluorescence intensity depended on the concentration of DNAs and the concentration of RNAs.

Figure 16:
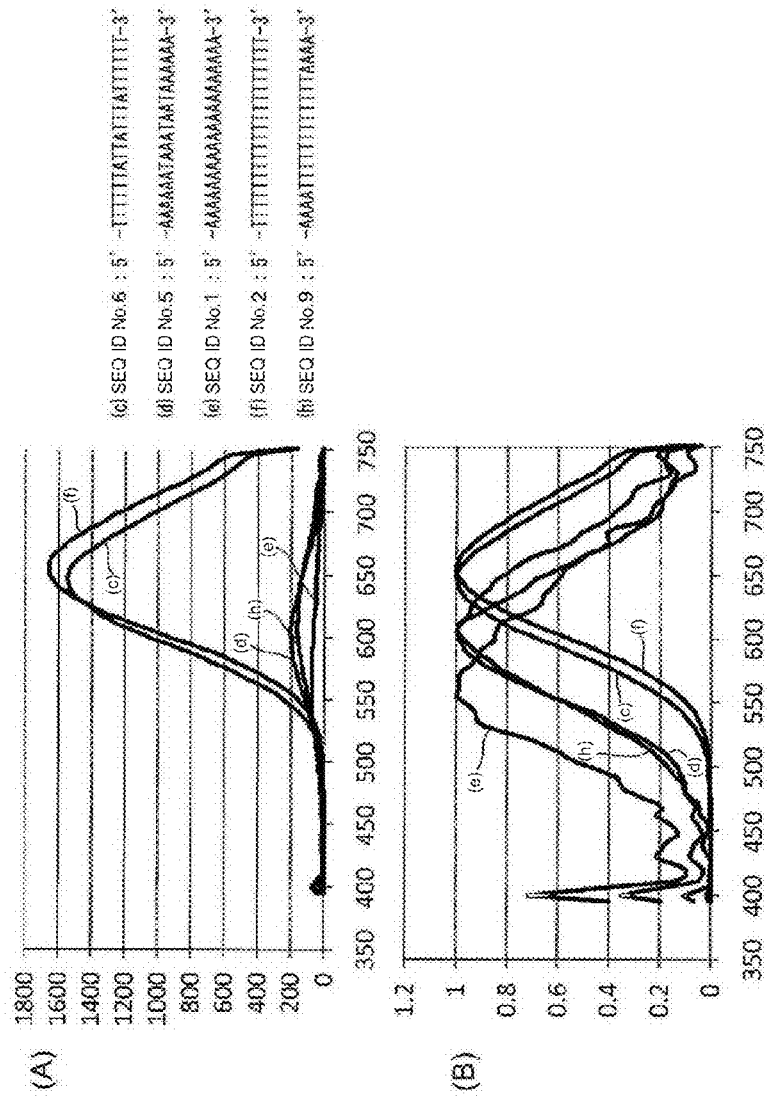
FIG. 16 Graphs each substituting a drawing and showing fluorescent spectra obtained by bringing a sample containing oligo-DNAs having different sequences into contact with solid copper (Example 2).

Next, the reaction solution to which 0.1 mM oligo-DNAs having different sequences described in SEQ ID NOS: 1, 2, 5, 6 and 9 was measured for the fluorescence. The results are shown in FIG. 16. An ordinate axis (A) represents an RFU value measured by the Nanodrop, and an ordinate axis (B) represents a relative RFU value when the peak height was set to 1. As shown in the Figure, the fluorescence intensity and the peak wavelength were influenced by the base sequences. In particular, it could be confirmed that when the percentage of thymine (T) was high, the fluorescence intensity was high and the peak wavelength became longer.

Figure 17:
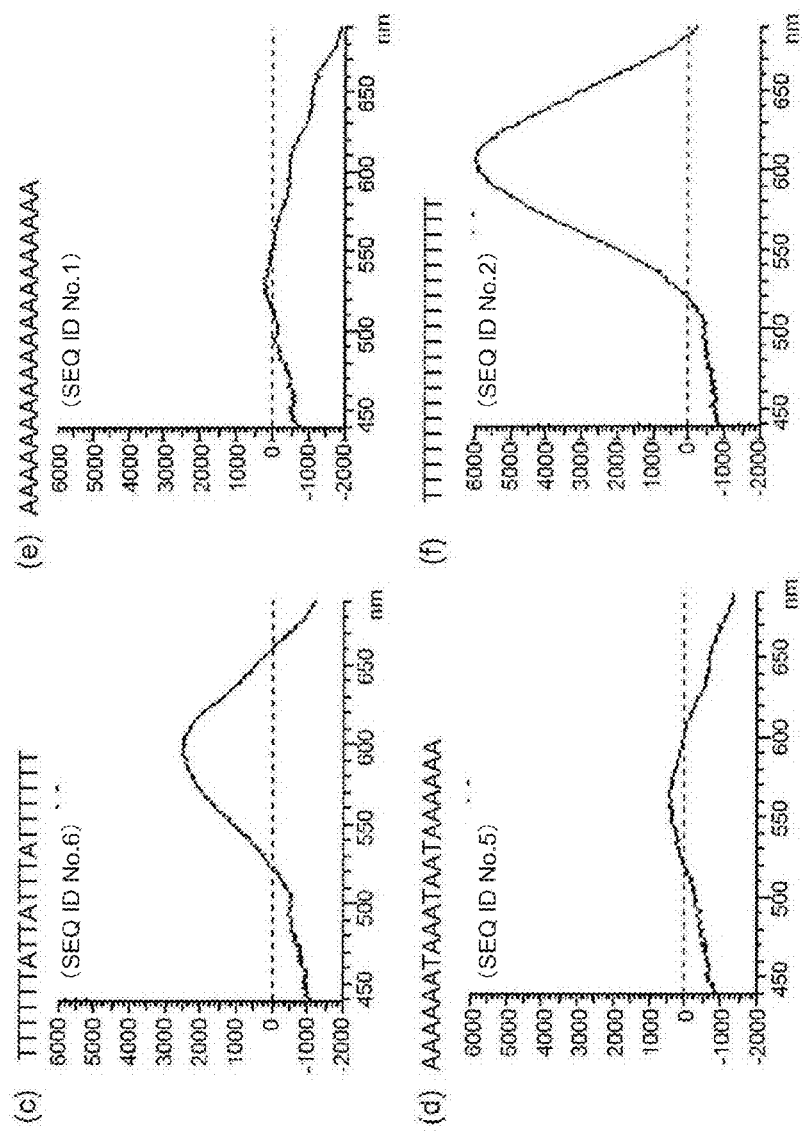
FIG. 17 Graphs each substituting a drawing and showing a fluorescent spectrum obtained by bringing a sample containing oligo-DNAs having different sequences into contact with solid copper (Example 2).
Figure 18:
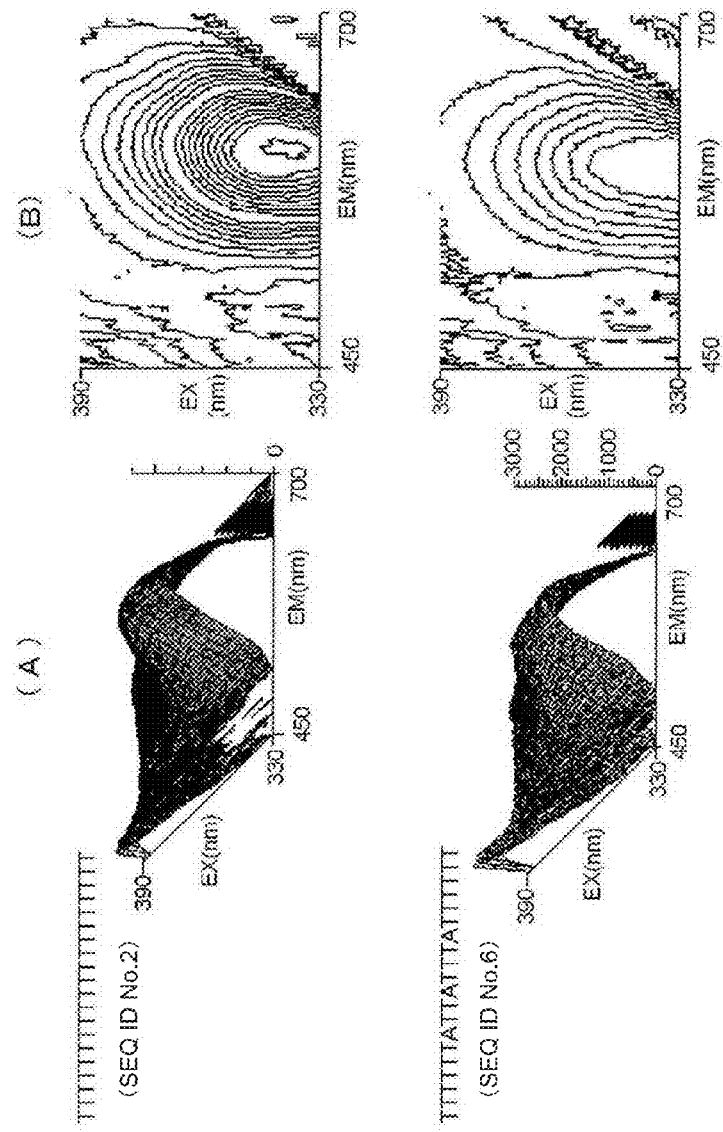
FIG. 18 Graphs each substituting a drawing and showing excitation-fluorescent spectra obtained by bringing a sample containing oligo-DNAs having different sequences into contact with solid copper (Example 2).

The reaction solution to which oligo-DNAs having sequences described in SEQ ID NOS: 1, 2, 5 and 6 was also measured using the type F-4500 spectrofluorophotometer. FIG. 17 shows the results of the fluorescent spectra (slit width of 2.5 nm) within 400 nm to 700 nm when the excitation light of 360 nm (slit width of 10 nm) was irradiated. Again, it could be confirmed that when the percentage of thymine (T) was high, the fluorescence intensity was high and the peak wavelength became longer in the sequence containing thymine (T) and adenine (A). FIG. 18 shows the results by scanning the excitation light at 330 nm to 390 nm (slit width of 3 nm) and 400 nm to 700 nm (slit width of 2.5 nm) to measure excitation-fluorescent spectra. (A) represents three dimensionally, and (B) represents a contour. An axis EX represents an excitation wavelength (nm), an axis EM represents a fluorescence wavelength (nm) and a height direction represents the fluorescence intensity. Based on the results, it could be read that the excitation and the fluorescent spectra and the intensity were changed by the different base sequences of the DNAs.

Figure 19:
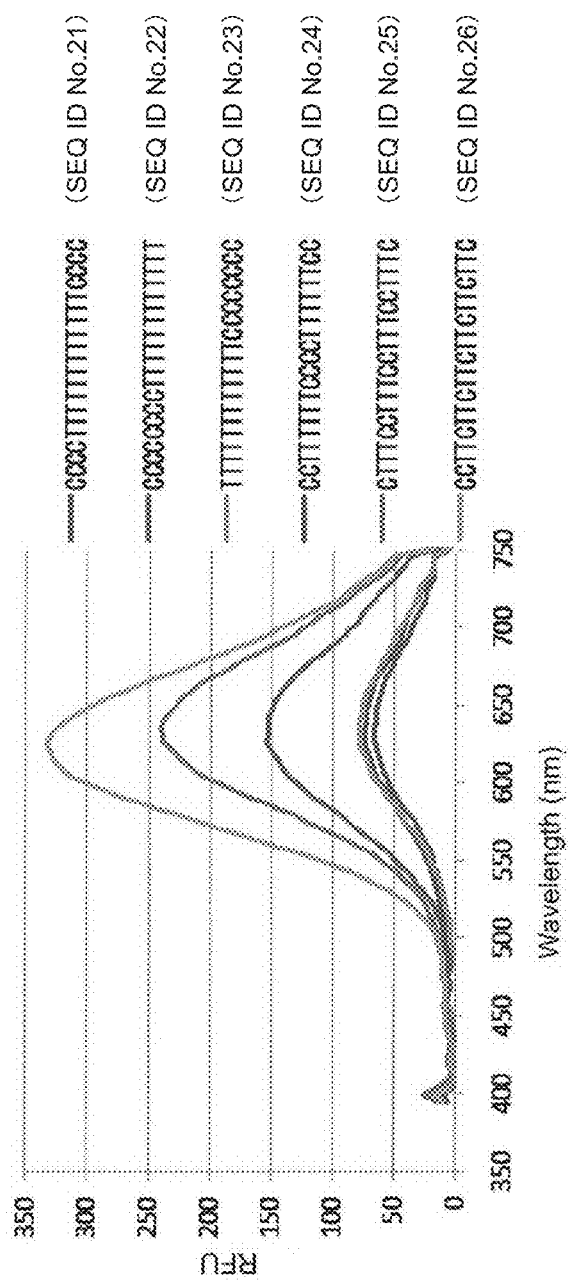
FIG. 19 A graph substituting a drawing and showing fluorescent spectra obtained in oligo-DNAs having combination sequences of eight-base cytosine and 12-base thymine (Example 2).

In order to further examine a relationship between the base sequences and the spectrum, the oligo-DNAs each having a combination sequence of cytosine (C) having eight bases and thymine (T) having 12 bases described in SEQ ID NOS: 21 and 26 were measured for the fluorescence. The results are shown in FIG. 19. As shown in the Figure, the fluorescence intensity differed when the sequence was different even if the base composition of the DNAs was the same.

Figure 20:
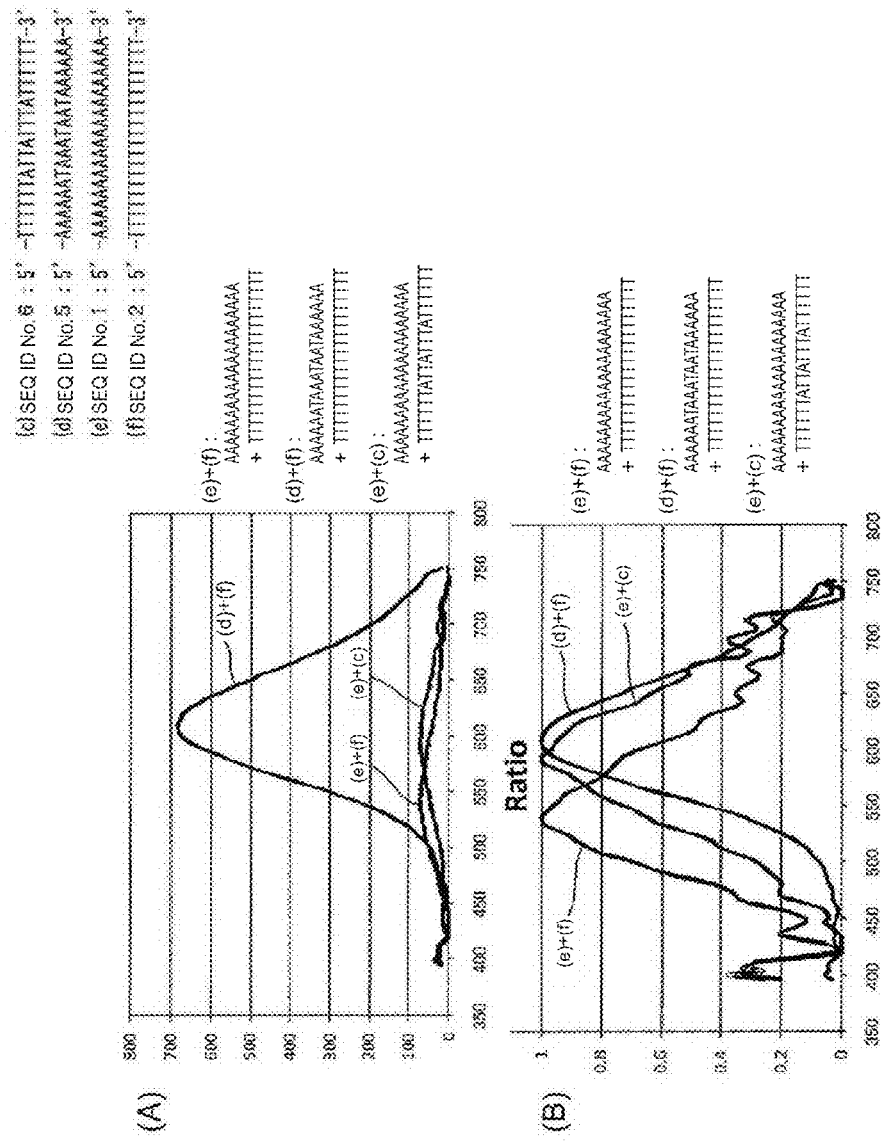
FIG. 20 Graphs each substituting a drawing and showing fluorescent spectra obtained in double-stranded DNAs including a mismatch (Example 2).

Next, the double-stranded DNAs including a mismatch were measured for the pattern of the fluorescent spectrum. As the double-stranded DNAs, three types: a mixture ((e)+(f)) of oligo-DNAs each having a sequence shown in SEQ ID NO: 1 and oligo-DNAs each having a sequence shown in SEQ ID NO: 2, a mixture ((d)+(f)) of oligo-DNAs each having a sequence shown in SEQ ID NO: 5 and oligo-DNAs each having a sequence shown in SEQ ID NO: 2, and a mixture ((e)+(c)) of oligo-DNAs each having a sequence shown in SEQ ID NO: 1 and oligo-DNAs each having a sequence shown in SEQ ID NO: 6 were used. Any of the oligo DNAs were mixed at a final concentration of 0.5 mg/ml. The results are shown in FIG. 20. An ordinate axis (A) represents an RFU value measured by the Nanodrop, and an ordinate axis (B) represents a relative RFU value when the peak height was set to 1. An abscissa axis represents a wavelength (nm). As shown in the Figure, the fluorescence intensity in the double-stranded DNAs was lower than that in the single-stranded DNAs. However, in the double-stranded DNAs having a mismatch of thymine (T), the strong fluorescence was confirmed.

Figure 21:
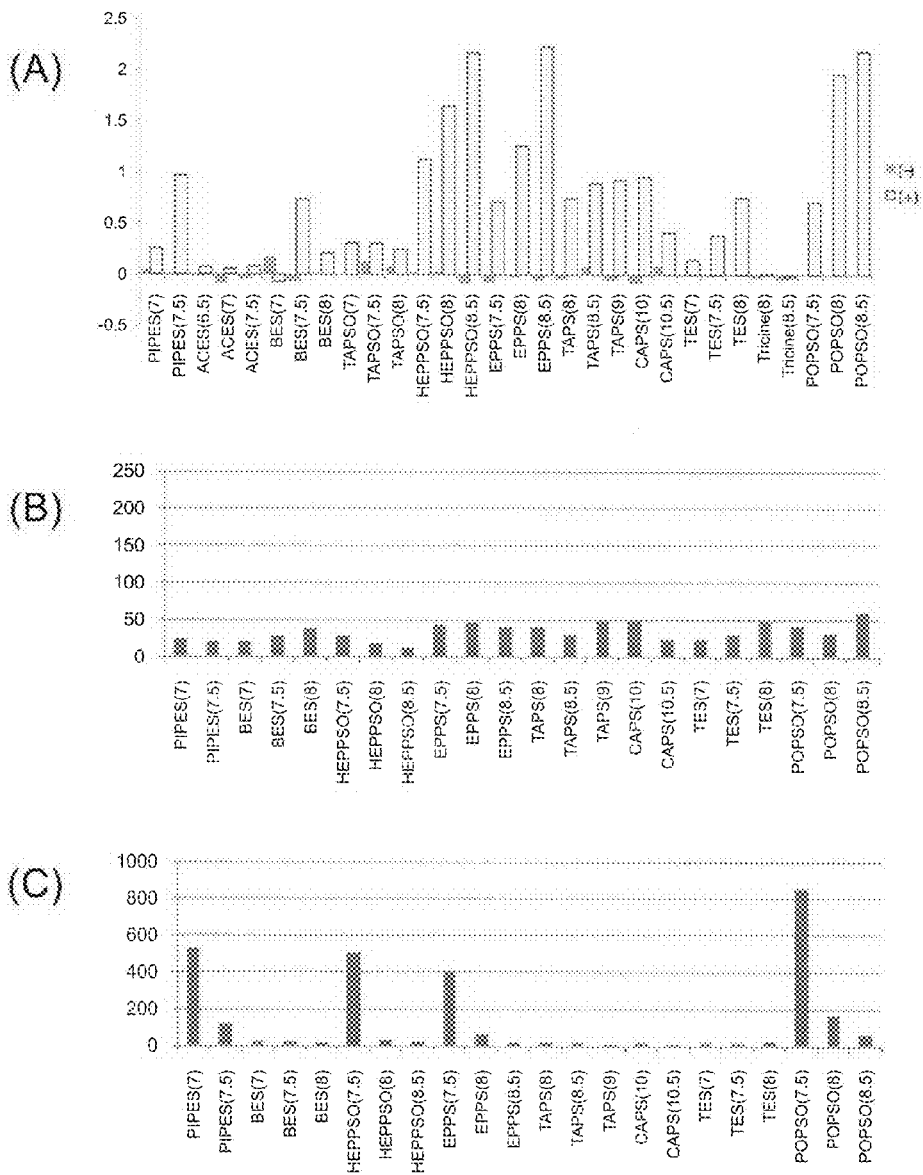
FIG. 21 Graphs each substituting a drawing and showing RFU values obtained by changing a type and a pH of a buffer of a reaction solution (Example 2).

The intensities of the fluorescence detected were compared, when the types of the buffer and the pH in the reaction solution were changed. The results are shown in FIG. 21. (A) shows relative values of peak RFU values of a sample (+) containing ssDNAs and a sample (−) containing no nucleic acids under each buffered condition. (B) shows a relative value of a peak RFU value of a sample containing oligo-DNAs having the sequence shown in SEQ ID NO: 1 under the same condition. (C) shows a relative value of a peak RFU value of a sample containing oligo-DNAs having the sequence shown in SEQ ID NO: 2 under the same condition. The concentration of each buffer was 50 mM, the final concentration of the ssDNAs was 0.5 mg/ml, and the final concentration of the oligo-DNAs was 25 mM. The relative value of the peak RFU value means that the peak RFU value measured under no buffered condition is set to 1. The fluorescence intensity depended on the types of the buffer. The fluorescence was almost not detected when no nucleic acids exist in the buffer.

<Discussion>

Based on the results in this Example, it revealed that the fluorescence could be detected under adequate conditions including the salt concentration, when the nucleic acids were contacted with solid copper powder, as is the case that the nucleic acids were contacted with Cu(I) ions. It seemed that the fluorescence observed in each case of copper ions and solid copper was provided by the same mechanism, because their properties such as wavelength properties and sequence dependency are almost the same. Also, the fluorescence was observed when the RNAs were used as the nucleic acids. In addition, in the double-stranded DNAs, strong fluorescence was observed when the mismatch exists especially in thymine (T). This suggested that binding with the complementary sequence might inhibit the formation of the fluorescent substance by binding the nucleic acids with copper. Also, it is considered that the increase in the fluorescence intensity at the mismatch site could be applied to a method of detecting for mutation in the base sequences of the nucleic acids.

In the experiments for comparing the fluorescence under each buffered condition, the fluorescence was observed in the buffer of PIPES, BES, HEPPSO, EPPS, TAPS, CAPS, TES and POPSO. In particular, strong fluorescence was detected in the buffer of PIPES, HEPPSO, EPPS and POPSO. The fluorescence could be observed within a pH range of 7.0 to 10.5. It was found that a change in the fluorescence intensity depending on the type of the buffer and the pH showed a different pattern depending on the base sequences of the nucleic acids. On the other hand, the buffer having a property to chelate and stabilize Cu(II) ions has a tendency that the fluorescence is not observed. Although no data is provided in this Example, the fluorescence was almost not observed when the reaction solution containing, for example, a Tris buffer, EDTA or the like was used.

Example 3

In Example 3, it was confirmed that the fluorescence could be detected after the nucleic acids were brought into contact with copper sputtered on the surface of the glass, and the properties of the fluorescence were analyzed.

<Material and Method>

As the DNAs, the ssDNAs described in Example 1 were used. As the RNAs, the RNAs described in Example 2 were used.

Copper was sputtered on the surface of the glass using an apparatus, SH-350 manufactured by ULVAC, Inc. (Kanagawa, Tokyo) on which a Cu target, 99.99% (Kojundo Chemical Laboratory Co., Ltd, Saitama, Japan) was mounted. In the sputtering, a thickness was set to 40 nm, and an adequate sputtering time was set based on a deposition speed measured in advance. The glass for sputtering silver was manufactured by Kyodo International, Inc., Kanagawa, Japan.

On a slide glass on which copper or silver was sputtered or an untreated slide glass, a sample solution was placed, and a gap cover glass, 24×25 No. 4/#CG00024/Matsunami Glass Ind., Ltd., Osaka, Japan was covered thereon. After it was allowed to be stood for about 5 minutes, the fluorescence was observed. For the observation, an inverted microscope Ti-U (Nikon Co., Tokyo, Japan) was used. For capturing the fluorescence, a filter set UV-1A (Ex: 365/10, DM: 400, BA: 400/Nikon) was used. For capturing and recording an image, a digital CCD camera Retiga 2000R (QImaging, BC, Canada) and a 20× objective lens was used.

<Results>

Figure 22:
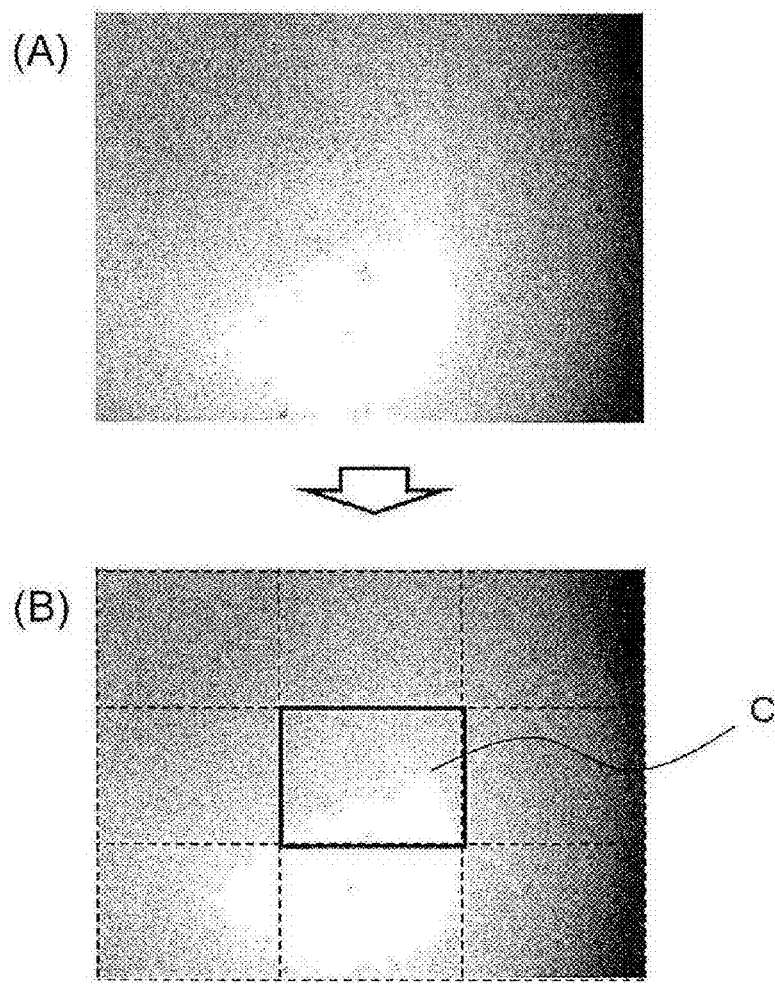
FIG. 22 Photographs each substituting a drawing and showing a fluorescent image obtained by bringing copper sputtered on a glass surface into contact with ssDNAs (Example 3).
Figure 23:
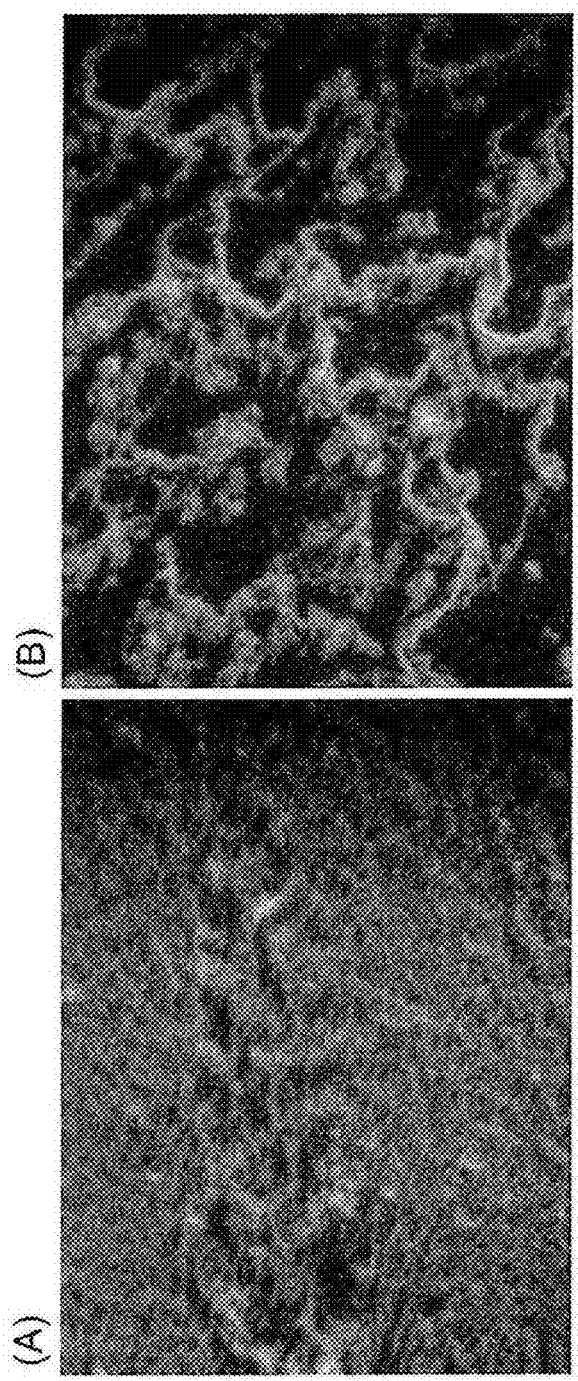
FIG. 23 Photographs each substituting a drawing and showing a fluorescent image obtained by bringing copper sputtered on a glass surface into contact with RNAs (Example 3).

FIG. 22 shows images captured after the sample containing 5 mg/ml of DNAs and 0.5 M of NaCl was allowed to stand for 5 minutes on the copper sputtered glass. FIG. 23 shows images captured after the sample containing 5 mg/ml of RNAs and 0.5 M of NaCl was allowed to stand for 5 minutes on the copper sputtered glass.

As shown in FIG. 22(A), when the sample containing DNAs was used, smooth fluorescence was observed on the entire captured image. On the other hand, as shown in FIGS. 23 (A) and (B), when the sample containing RNAs was used, the fluorescence having a specific wave-like pattern within the captured image was observed. A prospective cause of the pattern specific to the RNAs was that the single-stranded RNAs were hybridized each other to form the higher order structure.

Next, the fluorescence intensity within the captured image was converted into numerals. Each captured image was divided into nine sections as shown in FIG. 22 (B). One of the nine sections (C in the Figure) was set to be a measuring range. An average value of the fluorescence intensity within the measuring range was calculated. For each sample, five parts on the slide were captured to calculate the average value from each image. The resultant five average values were further averaged and calculated for standard deviation.

Figure 24:
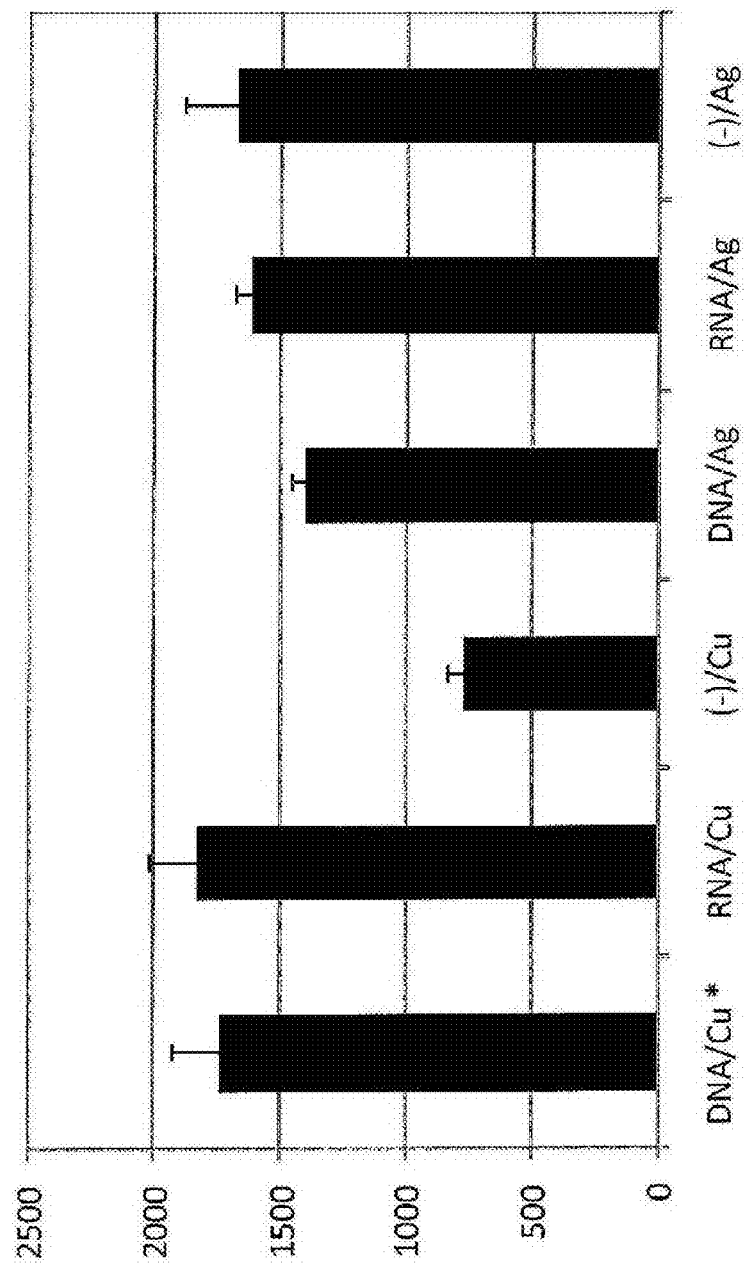
FIG. 24 A graph substituting a drawing and showing a fluorescence intensity obtained by bringing copper or silver sputtered on a glass surface into contact with a sample including DNAs or RNAs (Example 3).

FIG. 24 shows the fluorescence intensity acquired when the sample containing the DNAs or the RNAs was contacted with copper or silver sputtered on the glass. In FIG. 24, "DNA/Cu", "RNA/Cu", and "(−)/Cu" denote the sample containing 5 mg/ml DNAs, the sample containing 5 mg/ml of RNAs, and the sample containing no nucleic acids; the fluorescence intensity being measured on the Cu sputtered glass. In addition, "DNA/Ag", "RNA/Ag", and "(−)/Ag" denote the sample containing 5 mg/ml of DNAs, the sample containing 5 mg/ml of RNAs, and the sample containing no nucleic acids; the fluorescence intensity being measured on the Ag sputtered glass. Each sample contained 0.5 M NaCl. Since the fluorescence intensity in the "DNA/Cu" was significantly greater than those of the other samples, its exposure time was 1 minute. In all samples excluding the "DNA/Cu", the exposure time was 5 seconds.

As shown in the Figure, in the Cu sputtered glass, the "DNA/Cu" and the "RNA/Cu" had the fluorescence intensity higher than the "(−)/Cu". Especially in the DNA sample, the strong fluorescence was detected. On the other hand, in the Ag sputtered glass, the "DNA/Ag" and the "RNA/Ag" showed no increase in the fluorescence intensity as compared with the "(−)/Ag". As compared with the "(−)/Cu", the "(−)/Ag" showed the higher measured value. This may be caused by a background derived from a reflected light, a scattered light or autofluorescence on the Ag sputtered surface.

Figure 25:
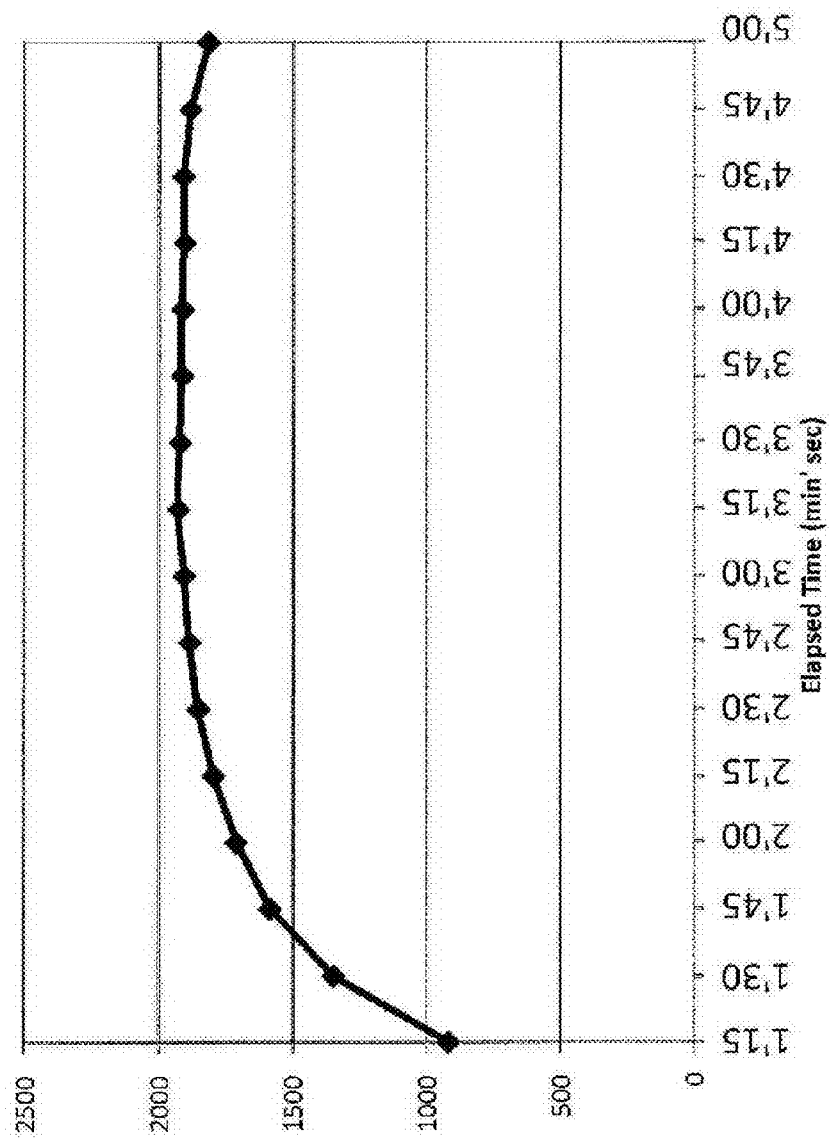
FIG. 25 A graph substituting a drawing and showing a change with elapsed time in a fluorescence intensity obtained by bringing copper sputtered on a glass surface into contact with ssDNAs (Example 3).

Next, a change in the fluorescence intensity with elapsed contact time of the nucleic acids with copper was examined. A point of time when the sample containing 5 mg/ml of ssDNAs and 0.5 M of NaCl was placed between the Cu sputtered glass and the gap cover glass was designated as a starting point to measure the fluorescence intensity per predetermined time. The image was captured every 15 seconds, and a shutter for excitation light was opened and closed per capturing session. The ×10 objective lens was used, and the exposure time was 1 second. In every time, one image captured was used to measure the fluorescence intensity. The results are shown in FIG. 25.

As shown in the Figure, the fluorescence intensity was gradually increased for several minutes after the sample was introduced, and reached the maximum value within about three minutes.

Figure 26:
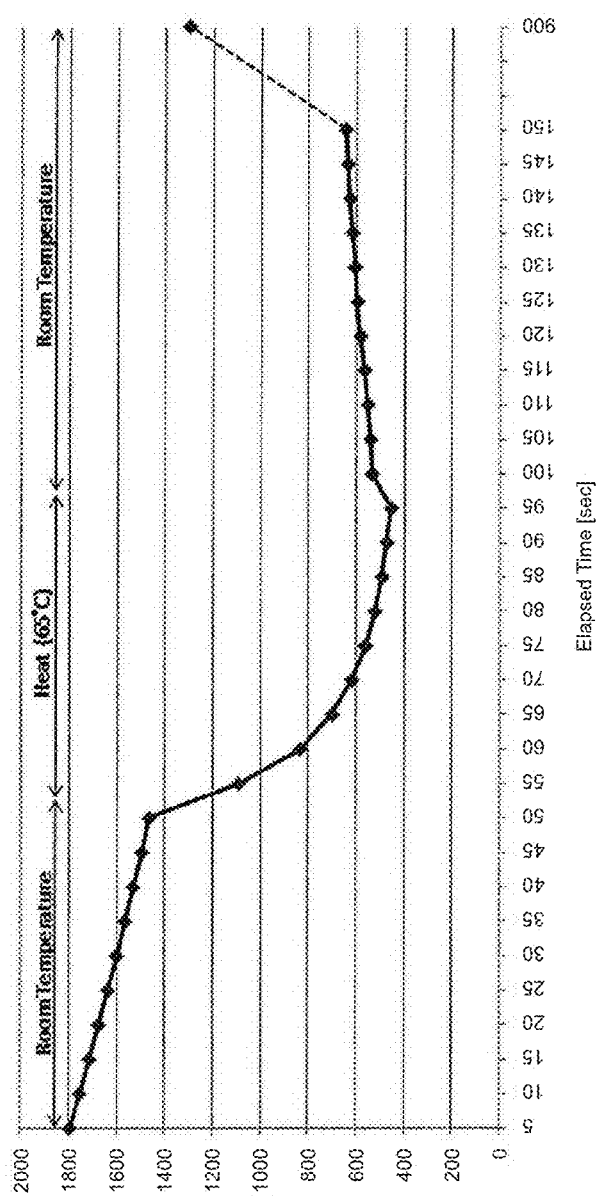
FIG. 26 A graph substituting a drawing and showing a change in a fluorescence intensity when a temperature is changed after copper sputtered on a glass surface is contacted with ssDNAs (Example 3).

After a predetermined time was elapsed from the contact of the nucleic acids with copper, a change in the fluorescence intensity by temperature change was examined. Immediately after the image has been captured, it held at room temperature. After 50 seconds, a heat block heated to 65° C. was gently placed over the Cu sputtered glass. After 100 seconds, the heat block was removed. The image was captured every 5 seconds. After 150 seconds, the measurement was stopped for now and the shutter for excitation light was closed. After 900 seconds, the measurement was again made. The results are shown in FIG. 26.

As shown in the Figure, the fluorescence intensity was gradually decreased for the first 50 seconds. This might be caused by fluorescence photobleaching. During the next 50 seconds, the fluorescence was disappeared at a speed apparently different from the fluorescence photobleaching. After the heat block was removed and it returned to room temperature, the fluorescence was gradually recovered. After 900 seconds, the fluorescence intensity was returned to a level that color degraded fluorescence intensity was subtracted from initial fluorescence intensity. These results show that the fluorescence emitted from the nucleic acids contacted with copper was heat sensitive, and was reversibly disappeared as the temperature increased.

Example 4

Example 4 illustrates that the cell nuclei could be fluorescently observed by introducing the sample containing cells onto the copper-sputtered glass.

<Material and Method>

As PBS, Dulbecco's Phosphate Buffered Saline, Ca/Mg free (Invitrogen Corporation, CA, USA) was used.

In an onion thin skin experiment, a commercially available onion thin skin was carefully peeled by a pair of tweezers, soaked into distilled water and rinsed for using it. The onion thin skin was placed on the Cu sputtered glass, was soaked into the PBS, was covered by a cover glass, and was then observed.

In an experiment of a human leukocyte sample, IMMUNO-TROL Cells (Cat. No. 6607077, Beckman Coulter, Inc., Fullerton, Calif., USA) were treated as follows: Firstly, 500 microliters of the IMMUNO-TROL Cells were separated, cleaned with PBS, and settled using a centrifugal machine (1200 rpm, 5 min). Thereafter, a supernatant was discarded to flake pellets, water hemolysis treatments are repeated two times to provide a sample. The sample was diluted with PBS, thereby preparing a leukocyte sample. The water hemolysis treatment was performed as follows: After the pellets obtained as the result of the centrifugation were sufficiently flaked, 9 ml of deionized water was added, was mixed upside down for 30 seconds, 1 mL of 10×PBS Buffer (Nippon Gene Co., Ltd., Tokyo, Japan) was added and fully agitated. The cells were centrifuged (1200 rpm, 5 min) and were settled to remove a supernatant. The leukocyte sample was placed on the Cu sputtered glass, was covered by a cover glass, and was then observed.

The copper sputtered glass, the cover glass, the microscope etc. were the same as in Example 3. In the sputtering, a thickness was set to 20, 40, or 100 nm. The thickness was set to 40 nm in the following experiments, unless otherwise noted. When Cu was sputtered only on a part of a slide glass surface, a polyimide tape was adhered on the slide glass surface excluding a 5 mm square in a center part, thereby performing the sputtering. Then, the polyimide tape was removed. Thus, the Cu sputtered glass having a Cu layer only formed on the 5 mm square in the center part was produced.

The onion thin skin was fluorescently observed using an excitation filter: 365/10 nm, a dichroic mirror: 400 nm, and a fluorescent filter: 590LP. The leukocyte sample and Jurkat cells were fluorescently observed using a filter set UV-1A (Ex: 365/10, DM: 400, BA: 400/Nikon).

<Results>

Figure 27:
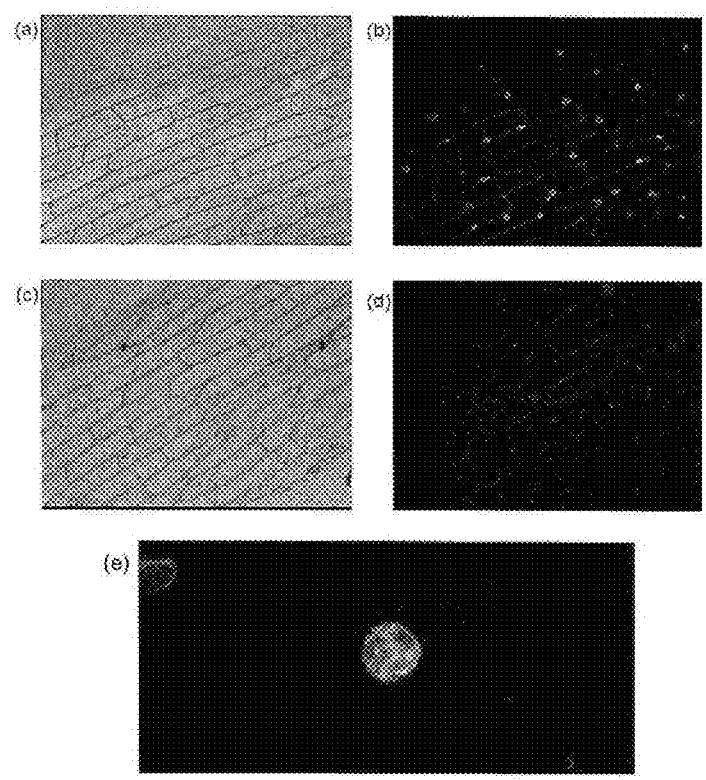
FIG. 27 Photographs each substituting a drawing and showing results of fluorescence observation of an onion thin skin on a copper sputtered glass (Example 4).

FIG. 27 shows images of the onion thin skin on the copper sputtered glass fluorescently observed and captured. (a) and (b) show observed images on the Cu sputtered glass. (c) and (d) show observed images on a slide glass without sputtering Cu thereon. (a) and (c) are bright field observed images. (b) and (d) are fluorescent images. (a) to (d) are images captured using a ×10 objective lens. (e) is an image captured using a ×40 objective lens.

As shown in the Figures, strong fluorescence specific to the cell nuclei was observed on the cells over the Cu sputtered glass. Although slight fluorescence was observed on a part of cell walls and the like, it is considered as autofluorescence of the cell walls and the like, because it was observed on the cells over the slide glass without sputtering Cu thereon.

Figure 28:
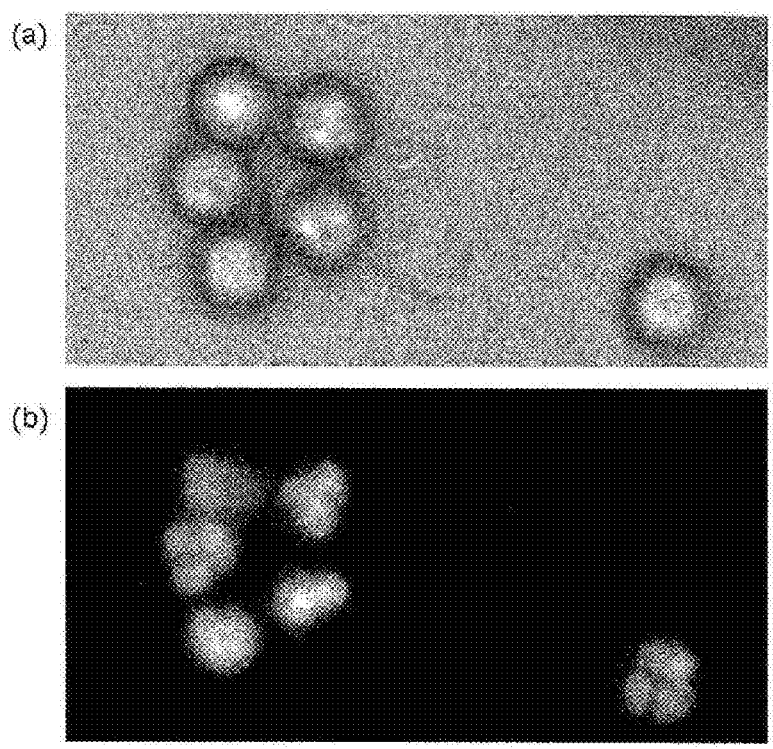
FIG. 28 Photographs each substituting a drawing and showing results of fluorescence observation of a human leukocyte sample on a copper sputtered glass (Example 4).

Next, animal cells were observed. FIG. 28 shows images acquired by fluorescently observing and capturing the human leukocyte sample on the copper sputtered glass. (a) is a bright field observed image. (b) is a fluorescent image. The ×40 objective lens was used.

In the fluorescent image, segmented neutrophils specific to the leukocyte were apparently observed.

Figure 29:
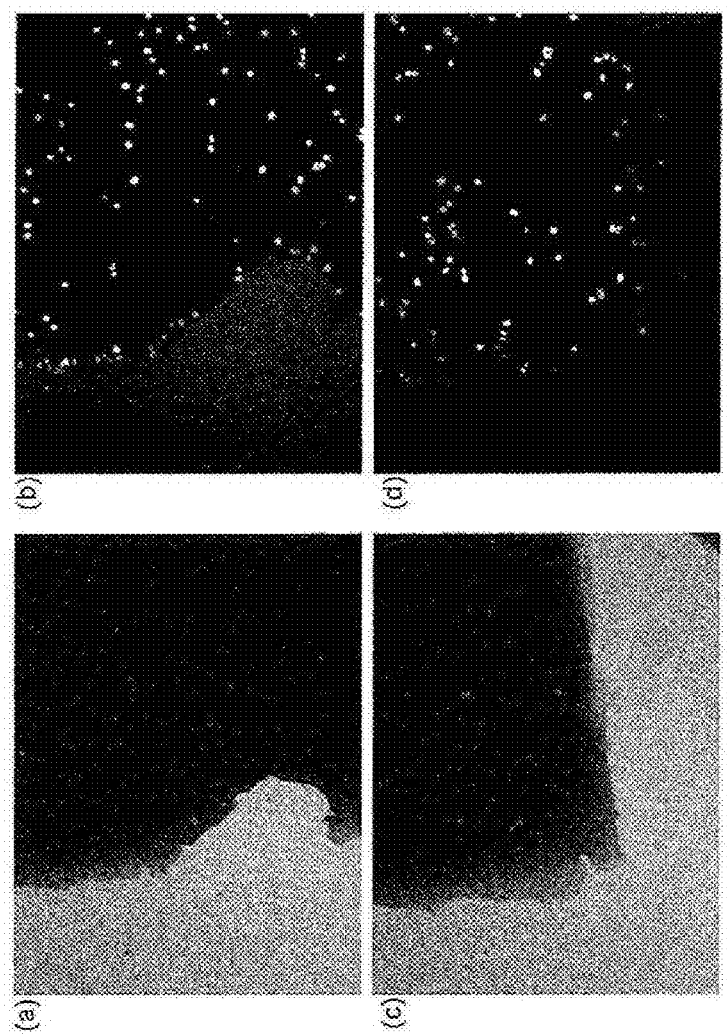
FIG. 29 Photographs each substituting a drawing and showing results of fluorescence observation of Jurkat cells on a copper sputtered glass (Example 4).

FIG. 29 shows images observed by using the Cu sputtered glass where Cu was sputtered only on a part of a slide glass surface. On the Cu sputtered glass, human leukocyte cell strains, i.e., Jurkat cells, were spread, were covered by the cover glass, and were then observed using the ×20 objective lens. The images were captured at a boundary between a Cu deposited area and a no Cu deposited area on the Cu sputtered glass. (a) and (c) are bright field observed images; black areas occupying more than half are areas where light is not transmit, because the Cu layers are formed. (b) and (d) are fluorescent images.

Figure 30:
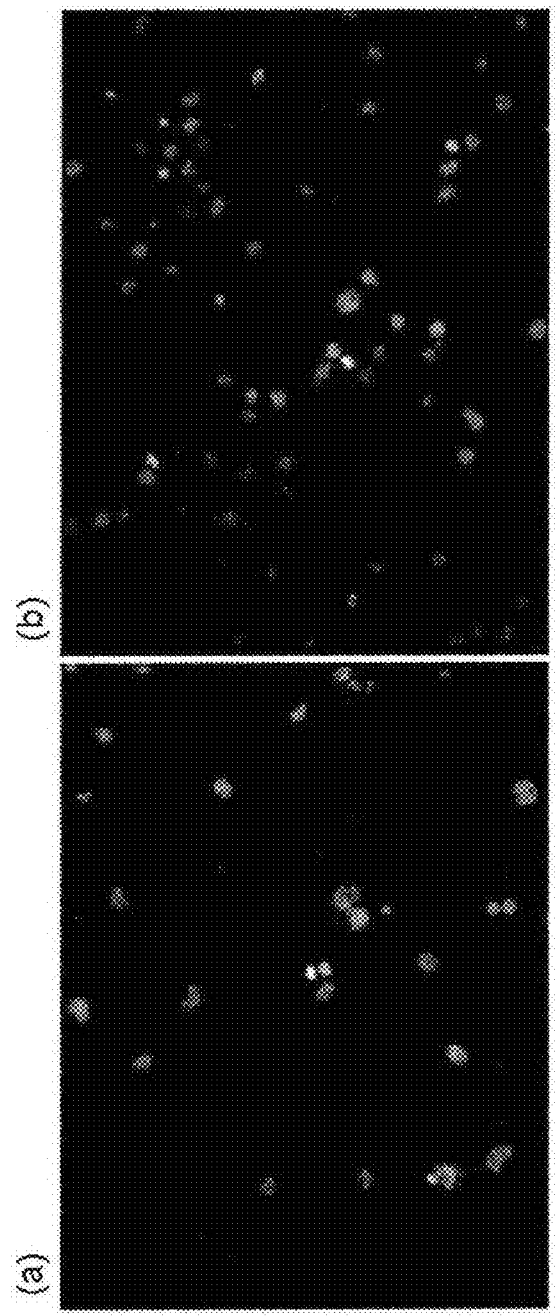
FIG. 30 Photographs each substituting a drawing and showing results of fluorescence observation of Jurkat cells on a copper sputtered glass (Example 4).

Strong fluorescence was observed only on the cell nuclei of the cells in the Cu deposited area. FIG. 30 shows observation results of the Jurkat cells using the Cu sputtered glass on which the Cu layer was formed in a thickness of 20 nm (a) or 100 nm (b). The fluorescence from the cell nuclei was observed at either thickness.

<Discussion>

The results in this Example show that the fluorescence can also be detected by bringing the cell nuclei into contact with copper. It is clear that the phenomenon occurs only on the glass substrate on which copper is sputtered, and is the result of the action between the cell nuclei and copper.

As a result of the fluorescence observation of the onion thin skin cells and the leukocyte cells, a difference between the shapes of cell nuclei in the cells was apparently shown. From this, according to the method of detecting nucleic acids of the present technology, different shapes of cell nuclei depending on the types of the cells can be identified.

Although not shown in this Example, in the experiment using the slide glass having copper sputtered on a part thereof, after the fluorescence was observed from only the cells on the Cu deposited area, the slide glass was inclined to move the cells from the Cu deposited area to the no Cu deposited area. After moving, the fluorescence was continuously observed. From this, even if the site where copper is contacted with the cells is spaced from the site where the cells are fluorescently observed, it is found that the fluorescence can be detected by disposing a means for moving the sample between the both sites.

After the fluorescence from the cell nuclei of the cells between the Cu sputtered glass and the cover glass was confirmed, the cover glass was removed and the solution containing the cells were exposed to air. Then, the fluorescence was quickly disappeared. Also in the experiment using Cu(II) ions and S.A. in Example 1, it was found that the fluorescence was disappeared after the reaction solution was exposed to air for a long time. The disappearance of the fluorescence could be considered due to oxidation of Cu(I) ions by the contact with air. Accordingly, the fluorescence generation may be inhibited by bringing the sample solution into contact with air (in particular, exposing to oxygen contained in the air). It is considered that the method of detecting nucleic acids according to the present technology is preferably performed by limiting the contact with air, e.g., in the microchip.

Example 5

In Example 5, it was confirmed that the fluorescence could be emitted from oligo-DNAs having a two base length under the similar experimental conditions as in Example 1.

<Material and Method>

Seven types of oligo-DNAs purchased from Invitrogen Corporation were measured for the fluorescence using the similar materials and method as in Example 1. The base sequences of the oligo-DNAs used are T(20) (SEQ ID NO: 1), T(10) (SEQ ID NO: 19), T(6) (SEQ ID NO: 10), T(5) (SEQ ID NO: 27), T(4) (SEQ ID NO: 28), T(3) (SEQ ID NO: 12), T(2) (SEQ ID NO: 29). Here, a $CuSO_4$ concentration was set to 0.4 mM, an S.A. concentration was set to 4 mM, and the NanoDrop 3300 was used for measurement.

<Results>

Figure 31:
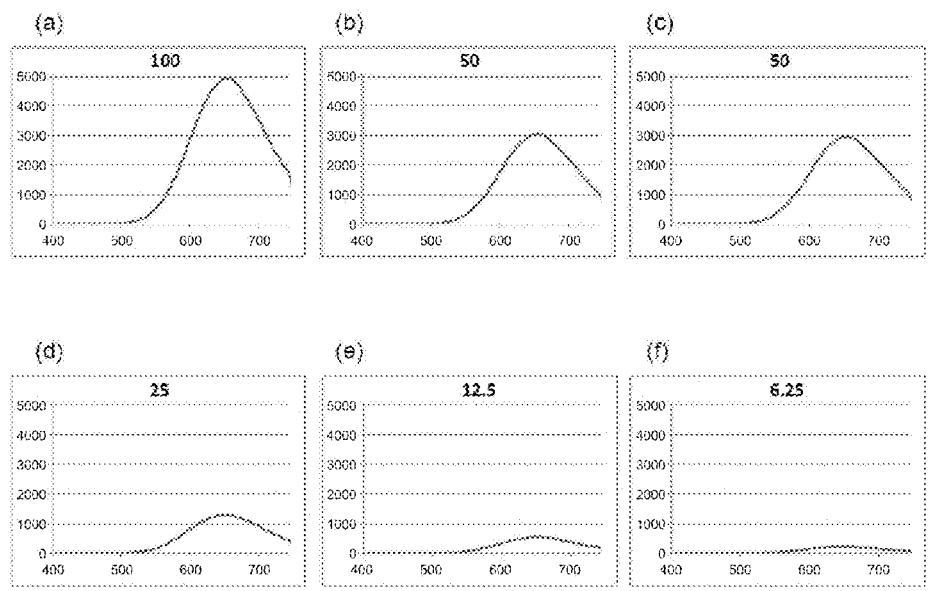
FIG. 31 Graphs each substituting a drawing and showing a fluorescent spectrum obtained in oligo-DNAs with T(20) at different concentrations (Example 5).
Figure 32:
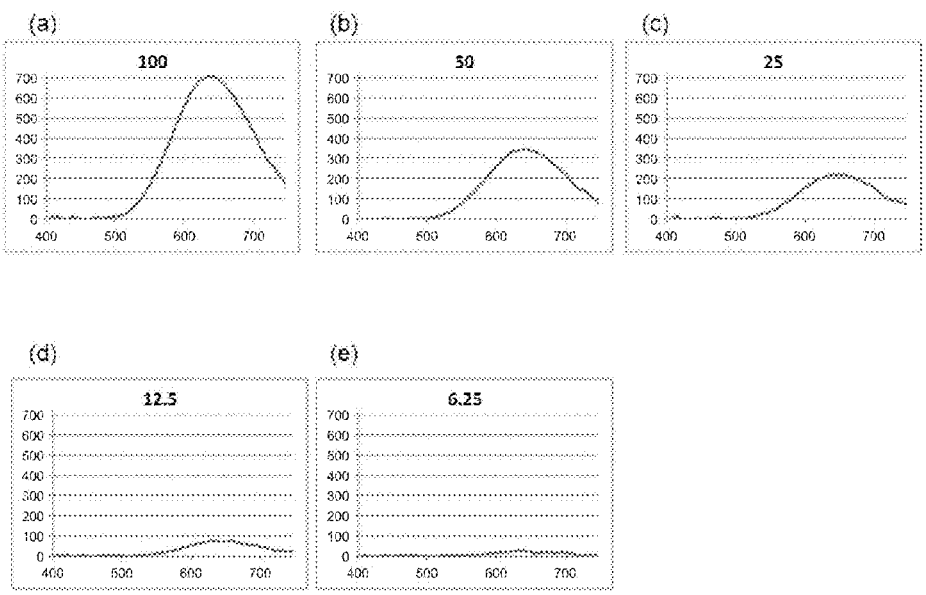
FIG. 32 Graphs each substituting a drawing and showing a fluorescent spectrum obtained in oligo-DNAs with T(10) at different concentrations (Example 5).
Figure 33:
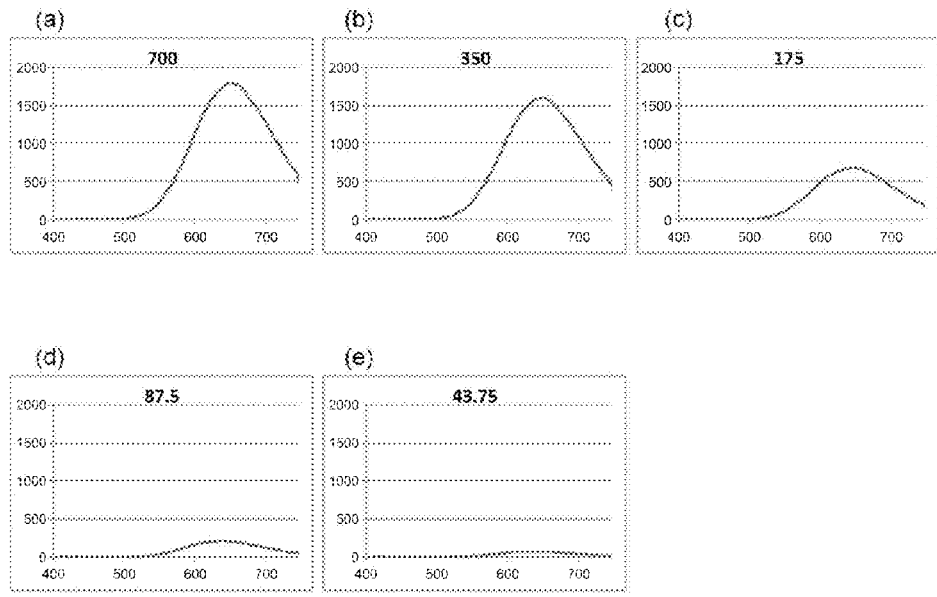
FIG. 33 Graphs each substituting a drawing and showing a fluorescent spectrum obtained in oligo-DNAs with T(6) at different concentrations (Example 5).
Figure 34:
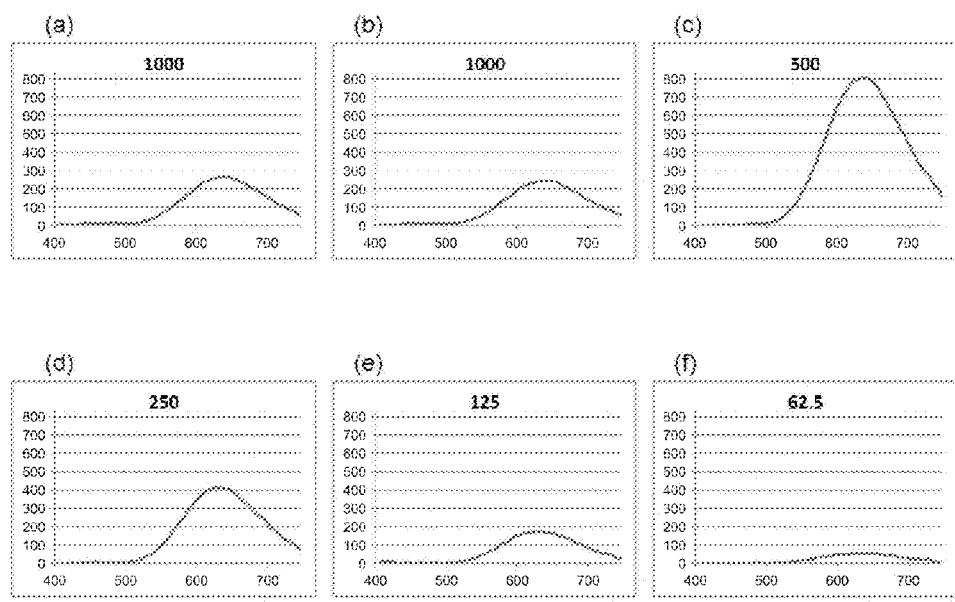
FIG. 34 Graphs each substituting a drawing and showing a fluorescent spectrum obtained in oligo-DNAs with T(5) at different concentrations (Example 5).
Figure 35:
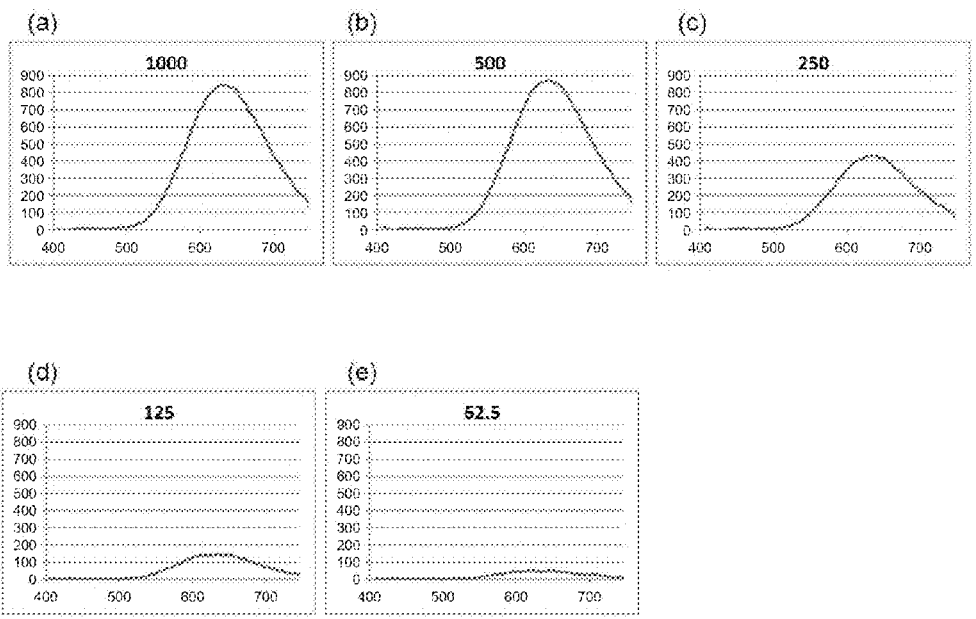
FIG. 35 Graphs each substituting a drawing and showing a fluorescent spectrum obtained in oligo-DNAs with T(4) at different concentrations (Example 5).
Figure 36:
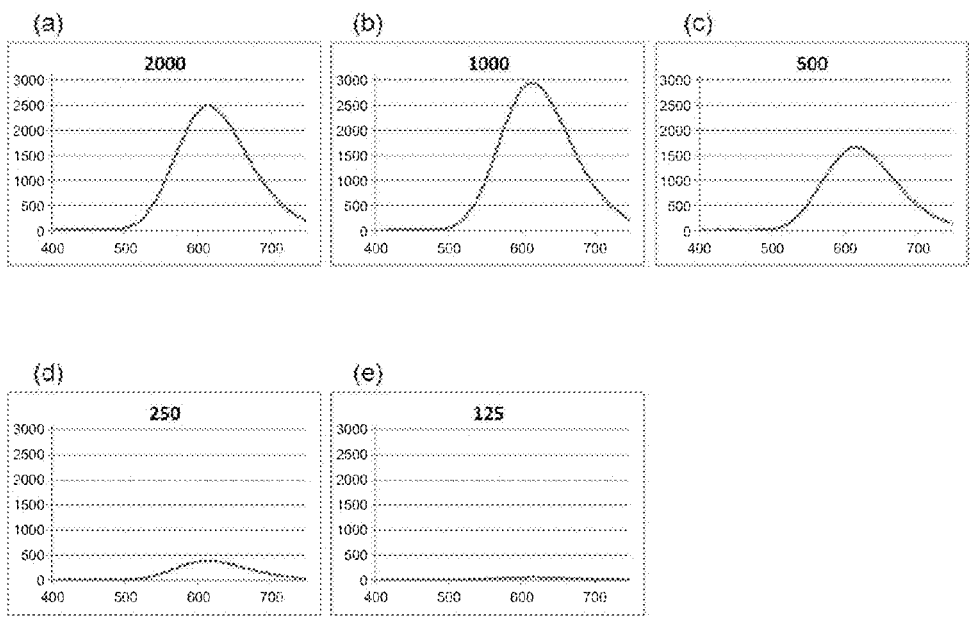
FIG. 36 Graphs each substituting a drawing and showing a fluorescent spectrum obtained in oligo-DNAs with T(3) at different concentrations (Example 5).
Figure 37:
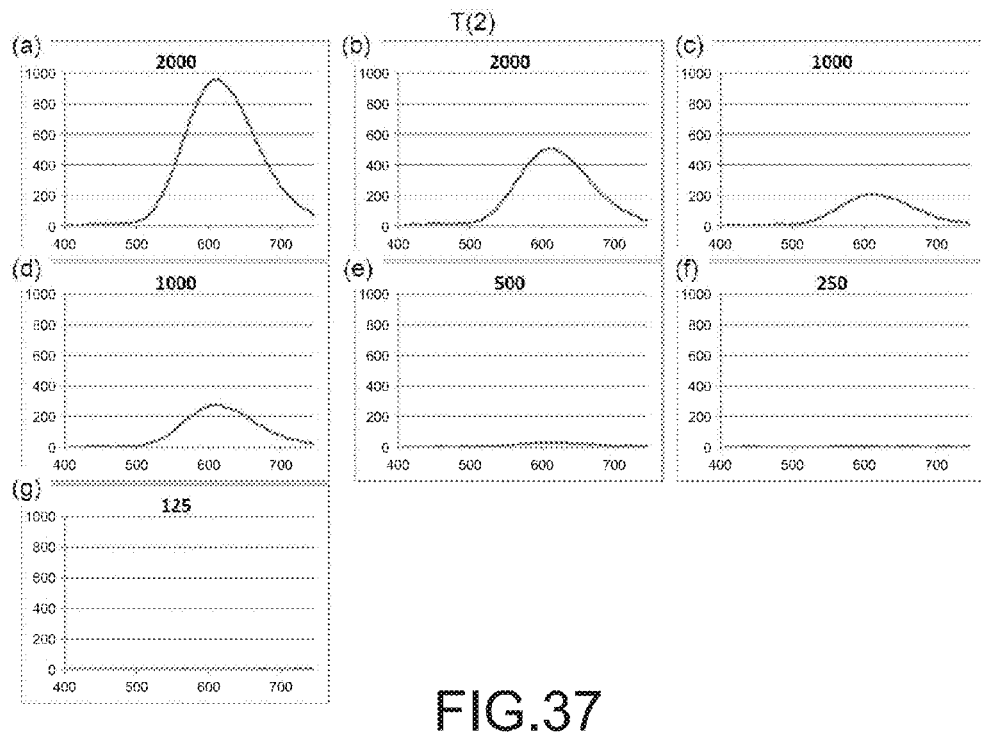
FIG. 37 Graphs each substituting a drawing and showing a fluorescent spectrum obtained in oligo-DNAs with T(2) at different concentrations (Example 5).

FIG. 31 shows measurement results of T(20). Respective concentrations of the oligo-DNAs are (a) 100 µM, (b) 50 µM, (c) 50 µM, (d) 25 µM, (e) 12.5 µM and (f) 6.25 µM. In each graph, an abscissa axis represents a wavelength (nm), and an ordinate axis represents fluorescence intensity (RFU value). FIGS. 32 to 37 show measurement results of respective oligo-DNAs T(10), T(6), T(5), T(4), T(3) and T(2). Numerical values shown in graphs in the Figures represent the concentrations of the oligo-DNAs.

Figure 38:
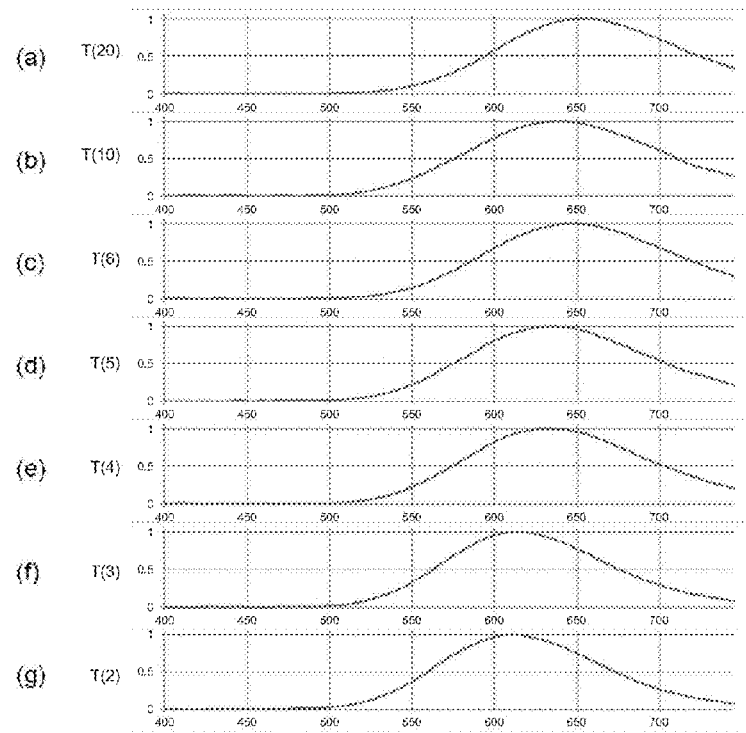
FIG. 38 Graphs each substituting a drawing and showing a fluorescent spectrum obtained in oligo-DNAs including different base numbers of thymine (Example 5).

FIG. 38 shows fluorescent spectra obtained in respective oligo-DNAs under the concentration condition where the fluorescence intensity was highest. An abscissa axis represents a wavelength (nm), and an ordinate axis represents a relative value (peak RFU value was set to 1). (a) represents a fluorescent spectrum of T(20), (b) represents a fluorescent spectrum of T(10), (c) represents a fluorescent spectrum of T(6), (d) represents a fluorescent spectrum of T(5), (e) represents a fluorescent spectrum of T(4), (f) represents a fluorescent spectrum of T(3) and (g) represents a fluorescent spectrum of T(2).

Figure 39:
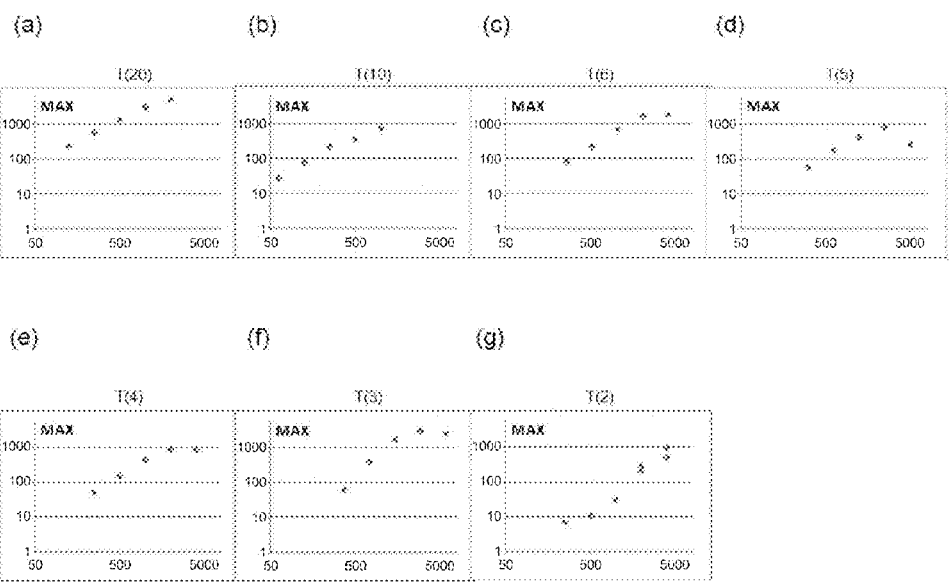
FIG. 39 Graphs each substituting a drawing and showing a relationship between a concentration of oligo-DNAs including different base numbers of thymine and a maximum value of a fluorescence intensity (Example 5).

FIG. 39 shows graphs for plotting the peak RFU values of respective oligo-DNAs in the respective concentrations. An abscissa axis represents a concentration of each oligo DNAs (μM), and an ordinate axis represents a peak RFU value (logarithmic value). (a) represents a result of T(20), (b) represents a result of T(10), (c) represents a result of T(6), (d) represents a result of T(5), (e) represents a result of T(4), (f) represents a result of T(3) and (g) represents a result of T(2).

<Discussion>

From the results of this Example, it was revealed that the fluorescence was observed from oligo-DNAs having a thymine two base length. It was found that the shape of the fluorescent spectrum was little changed even when the concentration of the oligo-DNAs was changed, but the fluorescent peak tended to be shifted to a short wavelength side as the base length became shorter (see FIG. 38). It was discerned that the intensity of the fluorescent spectrum tended to be dependent on the concentration of the oligo-DNAs, but reached plateau and was inversely reduced when the concentration exceeded the certain value (see FIG. 39). Also, it was observed that the fluorescence intensity was decreased when the concentration of DNAs was too high in the experiment where the copper powder was used in Example 2 (see FIG. 15).

Example 6

In Example 6, an experiment was made using oligo-DNAs having a three base length configured of T and C or of T and G under the similar experimental conditions as in Example 1.

<Material and Method>

Oligo-DNAs purchased from Invitrogen Corporation were measured for the fluorescence using the similar materials and method as in Example 1. The sequences of the oligo-DNAs used are TTT (SEQ ID NO: 12), TTC, TCT, CTT, TCC, CTC, CCT, CCC, TTG, TGT, GTT, TGG, GTG, GGT, GGG. A CuSO$_4$ concentration was set to 0.4 mM, an S.A. concentration was set to 4 mM, an oligo-DNA concentration was set to 0.5 mM, and the NanoDrop 3300 was used for measurement.

<Results>

Figure 40:
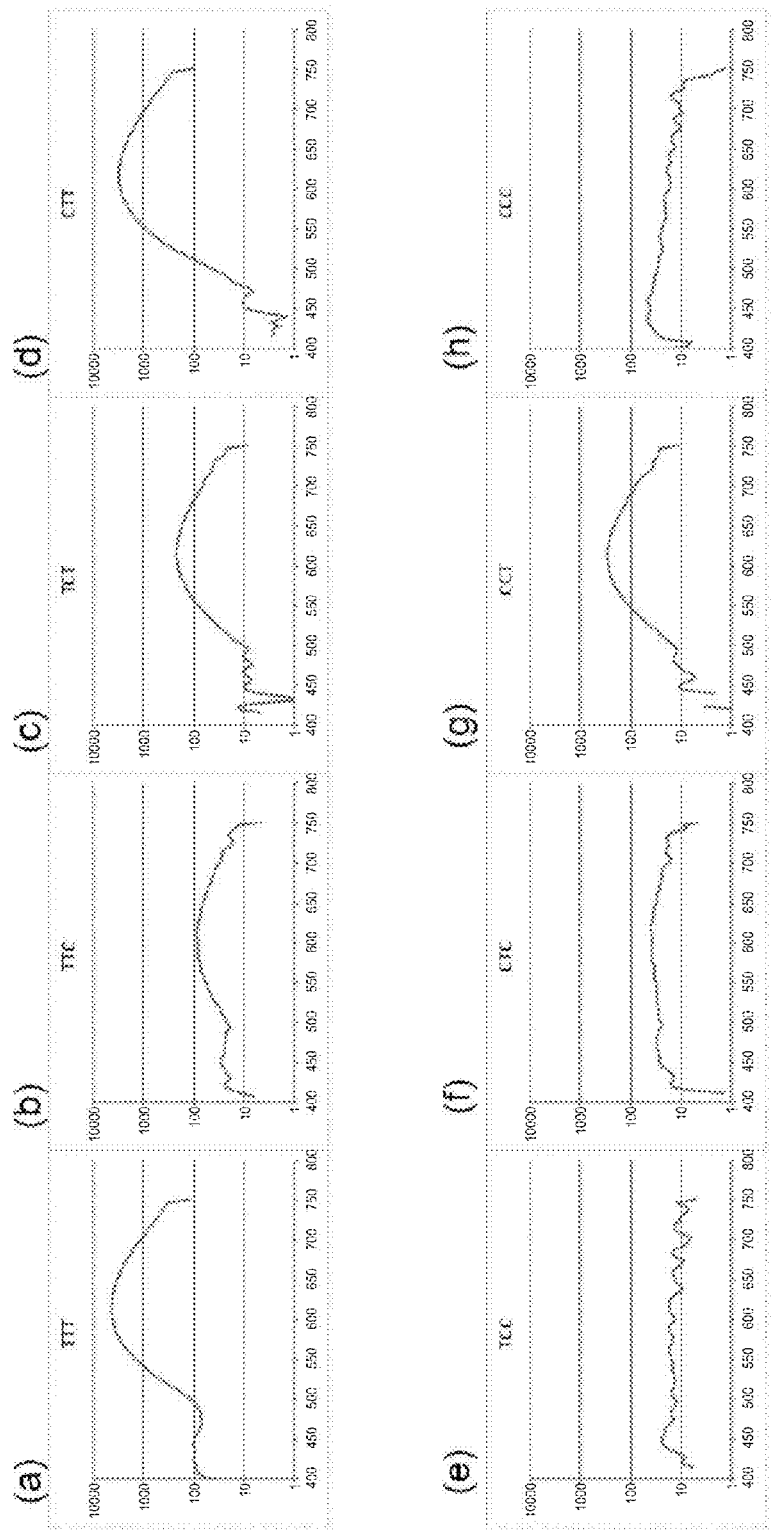
FIG. 40 Graphs each substituting a drawing and showing a fluorescent spectrum obtained in oligo-DNAs having base sequences including T and C (Example 6).
Figure 41:
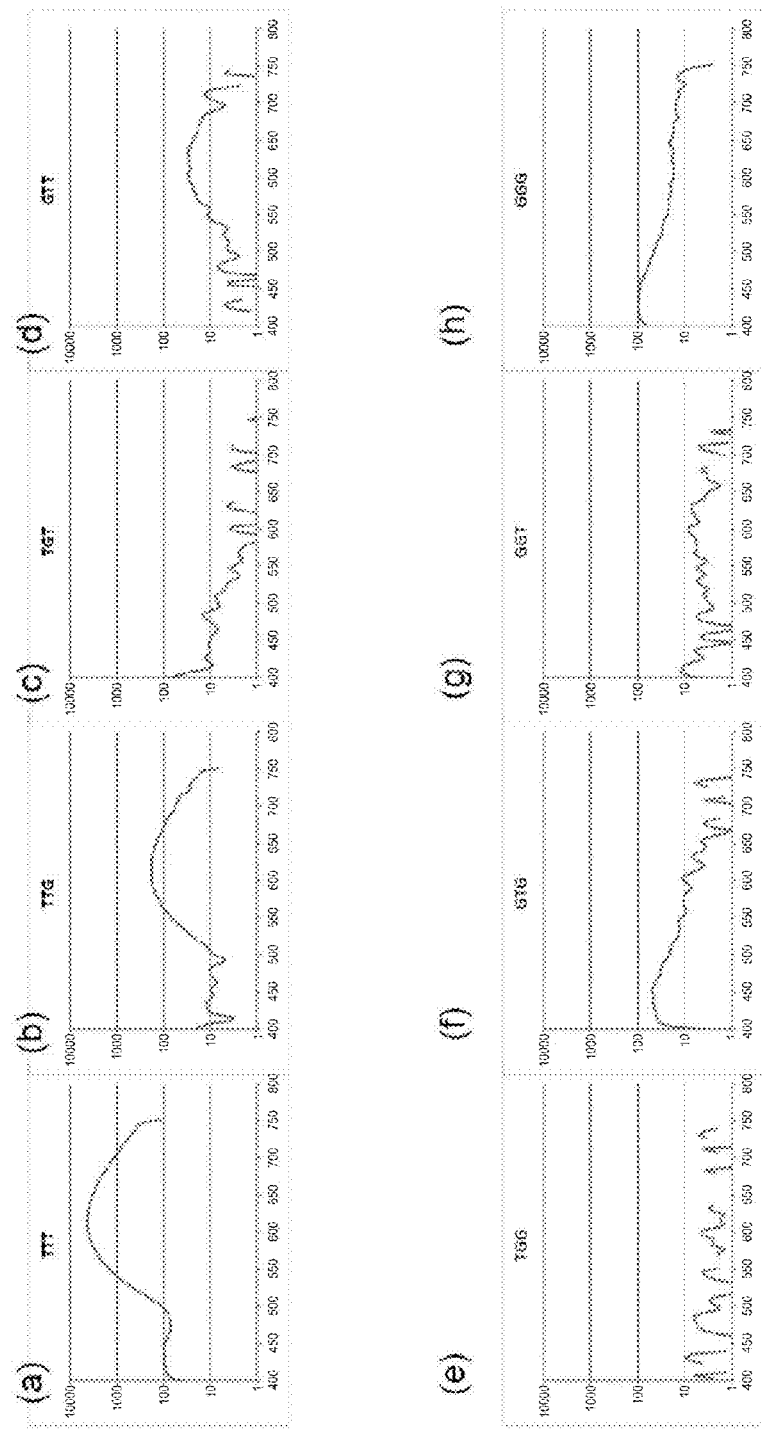
FIG. 41 Graphs each substituting a drawing and showing a fluorescent spectrum obtained in oligo-DNAs having base sequences including T and C (Example 6).

The results are shown in FIGS. 40 and 41. In FIG. 40, (a) represents a result of TTT (SEQ ID NO: 12), (b) represents a result of TTC, (c) represents a result of TCT, (d) represents a result of CTT, (e) represents a result of TCC, (f) represents a result of CTC, (g) represents a result of CCT, and (h) represents a result of CCC. In FIG. 41, (a) represents a result of TTT (SEQ ID NO: 12), (b) represents a result of TTG, (c) represents a result of TGT, (d) represents a result of GTT, (e) represents a result of TGG, (f) represents a result of GTG, (g) represents a result of GGT, and (h) represents a result of GGG. An abscissa axis represents a wavelength (nm), and an ordinate axis represents a logarithmic value of the fluorescence intensity (RFU value).

In the oligo-DNAs having a mixed sequence of T and C, the fluorescence intensity was strongest at TTT, then, CTT, CCT and TCT. Weak fluorescence was identified at TTC and CTC (see FIG. 40). On the other hand, no fluorescence having a peak at around 600 nm was identified at TCC and CCC. In the oligo-DNAs having a mixed sequence of T and G, the fluorescence having a moderate intensity was identified at TTG, weak fluorescence was identified at GTT, but no fluorescence having a peak at around 600 nm was identified at other sequences (see FIG. 41).

<Discussion>

In the oligo-DNAs having a mixed sequence of T and C, CTT including T at second and third positions showed the fluorescence intensity higher than those of TCT and TTC. Also, TCT and CCT including T at a third position showed the fluorescence intensity higher than those of TTC and CTC including T at a second position. From these, it is considered that, in the oligo-DNAs having a mixed sequence of T and C, T at a third base position highly contributes to fluorescence, and T at a second base position secondary contributes thereto.

In the oligo-DNAs having a mixed sequence of T and G, no fluorescence having a peak at around 600 nm was identified excluding TTG and GTT. The fluorescence intensity was generally lower than that of the oligo-DNAs having a mixed sequence of C and T. From this, it is considered that G has actions to absorb fluorescence energy and quench fluorescence.

Example 7

In Example 7, it was confirmed that fluorescence was quenched by a quench pigment.

<Material and Method>

Oligo-DNAs T(10) (SEQ ID NO: 19) purchased from Invitrogen Corporation and oligo-DNAs (T(10)BHQ2) (Sigma-Aldrich Corporation) provided by modifying 3' ends of the oligo-DNAs T(10) with Black Hole Quencher-2 (BHQ2) were used to measure the fluorescence using the similar materials and method as in Example 1. A CuSO$_4$ concentration was set to 0.4 mM, an S.A. concentration was set to 4 mM, an oligo-DNA concentration was set to 0.05 mM and the NanoDrop 3300 was used for measurement.

<Results>

Figure 42:
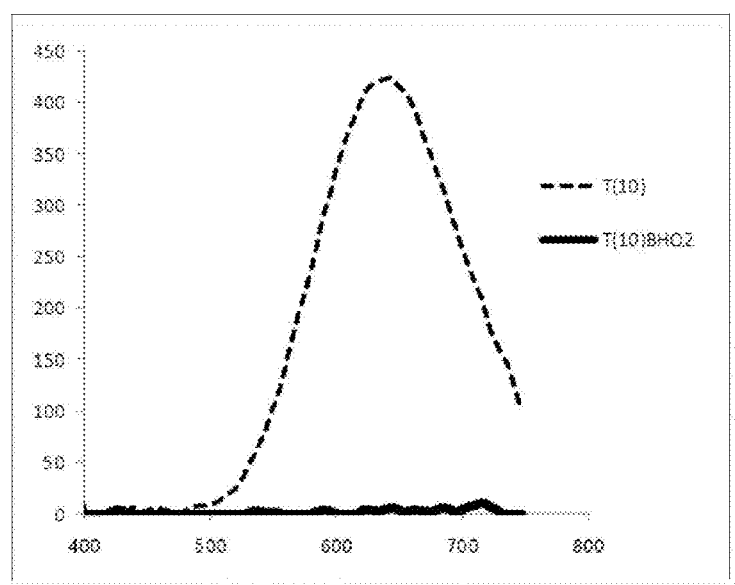
FIG. 42 A graph substituting a drawing and showing fluorescent spectra of oligo-DNAs with T(10) and the same oligo-DNAs with T(10) modified with a quencher (Example 7).

The results are shown in FIG. 42. An abscissa axis represents a wavelength (nm), and an ordinate axis represents a fluorescence intensity (RFU value). Obvious fluorescence was observed at T(10), but no fluorescence was detected from T(10)BHQ2 modified by the quencher.

<Discussion>

BHQ2 is a quencher that is known to effectively absorb light especially in the range of about 560 nm to 650 nm. It is considered that the fluorescence observed at T(10) was no more observed at T(10)BHQ2 by an effect of the BHQ2. The result suggests that it is possible to combine the action of copper with the FRET.

Example 8

In Example 8, fluorescence intensities and spectrum shapes of thymine (T) and uracil (U) were again compared, and it was confirmed that the intensities were different, but the spectrum shapes were identical between the both. Furthermore, methylated cytosine (MeC) and inosine (I) were examined for fluorescence generation, and it was revealed that both did not generate fluorescence.

<Material and Method>

A variety of oligo-DNAs were measured for fluorescence using the similar materials and method as in Example 1. As the oligo-DNAs, T(10) (SEQ ID NO: 19), U(9)G (SEQ ID NO: 20), A(10) (SEQ ID NO: 30) and I(9)G (SEQ ID NO: 31) purchased from Invitrogen Corporation were used. Also, as the oligo-DNAs, C(10) (SEQ ID NO: 32), C(4)MeC(6) (SEQ ID NO: 33, MeC is 5-methyl 2-deoxy-cytidin) purchased from Sigma-Aldrich Corporation was used. A CuSO$_4$ concentration was set to 0.4 mM, an S.A. concentration was set to 4 mM, an oligo-DNA concentration was set to 0.05 mM and the NanoDrop 3300 was used for measurement.

<Results>

Figure 43:
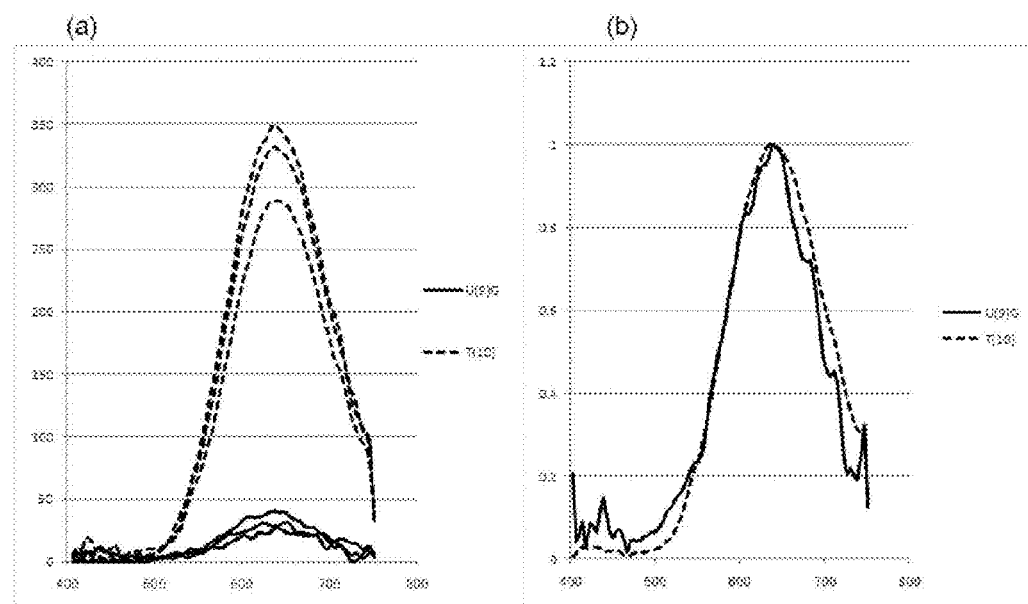
FIG. 43 Graphs each substituting a drawing and showing fluorescent spectra obtained by oligo-DNAs with T(10) and U(9)G (Example 8).

The results of measuring T(10) and U(9)G each for three times are shown in FIG. 43. (a) is a graph having an abscissa axis representing a wavelength (nm), and an ordinate axis representing fluorescence intensity (RFU value). (b) is a graph having an ordinate axis representing an average value of the fluorescence intensity (RFU value) as a relative value (peak RFU value of each oligo-DNA was set to 1). It was confirmed that U(9G) emitted the fluorescence having the lower strength but the similar spectrum shape than/to that of T(10).

Figure 44:
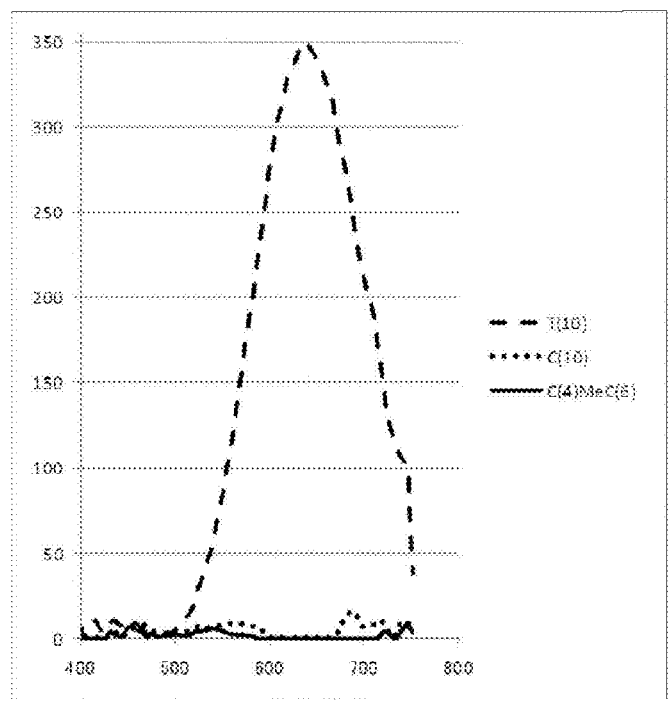
FIG. 44 A graph substituting a drawing and showing fluorescent spectra obtained by oligo-DNAs with T(10), C(10) and C(4)MeC(6) (Example 8).

The results of measuring T(10), C(10) and C(4)MeC(6) are shown in FIG. 44. An abscissa axis represents a wavelength (nm), and an ordinate axis represents fluorescence intensity (RFU). Noticeable fluorescence was observed from T(10), but no fluorescence was observed from C(10) and C(4)MeC(6).

Figure 45:
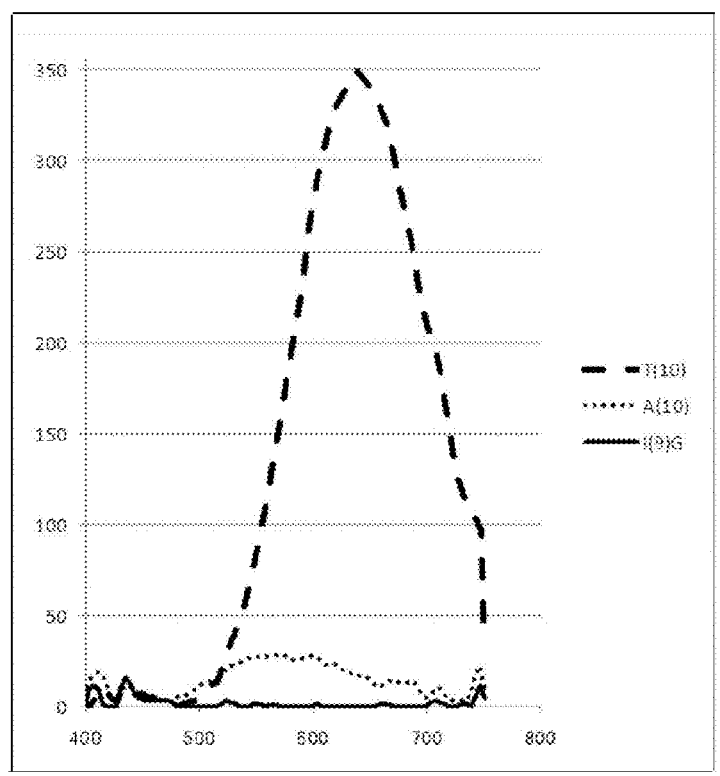
FIG. 45 A graph substituting a drawing and showing fluorescent spectra obtained by oligo-DNAs with T(10), A(10) and I(9)G (Example 8).

The results of measuring T(10), A(10) and I(9)G are shown in FIG. 45. An abscissa axis represents a wavelength (nm), and an ordinate axis represents fluorescence intensity (RFU). Noticeable fluorescence was observed from T(10), weak fluorescence was observed from A(10), but no fluorescence was observed from I(9)G.

<Discussion>

The nucleic acids having a uracil sequence emitted fluorescence having a lower intensity but a similar spectrum shape, as compared with that emitted from the nucleic acids having a thymine sequence. Example 1 supports this result. In addition, it was confirmed that the nucleic acids having a cytosine sequence or a cytosine and methylated cytosine sequence emitted no fluorescence.

From these results, it shows that uracil can be identified from cytosine and methylated cytosine by detecting fluorescence using copper. This suggests that the method of detecting nucleic acids according to the present invention can detect a replacement of cytosine (C) with uracil (U) by a bisulfate reaction, and analyze methylation of DNA molecules.

INDUSTRIAL APPLICABILITY

According to the present technology, only by bringing a sample into contact with copper, it is possible to easily detect or measure presence or absence of nucleic acids and the number, the base sequences in the sample; and the shape, the distribution, the number and size of cell nuclei in the sample.

This technology contributes to enhance analysis and analytical research of nucleic acids or a cells in a variety of fields including a medical field (pathology, tumor immunology, transplantation, genetics, regenerative medicine, chemical treatment, etc.), a drug discovery field, a clinical examination field, a food field, an agricultural field, an engineering field, a forensic medicine field and a criminal identification field.

The invention claimed is:

1. A method of detecting nucleic acids, comprising the steps of:
   providing copper in a powder form,
   bringing a sample containing the nucleic acids into contact with the copper in a powder form to form a composite of the nucleic acids and Cu(I) ions, and
   detecting a fluorescence emitted from the composite of the nucleic acids and the Cu(I) ions.

2. The detection method according to claim 1, comprising analyzing at least one base sequence of the nucleic acids based on at least one of an intensity of the fluorescence emitted from the composite and a spectrum of the fluorescence emitted from the composite.

3. The detection method according to claim 2, comprising detecting a mismatch in a double strand formed by the nucleic acids based on the at least one of the intensity of the fluorescence emitted from the composite and the spectrum of the fluorescence emitted from the composite.

4. The detection method according to claim 2, comprising the steps of:
   treating the sample with bisulfate, and
   analyzing methylation or demethylation of cytosine in the nucleic acids based on at least one of a difference between an intensity of the fluorescence emitted from the composite before the bisulfate treatment and an intensity of the fluorescence emitted from the composite after the bisulfate treatment, and a difference between a spectrum of the fluorescence emitted from the composite before the bisulfate treatment and a spectrum of the fluorescence emitted from the composite after the bisulfate treatment.

5. The detection method according to claim 2, wherein the step of bringing the sample into contact with the copper in a powder form is performed under coexistence of a salt.

6. The detection method according to claim 2, comprising irradiating the sample with light having a wavelength of 300 to 420 nm in order to detect the fluorescence emitted from the composite.

7. The detection method according to claim 1, wherein an amount of the copper in a powder form to be contacted with the sample is greater than or equal to 37.5 mg per ml of the sample.

8. A method of optically observing a sample containing nucleic acids, comprising the steps of:
providing copper in a powder form,
bringing the sample into contact with the copper in a powder form to form a composite of the nucleic acids and Cu(I) ions, and
detecting a fluorescence emitted from the composite of the nucleic acids and the Cu(I) ions, wherein the sample comprises a cell.

9. A method of analyzing a base sequence of nucleic acids, comprising the steps of:
bringing a sample containing the nucleic acids into contact with copper in a powder form, to form a composite of the nucleic acids and Cu(I) ions,
measuring at least one of an excitation spectrum and an emission spectrum of fluorescence emitted from the sample,
determining a fluorescence intensity of the fluorescence emitted from the sample and a spatial distribution of the fluorescence intensity, and
analyzing at least one base sequence of the nucleic acids based on at least one of the fluorescence intensity, a spectrum of the fluorescence emitted from the sample, and the spatial distribution of the fluorescence intensity.

10. The method according to claim 9, comprising analyzing a mismatch of thymine in a double strand formed by the nucleic acids based on at least one of the fluorescence intensity and the spectrum of the fluorescence emitted from the sample.

11. The method according to claim 9, comprising the steps of:
treating the sample with bisulfate, and
analyzing methylation or demethylation of cytosine in the nucleic acids based on at least one of a difference between a fluorescence intensity of the fluorescence emitted from the sample before the bisulfate treatment and a fluorescence intensity of the fluorescence emitted from the sample after the bisulfate treatment, and a difference between a spectrum of the fluorescence emitted from the composite before the bisulfate treatment and a spectrum of the fluorescence emitted from the composite after the bisulfate treatment.

12. The method according to claim 9, wherein the step of bringing the sample containing the nucleic acids into contact with the copper in a powder form comprises contacting the sample with copper in a powder form in an amount greater than or equal to 37.5 mg per ml of the sample.

* * * * *